(12) United States Patent
Dixit

(10) Patent No.: US 11,890,306 B2
(45) Date of Patent: Feb. 6, 2024

(54) LYOPHILIZED COMPOSITIONS COMPRISING FECAL MICROBE-BASED THERAPEUTIC AGENTS AND METHODS FOR MAKING AND USING SAME

(71) Applicant: Finch Therapeutics Holdings LLC, Somerville, MA (US)

(72) Inventor: Bharat Dixit, Acton, MA (US)

(73) Assignee: Finch Therapeutics Holdings LLC, Boston, MA (US)

( * ) Notice: Subject to any disclaimer, the term of this patent is extended or adjusted under 35 U.S.C. 154(b) by 469 days.

(21) Appl. No.: 16/616,846

(22) PCT Filed: May 25, 2018

(86) PCT No.: PCT/US2018/034673
§ 371 (c)(1),
(2) Date: Nov. 25, 2019

(87) PCT Pub. No.: WO2018/218159
PCT Pub. Date: Nov. 29, 2018

(65) Prior Publication Data
US 2020/0254027 A1 Aug. 13, 2020

Related U.S. Application Data

(60) Provisional application No. 62/511,776, filed on May 26, 2017.

(51) Int. Cl.
| | | |
|---|---|---|
| *A61K 35/74* | (2015.01) | |
| *A61K 9/19* | (2006.01) | |
| *A61K 47/18* | (2017.01) | |
| *A61K 47/22* | (2006.01) | |
| *A61K 47/26* | (2006.01) | |
| *A61K 9/00* | (2006.01) | |

(52) U.S. Cl.
CPC .............. *A61K 35/74* (2013.01); *A61K 9/19* (2013.01); *A61K 47/18* (2013.01); *A61K 47/22* (2013.01); *A61K 47/26* (2013.01); *A61K 9/0053* (2013.01)

(58) Field of Classification Search
CPC ........ A61K 9/0053; A61K 9/19; A61K 39/00; A61K 47/22
USPC ....... 424/93.1, 93.3, 93.4, 234.1, 278.1, 543
See application file for complete search history.

(56) References Cited

U.S. PATENT DOCUMENTS

| | | |
|---|---|---|
| 3,192,116 A | 6/1965 | Mose et al. |
| 3,320,130 A | 5/1967 | Henry |
| 3,713,836 A | 1/1973 | Carlsson |
| 4,098,728 A | 7/1978 | Rosenblatt |
| 4,309,782 A | 1/1982 | Paulin |
| 4,332,790 A | 6/1982 | Sozzi et al. |
| 4,335,107 A | 6/1982 | Snoeyenbos et al. |
| 4,394,377 A | 7/1983 | Spires |
| 4,452,779 A | 6/1984 | Cockerill |
| 4,536,409 A | 8/1985 | Farrell et al. |
| 4,657,762 A | 4/1987 | Mikkola et al. |
| 4,710,379 A | 12/1987 | Kawai et al. |
| 4,892,731 A | 1/1990 | Arai et al. |
| 4,975,286 A | 12/1990 | Hechter |
| 5,213,807 A | 5/1993 | Chemburkar et al. |
| 5,266,315 A | 11/1993 | Taguchi et al. |
| 5,443,826 A | 8/1995 | Borody |
| 5,728,380 A | 3/1998 | Allen et al. |
| 5,800,821 A | 9/1998 | Acheson et al. |
| 5,837,238 A | 11/1998 | Casas et al. |
| 5,858,356 A | 1/1999 | Wolf et al. |
| 5,902,578 A | 5/1999 | Halpin-Dohnalek et al. |
| 5,902,743 A | 5/1999 | Luchansky et al. |
| 6,087,386 A | 7/2000 | Chen et al. |
| 6,162,464 A | 12/2000 | Jacob et al. |
| 6,245,740 B1 | 6/2001 | Goldenberg et al. |
| 6,284,274 B1 | 9/2001 | Merrill et al. |
| 6,428,783 B1 | 8/2002 | Khachatrian et al. |
| 6,479,051 B1 | 11/2002 | Bruce |
| 6,514,531 B1 | 2/2003 | Alaux et al. |
| 6,645,530 B1 | 11/2003 | Borody |
| 6,649,397 B1 | 11/2003 | Nakamura |
| 6,756,032 B1 | 6/2004 | Tepper et al. |
| 6,926,907 B2 | 8/2005 | Plachetka |

(Continued)

FOREIGN PATENT DOCUMENTS

| | | |
|---|---|---|
| AU | 2001276160 B2 | 6/2007 |
| CA | 1333564 | 12/1994 |

(Continued)

OTHER PUBLICATIONS

Canglosi et al., "Dead and Alive: Molecular Assessment of Microbiol Viability," *Applied and Environmental Microbiology* 80(19):5884-5891 (12014).
Shannon et al., "The Mathematical Theory of Communication," *The University of Illinois Press, Urbana* pp. 117 (1949).
Stocks, "Mechanism and Use of the Commercially Available Viability Stain, BacLight," *Cytometry Part A* 61A:189-195 (2004).
"Autoimmune Disease List," *American Autoimmune Related Diseases Association*, pp. 1-4 (2017) <https://www.aarda.org/diseaselist/>.
"Certain infectious and parasitic diseases (A00-B99)," *International Statistical Classification of Diseases and Related Health Problems*, 10th Revision (ICD-10)WHO Version, Chapter 1, pp. 1. (2016) <www.apps.who.int/classifications/icd 0/browse/2016/en#II>.
"Spore-Forming Gram-Positive Bacilli: *Bacillus* and *Clostridium* Species," *jawetz, Melnick, & Adelberg's Medical Microbiology*, 26th Edition, Chapter 11, pp. 1-15 (2012).

(Continued)

*Primary Examiner* — Robert A Zeman
(74) *Attorney, Agent, or Firm* — Arnold & Porter Kaye Scholer LLP

(57) ABSTRACT

This application provides compositions, e.g., formulations, used for gastric, gastrointestinal and/or colonic treatments, and methods for making, storing and using them, including formulations that effectively preserve microbial cell viability during freeze-thaw or freeze-drying. Compositions provided herein are useful for treating various diseases or conditions such as autism spectrum disorder, Crohn's Disease, ulcerative colitis, irritable bowel syndrome, and recurrent or primary *C. difficile* infection.

17 Claims, 1 Drawing Sheet

(56) References Cited

U.S. PATENT DOCUMENTS

| | | | |
|---|---|---|---|
| 6,979,674 B1 | 12/2005 | Goldenberg et al. | |
| 6,984,513 B2 | 1/2006 | Brown et al. | |
| 7,018,629 B2 | 3/2006 | Jacob et al. | |
| 7,374,753 B1 | 5/2008 | Farmer et al. | |
| 7,541,091 B2 | 6/2009 | Sisson et al. | |
| 7,749,509 B2 | 7/2010 | Cobb et al. | |
| 7,763,276 B1 | 7/2010 | Shodai et al. | |
| 7,799,341 B2 | 9/2010 | Porzio et al. | |
| 7,815,956 B2 | 10/2010 | Lee et al. | |
| 7,846,475 B2 | 12/2010 | Shiraishi et al. | |
| 7,888,062 B1 | 2/2011 | Garner et al. | |
| 7,998,510 B2 | 8/2011 | Caswell | |
| 8,168,171 B2 | 5/2012 | Mogna et al. | |
| 8,460,648 B2 | 6/2013 | Borody | |
| 8,586,029 B2 | 11/2013 | Kasper et al. | |
| 8,637,297 B2 | 1/2014 | Fernandez et al. | |
| 8,658,153 B2 | 2/2014 | Daube et al. | |
| 8,771,673 B2 | 7/2014 | Cobb et al. | |
| 9,040,036 B2 | 5/2015 | Borody | |
| 9,050,358 B2 | 6/2015 | Borody | |
| 9,308,226 B2 | 4/2016 | Borody | |
| 9,320,763 B2 | 4/2016 | Borody | |
| 9,408,872 B2 | 8/2016 | Borody | |
| 9,468,658 B2 | 10/2016 | Borody | |
| 9,572,841 B2 | 2/2017 | Borody | |
| 9,572,842 B2 | 2/2017 | Borody | |
| 9,610,308 B2 | 4/2017 | Borody | |
| 9,623,056 B2 | 4/2017 | Borody | |
| 9,719,144 B2 | 8/2017 | Krajmalnik-Brown et al. | |
| 9,901,603 B2 * | 2/2018 | Borody | A61K 9/19 |
| 10,821,138 B2 * | 11/2020 | Borody | A61K 47/10 |
| 10,980,839 B2 | 4/2021 | Affagard et al. | |
| 2001/0014322 A1 | 8/2001 | Chen et al. | |
| 2002/0013270 A1 | 1/2002 | Bolte | |
| 2002/0022019 A1 | 2/2002 | Laulund | |
| 2002/0039599 A1 | 4/2002 | Lin et al. | |
| 2003/0092163 A1 | 5/2003 | Collins et al. | |
| 2003/0092724 A1 | 5/2003 | Kao et al. | |
| 2003/0147858 A1 | 8/2003 | Renaud et al. | |
| 2004/0062757 A1 | 4/2004 | Finegold | |
| 2004/0167062 A1 | 8/2004 | Bolte | |
| 2004/0170617 A1 | 9/2004 | Finegold | |
| 2004/0223956 A1 | 11/2004 | Naidu et al. | |
| 2006/0076536 A1 | 4/2006 | Barshied | |
| 2006/0099197 A1 | 5/2006 | Farmer | |
| 2006/0115465 A1 | 6/2006 | Macfarlane et al. | |
| 2006/0177424 A1 | 8/2006 | Cobb et al. | |
| 2006/0275223 A1 | 12/2006 | Burr | |
| 2007/0059296 A1 | 3/2007 | Chen | |
| 2008/0254009 A1 | 10/2008 | Finegold | |
| 2008/0299197 A1 | 12/2008 | Toneguzzo et al. | |
| 2010/0112003 A1 | 5/2010 | Collins et al. | |
| 2010/0178349 A1 | 7/2010 | Kolter et al. | |
| 2010/0178413 A1 | 7/2010 | Gorris | |
| 2010/0184785 A1 | 7/2010 | Kolter et al. | |
| 2010/0222311 A1 | 9/2010 | Thommes et al. | |
| 2010/0226866 A1 | 9/2010 | Yamashiro et al. | |
| 2010/0233278 A1 | 9/2010 | Ookaa et al. | |
| 2010/0239667 A1 | 9/2010 | Hemmingsen et al. | |
| 2010/0247489 A1 | 9/2010 | Saur-Brosch et al. | |
| 2010/0247665 A1 | 9/2010 | Takahashi | |
| 2010/0255231 A1 | 10/2010 | Chau et al. | |
| 2010/0255307 A1 | 10/2010 | Gonze et al. | |
| 2010/0278930 A1 | 11/2010 | Okumura et al. | |
| 2010/0285164 A1 | 11/2010 | Schaible et al. | |
| 2010/0289164 A1 | 11/2010 | Porzio et al. | |
| 2010/0297031 A1 | 11/2010 | Ubeda Perez et al. | |
| 2011/0008554 A1 | 1/2011 | Chen et al. | |
| 2011/0045222 A1 | 2/2011 | Peters | |
| 2011/0081320 A1 | 4/2011 | Westall et al. | |
| 2011/0200570 A1 | 8/2011 | Mosbaugh et al. | |
| 2011/0218216 A1 | 9/2011 | Vivek et al. | |
| 2012/0020941 A1 | 1/2012 | Wacklin et al. | |
| 2012/0039853 A1 | 2/2012 | Corveleyn et al. | |
| 2012/0064133 A1 | 3/2012 | Chauhan et al. | |
| 2012/0087895 A1 | 4/2012 | Mazmanian et al. |
| 2012/0183612 A1 | 7/2012 | Brogmann et al. |
| 2012/0252775 A1 | 10/2012 | Finegold |
| 2013/0045274 A1 | 2/2013 | Hlavka |
| 2013/0195804 A1 | 8/2013 | Borody |
| 2013/0259899 A1 | 10/2013 | Allen-Vercoe et al. |
| 2013/0316394 A1 | 11/2013 | Stimpson |
| 2014/0065132 A1 | 3/2014 | Hsiao et al. |
| 2014/0086877 A1 | 3/2014 | Hlavka |
| 2014/0147417 A1 | 5/2014 | Sadowsky et al. |
| 2014/0147425 A1 | 5/2014 | Henn et al. |
| 2014/0234260 A1 | 8/2014 | Borody |
| 2014/0255351 A1 | 9/2014 | Berstad et al. |
| 2014/0328803 A1 | 11/2014 | McKenzie et al. |
| 2014/0341921 A1 | 11/2014 | Honda et al. |
| 2014/0342438 A1 | 11/2014 | Allen-Vercoe et al. |
| 2014/0363397 A1 | 12/2014 | Allen-Vercoe et al. |
| 2014/0363398 A1 | 12/2014 | Jones et al. |
| 2015/0044173 A1 | 2/2015 | Jones et al. |
| 2015/0050246 A1 | 2/2015 | Jones et al. |
| 2015/0093360 A1 | 4/2015 | McKenzie et al. |
| 2015/0143557 A1 | 5/2015 | Honda et al. |
| 2015/0152484 A1 | 6/2015 | Krajmalnik-Brown et al. |
| 2015/0190435 A1 | 7/2015 | Henn et al. |
| 2015/0224152 A1 | 8/2015 | Littman et al. |
| 2015/0238544 A1 | 8/2015 | Jones et al. |
| 2015/0238545 A1 | 8/2015 | Borody |
| 2015/0238546 A1 | 8/2015 | Borody |
| 2015/0297642 A1 | 10/2015 | Borody |
| 2015/0306144 A1 | 10/2015 | Borody |
| 2015/0306155 A1 | 10/2015 | Borody |
| 2015/0306156 A1 | 10/2015 | Borody |
| 2015/0374761 A1 | 12/2015 | Sadowsky et al. |
| 2016/0089363 A1 | 3/2016 | Borody |
| 2016/0151429 A1 | 6/2016 | Borody |
| 2016/0151431 A1 | 6/2016 | Borody |
| 2016/0151432 A1 | 6/2016 | Borody |
| 2016/0151433 A1 | 6/2016 | Borody |
| 2016/0158294 A1 | 6/2016 | Von Maltzahn et al. |
| 2016/0279178 A1 | 9/2016 | Borody |
| 2016/0279179 A1 | 9/2016 | Borody |
| 2016/0339065 A1 | 11/2016 | Adams et al. |
| 2017/0216378 A1 | 8/2017 | Honda et al. |
| 2017/0246220 A1 | 8/2017 | Sato et al. |
| 2017/0348360 A1 | 12/2017 | Borody |
| 2018/0153943 A1 | 6/2018 | Borody |
| 2018/0256652 A1 | 9/2018 | Borody |
| 2019/0015460 A1 | 1/2019 | Borody |
| 2019/0015461 A1 | 1/2019 | Borody |
| 2019/0015462 A1 | 1/2019 | Borody |
| 2019/0046589 A1 | 2/2019 | Borody |

FOREIGN PATENT DOCUMENTS

| | | |
|---|---|---|
| CA | 2 391 422 A1 | 1/2004 |
| CN | 1561387 A | 1/2005 |
| CN | 101496819 A | 8/2009 |
| CN | 201441672 U | 4/2010 |
| CN | 103764154 A | 4/2014 |
| CN | 105193858 A | 12/2015 |
| DE | 2 134 179 A1 | 1/1973 |
| EP | 0 303 426 A2 | 2/1989 |
| EP | 0 456 418 A2 | 11/1991 |
| EP | 0 433 299 | 5/1998 |
| EP | 1 514 572 A2 | 3/2005 |
| EP | 1 514 572 A3 | 11/2006 |
| EP | 1 800 688 A1 | 6/2007 |
| EP | 1 514 572 B1 | 12/2008 |
| EP | 2 823 822 B1 | 10/2016 |
| FR | 1275 M | 5/1962 |
| FR | 2427 M | 3/1964 |
| FR | 2828 M | 10/1964 |
| FR | 5528 M | 11/1967 |
| FR | 2 244 464 A1 | 4/1975 |
| GB | 1271674 A | 4/1972 |
| JP | 64-67192 | 3/1989 |
| JP | H05-306221 A | 11/1993 |
| JP | H07-242539 A | 9/1995 |
| JP | H07-242557 A | 9/1995 |

(56) References Cited

FOREIGN PATENT DOCUMENTS

| | | |
|---|---|---|
| JP | 3 144 556 B2 | 3/2001 |
| JP | 2004-501095 | 1/2004 |
| JP | 2005-118544 A | 5/2005 |
| JP | 2008-106066 | 5/2008 |
| JP | 2009-531275 | 9/2009 |
| JP | 2010-513359 | 4/2010 |
| JP | 2010-520234 A | 6/2010 |
| KR | 10-0913405 B1 | 8/2009 |
| WO | WO 90/01335 A1 | 2/1990 |
| WO | WO 95/33046 A1 | 12/1995 |
| WO | WO 96/11014 A1 | 4/1996 |
| WO | WO 98/13068 A1 | 4/1998 |
| WO | WO 00/07571 A2 | 2/2000 |
| WO | WO 00/015760 | 3/2000 |
| WO | WO 00/42168 A2 | 7/2000 |
| WO | WO 02/07741 A1 | 1/2002 |
| WO | WO 03/033681 A2 | 4/2003 |
| WO | WO 2005/017095 A2 | 2/2005 |
| WO | WO 2006/127355 A2 | 11/2006 |
| WO | WO 2007/070677 A2 | 6/2007 |
| WO | WO 2008/077614 A2 | 7/2008 |
| WO | WO 2008/105715 A2 | 9/2008 |
| WO | WO 2008/117266 A2 | 10/2008 |
| WO | WO 2008/117267 A2 | 10/2008 |
| WO | WO 2008/077614 A3 | 1/2009 |
| WO | WO 2009/024429 A2 | 2/2009 |
| WO | WO 2009/026306 A2 | 2/2009 |
| WO | WO 2009/055362 A1 | 4/2009 |
| WO | WO 2010/040020 A1 | 4/2010 |
| WO | WO 2011/033310 A1 | 3/2011 |
| WO | WO 2011/094027 A1 | 8/2011 |
| WO | WO 2011/110347 A2 | 9/2011 |
| WO | WO 2011/151941 A1 | 12/2011 |
| WO | WO 2012/013861 A2 | 2/2012 |
| WO | WO 2012/016287 A2 | 2/2012 |
| WO | WO 2012/045150 A1 | 4/2012 |
| WO | WO 2012/122478 A1 | 9/2012 |
| WO | WO 2012/016287 A3 | 11/2012 |
| WO | WO 2012170915 A1 | 12/2012 |
| WO | WO 2013/037067 A1 | 3/2013 |
| WO | WO 2013/090825 A1 | 6/2013 |
| WO | WO 2014/070014 A1 | 5/2014 |
| WO | WO 2014/078911 A1 | 5/2014 |
| WO | WO 2014/152338 A1 | 9/2014 |
| WO | WO 2014/152484 A1 | 9/2014 |
| WO | WO 2015/006355 A2 | 1/2015 |
| WO | WO 2015/051323 A1 | 4/2015 |
| WO | WO 2015/077794 A1 | 5/2015 |
| WO | WO 2015/095241 A2 | 6/2015 |
| WO | WO 2015/124637 A1 | 8/2015 |
| WO | WO 2016/133450 A1 | 2/2016 |
| WO | WO 2016/170285 A1 | 10/2016 |
| WO | WO 2016/183577 A1 | 11/2016 |
| WO | WO 2016/191356 A1 | 12/2016 |
| WO | WO 2017/075098 A1 | 5/2017 |
| WO | WO 2017/079450 A1 | 5/2017 |
| WO | WO 2017/152137 A2 | 9/2017 |

OTHER PUBLICATIONS

"ARGF—'Autologous Rehabilitation of Gastrointestinal Flora,'" Medipex Report for Medilink NW, pp. 1-42, n.d., Web, Feb. 10, 2012 <http://www.bacteriotherapy.og/docs/medipex-report.pelf>.
"Frequently Asked Questions about *Clostridium difficile* for Healthcare Providers," Healthcare-assistated Infections (HAis), Centers for Disease Control and Prevention, pp. 1-6, Nov. 25, 2010, updated Mar. 6, 2012, Web, May 19, 2014 <http://www.cdc.gov/HAI/organisms/cdiff/Cdiff faqs HCP.html>.
"Functional Anatomy of Prokaryotic and Eukaryotic Cells," printed Mar. 16, 2017 <http://classes.midlandstech.edu/carterp/courses/bio225/chap04/lecture2.htm>.
"Monilia," Def. 1, Stedman's Medical Dictionary, n.d., Web, Nov. 22, 2005.
"Probiotic," Def. 1, MSN Encarta—Dictionary, Encarta, n.d., Web, Dec. 1, 2005.
Aas et al., "Recurrent *Clostridium difficile* Colitis: Case Series Involving 18 Patients Treated with Donor Stool Administered via a Nasogastric Tube," *Clinical Infectious Diseases*, 36(5):580-585 (2003).
Abrams, "Open-Label, Uncontrolled Trial of Bowel Sterilization and Repopulation with Normal Bowel Flora for Treatment of Inflammatory Bowel Disease," *Current Therapeutic Research*, 58(12):1001-1012 (1997).
Acha et al., "Changes of viability and composition of the *Escherichia coli* in faecal samples during long time storage," Journal of Microbiological Methods, Elsevier, 63(3):229-238 (2005).
Agrawal et al., "'Global warming' to *Mycobacterium avium* subspecies paratubercolosis," *Future Microbial*, 9(7):829-832 (2014).
Agrawal et al., "A Long-Term Follow-Up Study of the Efficacy and Safety of Fecal Microbiota Transplant (FMT) for Recurrent/Severe/Complicated *C. difficile* Infection (CDI) in the Elderly," *Gastroenterol*, 146(5)(Suppl 1):S42-S43 (2014).
Aitken et al., "Demonstration of Intracellular *Mycobacterium* Species in Crohn's Disease Using Novel Technologies," Poster Presentation—2015 ACG Annual Scientific Meeting, Honolulu, Hawaii, USA (2015).
Akao et al., "A Purgative Action of Barbaloin Is Induced by *Eubacterium* sp. Strain BAR, a Human Intestinal Anaerobe, Capable of Transforming Barbaloin to Aloe-EmodinAnthrone," Biol. Pharm., 19(1):136-138 (1996).
Al-Eidan et al., "Clostridium difficile-associated diarrhoea in hospitalised patients," *J Clin. Pharm. Ther.*, 25(2):101-109 (2000).
Al-Nassir et al., "Comparison of Clinical and Microbiological Response to Treatment of Clostridium difficile-Associated Disease with Metronidazole and Vancomycin," *Clin Infect Dis.*, 47(1):56-62 (2008).
Anand et al., "Epidemiology, clinical manifestations, and outcome of Clostridium difficile-associated diarrhea," *Am J Gastroenterol.*, 89(4):519-23 (1994).
Ananthakrishnan et al., "Excess hospitalisation burden associated with Clostridium difficile in patients with inflammatory bowel disease," *Gut*, 57(2):205-210 (2007).
Anderson et al., "Systematic review: faecal microbiota transplantation in the management of inflammatory bowel disease," *Aliment. Pharmacol. Ther.*, 36:503-16 (2012).
Andoh et al., "Terminal restriction fragment polymorphisum analyses of fecal microbiota in five siblings including two with ulcerative colitis," *Journal of Clinical Gastroenterology*, 2:343-345 (2009).
Andrews et al., "'Putting back the bugs': Bacterial Treatment Relieves Chronic Constipation and Symptoms of Irritable Bowel Syndrome," *Med. J Aust.*, 159(9):633-634 (1993).
Andrews et al., "Bacteriotherapy for Chronic Constipation—A Long Term Follow-Up," *Gastroenterol*, 108:A563 Abstract (1995).
Andrews et al., "Chronic Constipation (CC) may be reversed by Bacteriotherapy," *Gastroenterol*, 106:A459 (1994).
Andrews et al., "Chronic constipation reversed by restoration of bowel flora. A case and hypotheses," *European Journal of Gastroenterology & Hepatology*, 4:245-247 (1992).
Anorexia nervose, Encyclopedia Index A, health AtoZ, Medical Network, Inc., pp. 1-7, n.d., Web, Nov. 23, 2005 <http://www.healthatoz.com/healthatoz/Atoz/ency/anorexia_nervosa.jsp>.
Arkkila et al., "Fecal Bacteriotherapy for Recurrent *Clostridium difficile* Infection," *Gastroenterology*, 138(5):S1-S5 (2010).
Aroniadis et al., "Intestinal Microbiota and the Efficacy of Fecal Microbiota Transplantation in Gastrointestinal Disease," Gastroenterology and Hepatology, 10(4): 230-7 (2014).
Aroniadis et al., "Long-Term Follow-up Study of Fecal Microbiota Transplantation (FMT) for Severe or Complicated *Clostridium difficile* Infection (CDI)," *Gastroenterol*, 144(Suppl 1):S185 (2013).
Atarashi et al., "Induction of Colonic Regulatory T Cells by Indigenous *Clostridium* Species," *Science*, 331(6015):337-341, published online Dec. 23, 2010.
Atarashi et al., "$T_{reg}$ induction by a rationally selected mixture of *Clostridia* strains from the human microbiota," *Nature*, 500(7461):232-236 (2013).

(56) References Cited

OTHER PUBLICATIONS

Atarashi et al., "WS/PP-064-03 Regulation of colonic regulatory T cells by *Clostridium* species," *International Immunology*, 22(Suppl 1, Part 3), pp. 1-3 (2010).

Atarashi et al., WS-064 Mucosal immunity: homeostasis, 14th ICIC Abstract book, 14th International Congress of Immunology, pp. iii131-iii133 (2010).

Autism, Health Encyclopedia—Diseases and Conditions, The Health Scout Network, pp. 1-5, n.d., Web, Nov. 22, 2005 <www.healthscout.com>.

Autism, Treatment, Prognosis, Healthcommunities.com, Inc., pp. 1-4, n.d., Web. Jan. 28, 2009 <http://www.neurologychannel.com/common/PrintPage.php>.

Autism: Mayo Clinic.com, Mayo Foundation for Medical Education and Research, pp. 1-7, May 31, 2008, Web. Jan. 28, 2009 <http://www.mayoclinic.com/print/autism/DS00348/METHOD=print&DSECTION=all>.

Backhed et al., "Host-bacterial mutualism in the human instestine," *Science*, 307(5717):1915-1920 (2005).

Backhed et al., "Mechanisms underlying the resistance to diet-induced obesity in germ-free mice," *PNAS USA*, 104(3):979-984 (2007).

Backhed et al., "The gut microbiota as an environmental factor that regulates fat storage," *PNAS USA*, 101(44):15718-15723 (2004).

Bakken et al., "Fecal bacteriotherapy for recurrent Clostridium difficile infection," *Anaerobe*, 15(6):285-289 (2009).

Bakken et al., "Treating Clostridium difficile Infection with Fecal Microbiota Transplantation," *Clinical Gastroenterology and Hepatology*, 9(12):1044-1049 (2011).

Bartlett et al., "Clinical recognition and diagnosis of Clostridium difficile infections," *Clin Infect Dis.*, 46(Suppl 1):S12-S18 (2008).

Bartlett, "Clostridium difficile-associated Enteric Disease," *Curr Infect Dis Rep.*, 4(6):477-483 (2002).

Belkaid et al., "Natural regulatory T cells in infectious disease," *Nature Immunology*, 6(4):353-360 (2005).

Bengmark et al., "Bioecological control of inflammatory bowel disease," *Clinical Nutrition*, 26(2):169-181 (2007).

Bennet et al., "Treatment of ulcerative colitis by implantation of normal colonic flora," *Lancet*, 333(8630):164 (1989).

Benson et al., "Changing epidemiology of Clostridium difficile-associated disease in children," *Infect Control Hosp Epidemiol.*, 28(11):1233-1235 (2007).

Bergey's Manual of Systematic Bacteriology, Second Edition, vol. 3, The Firmicutes, pp. 1-16 (2009).

Blaser et al., "What are the consequences of the disappearing human microbiota?" *Nat. Rev. Microbial.*, 7(12):887-894 (2009).

Blaser, "Who are we? Indigenous microbes and the ecology of human diseases," *EMBO Rep*, 7(10):956-960 (206).

Bolte, "Autism and Clostridium tetani," Medical Hypotheses, 51(12):133-144 (1998).

Bolte, "Therapies for Gastrointestinal and Neurological Disorders," U.S. Appl. No. 60/214,813, filed Jun. 28, 2000.

Borody et al., "Fecal microbiota transplantation in gastrointestinal disease: 2015 update and the road ahead," Expert Review of Gastroenterology and Hepatology, 9(11):1379-1391 (2015).

Borody et al., "Anti-MAP Rescues Anti-TNF Failures for Over 4 Years," *Gastroenterol*, 136(5)Suppl 1:A-681 (2009).

Borody et al., "Anti-MAP Therapy for Pediatric Crohn's Disease," *Am J Gastroenterol*, 108(Suppl 1):S516 (2013).

Borody et al., "Anti-MAP Therapy in the Treatment of Active Crohn's Disease," *J Gastroenterol * Hepatol*, 20(Suppl):A2 (2005).

Borody et al., "Anti-mycobacterial therapy in Crohn's disease heals mucosa with longitudinal scars," *Digestive & Liver Disease*, 39(5):438-444 (2007).

Borody et al., "Anti-*Mycobacterium avium* SS Paratuberculosis (MAP) Therapy and Fistula Closure in Patients with Severe Crohn's Disease," *Am J Gast*, AI 0J:S440 (2006).

Borody et al., "Bacteriotherapy in Chronic Fatigue Syndrome (CFS): A retrospective review," *AmJGastro*, 107(SJ):A1481 (2012).

Borody et al., "Bacteriotherapy Using Fecal Flora: toying with human motions" *J Clin. Gastroenterol.*, 38(6):475-483 (2004).

Borody et al., "Bowel-flora alteration: a potential cure for inflammatory bowel disease and irritable bowel syndrome?" *Med. J Aust.*, 150:604 (1989).

Borody et al., "Changes in Crohn's Disease Activity Index and C-Reactive Protein Levels During Anti-MAP Therapy," *AM J Gastro*, 104(S3):A1293 (2009).

Borody et al., "Clostridium *difficile* Complicating Inflammatory Bowel Disease: Pre- and Post-Treatment Findings," *Gastroenterol*, 134(4)Suppl 1:A-361 (2008).

Borody et al., "Could fecal microbiota transplantation cure all Clostridium difficile infections?," *Future Microbial*, 9:1-3 (2014).

Borody et al., "Entamoeba *histolytica*: another cause of Crohn's Disease," *AM J Gastro*, 104(S3):A990 (2009).

Borody et al., "Faecal bacteriotherapy (FB) for chronic C. *difficile* (Cd) syndromes," *J Gastroenterol Hepatol*, 1 8(Suppl.) :B8 (Abstract) (2003).

Borody et al., "Fecal bacteriotherapy in the treatment of recurrent C. difficile infection," *UpToDate*, pp. 1-6 (2006).

Borody et al., "Fecal Microbiota Transplantation (FMT) in Multiple Sclerosis (MS)," *AMJGastro*, 106(S2):A942 (2011).

Borody et al., "Fecal microbiota transplantation and emerging applications," *Nat. Rev. Gastroenterol. Hepatol.*, 9(2):88-96 (2011).

Borody et al., "Fecal microbiota transplantation for *Clostridium difficile* infection: A surgeon's perspective" *Seminars in Colon and Rectal Surgery*, 25:163-166 (2014).

Borody et al., "Fecal microbiota transplantation in gastrointestinal diseases—What practicing physicians should know," *Polish Archives of Internal Medicine*, 125(11):852-858 (2015).

Borody et al., "Fecal microbiota transplantation in the treatment of recurrent Clostridium difficile infection," *UpToDate*, pp. 1-4, (2015).

Borody et al., "Fecal Microbiota Transplantation in Ulcerative Colitis: Review of 24 Years Experience," *Am J Gastro*, 107(Supp 1):A1644 (2012).

Borody et al., "Fecal microbiota transplantation: a new standard treatment option for *Clostridium difficile* infection," *Expert Rev Anti Infect Ther.*, 11(5):447-449 (2013).

Borody et al., "Fecal microbiota transplantation: current status and future directions," *Expert Review of Gastroenterology & Hepatology*, 5(6):653-655 (2011).

Borody et al., "Fecal Microbiota Transplantation: Expanding Horizons for *Clostridium difficile* Infections and Beyond," *Antibiotics*, 4:254-266 (2015).

Borody et al., "Fecal Microbiota Transplantation: Indications, Methods, Evidence, and Future Directions," *Curr Gastroenterol Rep*, 15:337-344 (2013).

Borody et al., "Fecal Microbiota Transplantation: Techniques, Applications, and Issues," *Gastroenterol Clin North Am*, 41:781-803 (2012).

Borody et al., "Irritable Bowel Syndrome and *Dientamoeba fragilis*," *ASM Sydney National Conference*, pp. 4-5 (2002).

Borody et al., "Is Crohn's Disease Ready for Fecal Microbiota Transplantation?," *J Clin Gastroenterol*, 48(7):582-583 (2014).

Borody et al., "Myoclonus-dystonia affected by GI Microbiota?," *AM J Gastro*, 106(S2):A940 (2011).

Borody et al., "Novel appearance of healing mucosa following anti-*Mycobacterium avium paratuberculosis* therapy for Crohn's disease," *J Gastroenterol Hepatol*, 19(Suppl) :A210 (2004).

Borody et al., Reveral of Idiopathic Thrombocytopenic Purpura [ITP] with Fecal Microbiota Transplantation [FMT], *Am J Gastro*, 106(S2):A941 (2011).

Borody et al., "Reversal of Inflammatory Bowel Disease (IBD) with Recurrent Faecal Microbiota Transplants (FMT)," *AM J Gastro*, 106(S2):A979 (2011).

Borody et al., "Severe recurrent Crohn's Disease of ileocolonic anastomosis and antimicrobial (anti-mycobacterial therapy)," *Gut*, 55:1211 (2006).

Borody et al., "The Gi Microbiome and its Role in Chronic Fatigue Syndrome: a Summary of Bacteriotherapy," ACNEM Journal, 31(3):3-8 (2012).

(56) References Cited

OTHER PUBLICATIONS

Borody et al., "Therapeutic faecal microbiota transplantation: current status and future developments," *Curr Opin Gastroenterol*, 30:97-105 (2014).
Borody et al., "Treatment of chronic constipation and colitis using human probiotic infusions," *Proceedings of Prebiotics and Probiotics and the New Foods Conference*, 2-4:228 Abstract (2001).
Borody et al., "Treatment of First-time Clostridium difficile Infection with Fecal Microbiota Transplantation," Poster Presentation, *2015 ACG Annual Scientific Meeting*, Honolulu, Hawaii, USA (2015).
Borody et al., "Treatment of Severe Constipation Improves Parkinson's Disease (PD) Symptoms,"*AM J Gastro*, 104(S3):A999 (2009).
Borody et al., "Treatment of Severe Crohn's Disease (CD)—Usin Rifabutin-Macrolide-Clofazimine Combination: Results at 30-37 Months," *Gastroenterology*, 118(4):A1334 Abstract (2000).
Borody et al., Treatment of Severe Crohn's Disease Using Rifabutin-Macrolide-Clofazimine Combination—Results at 38-43 Months, *J Gastroenterol & Hepatol*, 15(Suppl.):J102 (2000).
Borody et al., "Treatment of Severe Crohn's disease using antimycobaacterial triple therapy—approaching a cure?," *Digest Liver Dis*, 34(1):29-38 (2002).
Borody et al., "Treatment of ulcerative colitis using fecal bacteriotherapy," *J Clin. Gastroenterol.*, 37(1):42-47 (2003).
Borody, "Bacteriotherapy for Chronic Fatigue Syndrome—A Long Term Follow-Up Study," Proceedings of ACMA Complementary Medicine Sydney, p. 1 (1995).
Borody, "Flora Power"—Fecal Bacteria Cure Chronic C. difficile Diarrhoea, *Am J Gastroenterol*, 95(11):3028-3029 (2000).
Borody, "Is the Infected Patient too 'Difficile' to Treat?, " The Australian Society for Microbiology 2009 Perth, SY03 & SY03, 1, p. 27 & 56, (2009).
Borody, "Letter to the Editor—Response to Drs. Famularo et al.," *AJG*, 96(7):2262-2264 (2001).
Borriello, "Clostridial Disease of the Gut," Clinical Infectious Diseases, The University of Chicago, 20(Suppl 2):S242-S250 (1995).
Bowden et al., "Pseudomembraneous enterocolitis: mechanism of restoring floral homeostasis," *Am Surg.*, 47(4):178-183 (1981).
Brandt et al., "Endoscopic Fecal Microbiota Transplantation: "First-Line" Treatment for Severe Clostridium difficile Infection?" *J. Clin. Gastroenterol.*, 45(8):655-657 (2011).
Brandt et al., "Fecal microbiota transplantation for recurrent *Clostridium difficile* infection," *JClin Gastroenterol.*, 45(Suppl):S159-S167 (2011).
Brandt et al., "Long-Term Follow-Up Study of Fecal Microbiota Transplantation (FMT) for Ulcerative Colitis (UC)," Am. J. Gastroenterol., 107(Suppl I):S657 (2012).
Brandt et al., Safety of Fecal Microbiota Transplantation (FMT) in Immunocompromised (Ie) Patients with Inflammatory Bowel Disease (IBD), *Am J Gastroenterol*, 108(Suppl 1):S556 (2013).
Browne et al., "Culturing of 'unculturable' human microbiota reveals novel taxa and extensive sporulation," *Nature*, 533(7604):543-546 (2016).
Bueche et al., "Quantification of Endospore-Forming *Firmicutes* by Quantitative PCR with the Functional Gene Spo0A," *Applied and Environmental Microbiology*, 79(17):5302-5312 (2013).
Cammarota et al., "Randomised clinical trial: faecal microbiota transplantation by colonoscopy vs. vancomycin for the treatment of recurrent Clostridium difficile infection," Alimentary Pharmacology & Therapeutics, 41(9):835-843 (2015).
Cammorata et al., "Review article: biofile formation by Helicobacter pylori as a target for eradication of resistant infection," Aliment Pharmacol Ther, 36:222-30 (2012).
Campbell et al., "The many faces of Crohn's Disease: Latest concepts in etiology," *OJIM*, 2(2):107-115 (2012).
Cano et al., "Revival and identification of bacterial spores in 25-40 million year old Dominical Amber Science," Science, 268(5213):1060-1064 (1995).
Cato et al., "*Clostridium oroticum* comb. nov. amended description," *International Journal of Systematic Bacteriology*, 17(1):9-13 (1968).
Celik et al., "Factors influencing the stability of freeze-dried stress-resilient and stress-sensitive strains of bifidobacteria," J. Dairy Sci., 96(6):3506-16 (2013).
Center for Disease Control, "Severe Clostridium difficile-associated disease in populations previously at low risk-four states, 2005." *MOrbidity and Mortality Weekly Report*, 54(47):1201-1205 (2005).
Chamberlain et al., "MAP-associated Crohn's Disease, MAP, Koch's postulates, causality and Crohn's Disease," *Digestive and Liver DIsease*, 39:790-794 (2007).
Chamberlin et al., "Primary treatment of Crohn's disease: combined antibiotics taking center stage," *Expert Rev. Clin. Immunol.*, 7(6):751-760 (2011).
Chang et al., "Decreased diversity of the fecal Microbiome in recurrent Clostridium difficile-associated diarrhea," *J. Infect. Dis.*, 197(3):435-438 (2008).
Chen et al., "A mouse model of Clostridium difficile-associated disease," *Gastroenterology*, 135(6):1984-1992 (2008).
Cherif et al., "Thuricin 7: a novel bacteriocin produced by Bacillus thuringiensis BMGI.7, a new strain isolated from soil," Letters in Applied Microbiology, 32:243-7 (2001).
Chibani-Chennoufi et al., "In Vitro and In Vivo Bacteriolytic Activities of *Escherichia coli* Phages: Implications for Phage Therapy," *Antimicrobial Agents and Chemotherapy*, 48(7):2558-2569 (2004).
Choi et al., "Fecal Microbiota Transplantation: Current Applications, Effectiveness, and Future Perspectives," Clin. Endosc., 49:257-265 (2016).
Chopra et al., "Recent epidemiology of Clostridium difficile infection during hematopoietic stem cell transplantation," *Clin Transplant.*, 25(1):E82-E87 (2011).
Chu et al., "Profiling Living Bacteria Informs Preparation of Fecal Microbiota Transplantations," *PLOS One*, 1-16 (2017).
Citron et al., "In Vitro Activities of CB-183,315, Vancomycin, and Metronidazole against 556 Strains of *Clostridium difficile*, 445 Other Intestinal Anaerobes, and 56 *Enterobacteriaceae* Species," *Antimicrob Agents Chemother.*, 56(3):1613-1615 (2012).
Claesson et al., "Comparison of two next-generation sequencing technologies for resolving highly complex microbiota composition using tandem variable 16S rRNA gene regions," *Nucleic Acids Research*, 38(22):1-13 (2010).
Clancy et al., "Anti-MAP Therapy Induces and Maintains Remission in Severe Crohn's Disease," *Ann NY Acad Sci*, p. 1 (2005).
Claus et al., "Colonization-induced host-gut microbial metabolic interaction," *MBio*, 2(2):e00271-00210 (2011).
Claus et al., "Systemic multicompartmental effects of the gut microbiome on mouse metabolic phenotypes," *Mal. Syst. Biol.*, 4(1):219 (2008).
Cohen et al., "Clinical practice guidelines for Clostridium difficile infection in adults: 2010 update by the society for healthcare epidemiology of America (SHEA) and the infectious diseases society of America (IDSA)," *Infect Control Hosp Epidemiol.*, 31(5):431-55 (2010).
Collins et al., "The Phylogeny of the Genus *Clostridium*: Proposal of Five New Genera and Eleven New Species Combinations," *International Journal of Systematic Bacteriology*, pp. 812-826 (1994).
U.S. Appl. No. 12/843,409, filed Jul. 26, 2010.
Crohn's Disease, Prevention, Health Guide A-Z, WebMCHealth, pp. 1-2, n.d., Web, Oct. 23, 2005 <http://mywebmd.com/hw/inflammatory.sub.-bowel/uf6012.asp>.
Crowther, "Transport and Storage of Faeces for bacteriological Examination," Journal of Applied Bacteriology, 34(2):477-483 (1971).
Cutolo et al., "Fecal feedings as a therapy in *Staphylococcus enterocolitis*," NY State J Med, 59:3831-3833 (1959).
Dale et al., "Molecular interactions between bacterial symbionts and their hosts," *Cell*, 126(3):453-465 (2006).
Dan et al., "Comparison of preservation media and freezing conditions for storage of specimens of faeces," J. Med Microbiology, 28:151-154 (1989).
De Giulio et al., "Use of Alginate and Cryo-Protective Sugars to Improve the Viability of Lactic Acid Bacteria After Freezing and Freeze-Drying," World Journal of Microbiology & Biotechnology, 21:739-746 (2005).

(56) References Cited

OTHER PUBLICATIONS

Defant et al., "In vitro and in vivo evaluation of two extended release preparations of combination metformin and glipizide," *Drug Develop. & Indust. Pharm.*, 31:677-685 (2005).
Definition of Kit, Merriam-Webster, pp. 1-10., Web., 2019 <https://www.merriam-webster.com/dictionary/kit>.
Dendukuri et al., "Probiotic therapy for the prevention and treatment of Clostridium difficile-associated diarrhea: a systematic review," *CMAJ*, 173(2):167-170 (2005).
Derwent Abstract Accession No. 98-230427/20, WO 98/13068 A, (Kuperman VB) Apr. 2, 1998.
Dethlefsen et al., "An ecological and evolutionary perspective on human-microbe mutualism and disease," *Nature*, 449(7164):811-818 (2007).
Dewhirst et al., "Phylogeny of the Defined Murine MIcrobiota: Altered Schaedler Flora," *Applied and Environmental Microbiology*, 65(8):3287-3292 (1999).
DuPont, "The search for effective treatment of Clostridium difficile infection," *N Engl J Med.*, 364(5):473-475 (2011).
Eckburg et al., "Diversity of the human intestinal microbial flora," *Science*, 308(5728):1635-1638 (2005).
Eiseman et al., "Fecal enema as an adjunct in the treatment of pseudomembranous enterocolitis," *Surgery*, 44(5):854-859 (1958).
Eller et al., "Anaerobic Roll Tube Media for Nonselective Enumeration and Isolation and Bacteria in Human Feces," Applied Microbiology, 22(4):522-529 (1971).
Extended European Search Report dated Apr. 3, 2014, in European Patent Application No. 11813951.8.
Extended European Search Report dated Mar. 16, 2018, in European Patent Application No. 17203052.0
Extended European Search Report dated Nov. 30, 2016, in European Patent Application No. 16193790.9.
Faust et al., "Treatment of recurrent pseudomembranous colitis (RPMC) with stool transplantation (ST): Report of six (6) cases," *Can J Gastroenterol.*, 16:A43 (2002).
Fenton et al., "Pseudomembranous colitis associated with antibiotic therapy—an emerging entity," *Can Med Assoc J*, 111(10):1110-1111 (1974).
Floch et al., "Probiotics and Dietary Fiber, The Clinical Coming of Age of Intestinal Microecology," J. Clin. Gastroenterology, 27(2):99-100 (1998).
Floch, "Fecal Bacteriotherapy, Fecal Transplant, and the Microbiome," J. Clin. Gastroenterol., 44(8):529-530 (2010).
Flotterod et al., "Refractory Clostridium difficile infection. Untraditional treatment of antibiotic-induced colitis," *Tidsskr Nor Laegeforen*, 111:1364-1365 (1991).
Frank et al., "Molecular-phylogenetic characterization of microbial community imbalances in human inflammatory bowel diseases," *PNAS*, 104(34):13780-13785.
Frantzen et al., "Empirical evaluation of preservation methods for faecal DNA," *Molecular Ecology*, 7(10):1423-1428 (1998).
Freeman et al., "The changing epidemiology of Clostridium difficile infections," *Clin Microbial. Rev.*, 23(3):529-549 (2010).
Frese et al., "The evolution of host specialization in the vertebrate gut symbiont Lactobacillus reuteri," *PloS Genet.*, 7(2):e1001314 (2011).
Gaboriau-Routhiau et al., "The Key Role of Segmented Filamentous Bacteria in the Coordinated Maturation of Gut Helper T Cell Responses," *Immunity*, 31(4):677-689 (2009).
Garborg et al., "Results of faecal donor instillation therapy for recurrent Clostridium difficile-associated diarrhoea," *Scand J Infect Dis.*, 42(11-12):857-61 (2010).
Garey et al., "Meta-analysis to assess risk factors for recurrent Clostridium difficile infection," *J Hosp. Infect.*, 70(4):298-304 (2008).
Gerding, "Management of Clostridium difficile infection: thinking inside and outside the box," *Clin Infect Dis.*, 51(11):1306-13 (2010).
Geuking et al., "Intestinal Bacterial Colonization Induces Mutualistic Regulatory T Cell Responses," *Immunity*, 34:794-806 (2011).
Gitlin et al., "*Mycobacterium avium* ss *paratubercolis*-associated Diseases: Piecing the Crohn's Puzzle Together," *J Clin Gastroenterol*, 46(8):649-655 (2012).
Gough et al., "Systematic review of intestinal microbiota transplantation (fecal bacteriotherapy) for recurrent Clostridium difficile infection," *Clin. Infect. Dis.*, 53(10):994-1002 (2011).
Grehan et al., "Durable alteration of the colonic microbiota by the administration of donor fecal flora," *Journal of Clinical Gastroenterology*, 44(8):551-561 (2010).
Guarner et al., "Gut flora in health and disease," *Lancet*, 361(9356):512-519 (2003).
Gustafsson et al., "The Effect of Faecal Enema on Five Microflora-Associated Characteristics in Patients with Antibiotic-Associated Diarrhoea," *Scandinavian Journal of Gastroenterology*, 34:580-586 (1999).
Gustafsson et al., "Gaecal Short-Chain Fatty Acids in Patients with Antibiotic-Associated Diarrhoea, before and after Faecal Enema Treatment," *Scand J Gastroenterol*, 33:721-727 (1998).
Hamilton et al., "Change in microbial community composition of in patients with recalcitrant Clostridium difficile colitis treated with fecal bacteriotherapy," International Human Microbiome Congress, Poster and Presentation, Vancouver, ON, Canada, Mar. 9-11, 2011.
Hamilton et al., "High-throughput DNA sequence analysis reveals stable engraftment of gut microbiota following transplantation of gut microbiota following transplantation of previously frozen fecal bacteria," *Gut Microbes*, 4(2):1-11 (2013).
Hamilton et al., "Standardized Frozen Preparation for Transplantation of Fecal Microbiota for Recurrent Clostridium difficile Infection," Article and Supplementary Material, Am. *J. Gastroenterol.*, 107(5):761-767 (2012).
Hayashi et al., "Phylogenetic Analysis of the Human Gut Microbiota Using 16S rDNA Clone Libraries and Strictly Anaerobic Culture-Based Methods," *Microbial. Immunol.*, 46(8):535-548 (2002).
Hecker et al., "Fecal Microbiota Transplantation by Freeze-Dried Oral capsules for Recurrent Clostridium difficile Infections," *Open Forum Infect Dis*, 3(2): 1-2 (2016).
Hellemans et al., "Fecal transplantation for recurrent Clostridium difficile colitis, an underused treatment modality," *Acta Gastroenterol Belg.*, 72(2):269-70 (2009).
Henriksson et al., "Probiotics under the regulatory microscope," *Expert Opin. Drug Saf*, 4(6):1-9 (2005).
Hensel et al., "Vagal Ascent and Distribution of 125 I-Tetanus Toxin after Injection into the Anterior Wall of the Stomach," Naunyn-Schmiedeberg's Arch. Pharmacol, 276:395-402 (1973).
Honda et al., "Regulation of T Cell Responses by Intestinal Commensal Bacteria," *Journal of Intestinal Microbiology*, vol. 25, 2nd Edition:104 (2011).
Hongliang et al., "Freeze-dried, Capsulized Fecal Microbiota Transplantation for Relapsing Clostridium difficile Infections," *Journal of Clinical Gastroenterology*, 43(6):537-538 (2015).
Hooper et al., "How host-microbial interactions shape the nutrient environment of the mammalian intesting," *Annu. Rev. Nutr.*, 22:283-307 (2002).
Hope et al., "Sporadic colorectal cancer-role of the commensal microbiota," *FEMS Microbial. Lett.*, 244:1-7 (2005).
Hota et al., "Determining Mortality Rates Attributable to Clostridium difficile Infection," *Emerg. Infect. Dis.*, 18(2):305-307 (2012).
Hota et al., "Oral Vancomycin Followed by Fecal Transplant Versus Tapering Oral Vancomycin," U.S. National Institutes of Health, Clinical Study No. NCT01226992, Oct. 20, 2010, last updated Jan. 13, 2013, Web, May 20, 2014, pp. 1-4 <http://clinicaltrials.gov/ct2/show/NCT01226992>.
Hsu et al., "IL-10 Potentiates Differentiation of Human Induced Regulatory T Cells via STAT2 and Foxol," *The Journal of Immunology*, 3665-3674 (2015).
Hu et al., "Prospective derivation and validation of a clinical prediction rule for recurrent Clostridium difficile infections," *Gastroenterology*, 136:1206-1214 (2009).
Huang et al., "Once-daily propranolol extended-release tablet dosage form: formulation design and in vitro/in vivo investigation," *European J of Phar. & Biopharm.*, 58:607-614 (2004).

(56) References Cited

OTHER PUBLICATIONS

Huttenhower et al., "Structure, function and diversity of the healthy human microbiome," The Human Microbiome Project Consortium, *Nature*, 486:207-214 (2012).
Immunology in the 21st Century: Defeating Infection, Autoimmunity, Allergy, and Cancer, ICI 2010 Wrap-up Report, 14th International Congress of Immunology, pp. 1 (2010).
Inflammatory Bowel Disease Facts, Disease Prevention and Treatment Strategies, Crohn's Disease and Inflammatory Bowel Disease (IBD), HealingWithNutrition.com, pp. 1-4, n.d., Web, Oct. 23, 2005 <http://www.HealingWithNutrition.com/disease/inflambowel/chrohns.html>.
Information Disclosure Statement filed Nov. 28, 2017, in U.S. Appl. No. 15/487,553.
International Preliminary Examination Report completed Nov. 19, 2002, in International Application No. PCT/AU2001/000907, 19 pgs.
International Preliminary Report on Patentability completed Dec. 12, 2012, in International No. PCT/AU2011/000987, 35 pgs.
International Preliminary Report on Patentability completed Mar. 12, 2015, in International Application No. PCT/AU2013/001362, 29 pgs.
International Preliminary Report on Patentability dated Sep. 10, 2013, in International Application No. PCT/US2012/028484, 10 pgs.
International Search Report and Written Opinion (WO) dated Feb. 2, 2018 in International Application No. PCT/US2017/055618.
International Search Report and Written Opinion (WO) dated Feb. 2, 2018 in International Application No. PCT/US2017/056131.
International Search Report and Written Opinion (WO) dated Feb. 21, 2018 in International Application No. PCT/US2017/056129.
International Search Report and Written Opinion (WO) dated Jan. 17, 2018, in International Application No. PCT/US2017 /045092.
International Search Report and Written Opinion (WO) dated Jan. 31, 2018 in International Application PCT/US2017/056126.
International Search Report and Written Opinion dated Aug. 17, 2018, in International Application No. PCT/US2018/034673.
International Search Report and Written Opinion dated Aug. 2, 2018, in International Application No. PCT/US2018/026074.
International Search Report and Written Opinion dated Jul. 30, 2018, in International Application No. PCT/US2018/026080.
International Search Report and Written Opinion dated Aug. 8, 2016, in International Applicaton No. PCT/US2016/032695, 10 pgs.
International Search Report and Written Opinion dated Feb. 5, 2014, in International Application No. PCT/AU2013/001362, 17 pgs.
International Search Report and Written Opinion dated Jan. 5, 2017, in International Applicaton No. PCT/US2016/058938.
International Search Report and Written Opinion dated Jul. 31, 2014, in International Application No. PCT/US2014/027391, 16 pgs.
International Search Report and Written Opinion dated Oct. 28, 2011, in International No. PCT/AU2011/000987, 18 pgs.
International Search Report dated Aug. 10, 2012, in International Application No. PCT/US2012/028484, 7 pgs.
International Search Report dated Jul. 29, 2014, in International Application No. PCT/AU2014/000478, 7 pgs.
International Search Report dated Sep. 22, 2017, in International Application No. PCT/US2017/040591, 12 pgs.
Irrgang et al., "The historical Development ofMutaflor therapy," Ardeypharm GmbH, pp. 1-38 (1988). <http://www.ardeypharm.de/pdfs/en/mutaflor_historical_e.pdf?>.
Irritable Bowel Syndrome (IBS), Health A to Z, InteliHealth, pp. 1-4, n.d., Web, Oct. 23, 2005 <http://www.intelihealth.com>.
Issa et al., "Clostridium difficile and Inflammatory Bowel Disease," *Inflamm Bowel Dis.*, 14(10):1432-1442 (2008).
Issa et al., "Impact of Clostridium difficile on inflammatory bowel disease," *Clin. Gastroenterol. Hepatol.*, 5(3):345-351 (2007).
Itoh et al., "Characterization of clostridia isolated from faeces of limited flora mice and their effect on caecal size when associated with germ-free mice," *Laboratory Animals*, 19:111-118 (1985).
Itoh et al., "Intestinal bacteria antagonistic to *Clostridium difficile* in mice," *Laboratory Animals*, 21:20-25 (1987).
Ivanov et al., "Specific Microbiota Direct the Differentiation of IL-17-Producing T-Helper Cells in the Mucosa of the Small Intest," *Cell Host & Microbe*, 4:337-349 (2008).
Jacob et al., "Single Delivery of High-Diversity Fecal Microbiota Preparation by Colonoscopy Is Safe and Effective in Increasing Microbial Diversity in Active Ulcerative Colitis," *Inflamm Bowel Dis.*, 0(0):1-9 (2017).
Janeway et al., "Adaptive Immunity to Infection," *Immunobiology*, 6th Edition, Chapter 10, pp. 414 (2005).
Janeway, Jr. et al., "Autoimmune responses are directed against self antigens," *Immunobiology: The Immune System in Health and Disease*, 5th Edition, pp. 1-4 (2001).
Jarvis et al., "National point prevalence of Clostridium difficile in US health care facility inpatients, 2008," *Am. J. Infect. Control*, 37:263-270 (2009).
Johnson et al., "Interruption of Recurrent Clostridium difficile-Associated Diarrhea Episodes by Serial Therapy with Vancomycin and Rifaximin," *Clin. Infect. Dis.*, 44(6):846-848 (2007).
Johnson et al., "Rifaximin Redux: Treatment of recurrent Clostridium difficile infections with Rifaximin immediately post-vancomycin treatment," *Anaerobe*, 15(6):290-291.
Kageyama et al., "Emendation of genus *Collinsella* and proposal of *Collinsella stercoris* sp. nov. and *Collinsella intestinalis* sp. nov.," International Journal of Systematic and Evolutionary Microbiology, 50:1767-1774 (2000).
Kageyama et al., "Phylogenetic and phenotypic evidence for the transfer of Eubacterium aerofaciens to the genus *Collinsella aerofaciens* gen. nov., comb. nov.," International Journal of Systematic Bacteriology, 49:557-565 (1999).
Kakihana et al., "Fecal microbiota transplantation for patients with steriod-resistant acute graft-versus-host disease of the gut," *Blood*, 128(16):2083-2088 (2016).
Kamboj et al., "Relapse versus reinfection: surveillance of Clostridium difficile infection," *Clininfect Dis.*, 53(10):1003-1006 (2011).
Kang et al., "Microbiota Transfer Therapy alters gut ecosystem and improves gastrointestinal and autism symptoms: an open-label study," Microbiome, 5:10, 16 pages (2017).
Karas et al., "A review of mortality due to Clostridium difficile infection," *J Infect.*, 61(1):1-8 (2010).
Kassam et al., "Fecal transplant via rentention enema for refractory or recurrent Clostridium difficile infection," *Arch Intern Med.*, 172(2):191-193 (2012).
Kelly et al., "Commensal gut bacteria: mechanisms of immune modulation," *Trends in Immunology*, 26(6):326-333 (2005).
Kelly et al., "Clostridium difficile—more difficult than ever," *N. Engl. J. Med.*, 359(18):1932-1940 (2008).
Kelly et al., "Clostridium difficile colitis," *N Engl. J Med.*, 330(4):257-62 (1994).
Kelly et al., "Fecal Microbiota Transplant for Treatment of *Clostridium difficile* Infection in Immunocompromised Patients," *Am J Gastroenterol*, 109:1065-1071 (2014).
Kelly et al., "Fecal microbiota transplantatlon for relapsing Clostridium difficile infection in 26 patients: methodology and results," *J Clin. Gastroenterol.*, 46(2):145-149 (2012).
Keynan et al., "The Role of Regulatory T Cells in Chronic and Acute Viral Infections," *Clinical Infectious Diseases*, 46:1046-1052 (2008).
Khanna et al., "A Novel Microbiome Therapeutic Increases Gut Microbial Diversity and Prevents Recurrent Clostridium difficile Infection," The Journal of Infectious Diseases, 214:173-81 (2016).
Khanna et al., "The epidemiology of community-acquired Clostridium difficile infection: a population-based study," *Am J Gastroenterol.*, 107(1):89-95 (2012).
Khanna et al., "The growing incidence and severity of Clostridium difficile infection in inpatient and outpatient settings," *Expert Rev Gastroenterol Hepatol.*, 4(4):409-16 (2010).
Kharidia et al., "The Activity of a Small Lytic Peptide PTP-7 on *Staphylococcus aureus* Biofilms," *J Microbial.*, 49(4):663-668 (2011).
Khomts et al., "Changes in the composition of the human fecal microbiome after bacteriotherapy for recurrent Clostridiurn difficile-associated diarrhea," *J Clin. Gastroenterol.*, 44(5):354-360 (2010).

(56) References Cited

OTHER PUBLICATIONS

Khomts et al., "Therapeutic transplantation of the distal gut microbiota," *Mucosal Immunol.*, 4(1):4-7 (2011).
Kim et al., "Effect of Rifampin on the Plasma Concentration and the Clinical Effect of Haloperidol Concomitantly Administered to Schizophrenic Patients," Journal of Clinical Psychopharmacology, 16(3):247-252 (1996).
Kim et al., "In Vitro Culture Conditions for Maintaining a Complex Population of Human Gastrointestinal Tract Microbiota," Journal of Biomedicine and Biotechnology, 2011(Article ID 838040):1-10 (2011) <http://www.hindawi.com/journals/bmri/2011/838040/>.
Klaenhammer, "Bacteriocins of lactic acid bacteria," Biochimie, 70:337-49 (1988).
Kleiman et al., "Comparison of two coprological methods for the veterinary diagnosis of fasciolosis," *Arquivo Brasileiro de Medicina Veterinaria e Zootccnica*, 55(2):181-185 (2005).
Kobashi et al., "Metabolism of Sennosides by Human Intestinal Bacteria," Journal of Medicinal Plant Research, 40(3):225-236 (1980).
Koch, "What size should a bacterium be? A question of scale," Annu. Rev. Microbial., 50:317-48 (1996).
Krogius-Kurikka et al., "Sequence analysis of percent G+C fraction libraries of human faecal bacterial DNA reveals a high number of *Antinobacteria,*" *BMC Microbiology*, 9(68):1-13 (2009).
Kuijper et al. "Update of Clostridium difficile Infection due to PCR Ribotype 027 in Europe, 2008," *Euro. Surveill.*, 13(31):Article 5 (2008).
Kuksal et al., "Formulation and In Vitro, In Vivo Evaluation of Extended-release Matrix Tablet of Zidovudine: Influence of Combination of Hydrophilic and Hydrophobic Matrix Formers," *AAPS Pharm.*, 7(1):E1-E9 (2006).
Kunde et al., "Safety, Tolerability, and Clinical Response After Fecal Transplantation in Children and Young Adults With Ulcerative Colitis," *JPNG*, 56(6):597-601 (2013).
Kyne et al., "Association between antibody response to toxin A and protection against recurrent Clostridium difficile diarrhea," *Lancet*, 357(9251):189-93 (2001).
Kyne et al., "Asymptomatic carriage of Clostridium difficile and serum levels of IgG antibody against toxin A," *N Engl J Med.*, 342(6):390-397 (2000).
Kyne et al., "Factors associated with prolonged symptoms and severe disease due to Clostridium difficile," *Age and Ageing*, 28(2):107-13 (1999).
Kysela et al., "Serial analysis of V6 ribosomal sequence tags (SARST-V6): a method for efficient, high-throughput analysis of microbial community composition," *Environmental Microbiology.* 7(3):356-364 (2005).
Labbe et al., "Clostridium difficile infections in a Canadian tertiary care hospital before and during a regional epidemic associated with the BI/NAPI/027 strain," *Antimicrob Agents Chemother.*, 52(9):3180-7 (2008).
Lamontagne et al., "Impact of emergency colectomy on survival of patients with fulminant Clostridium difficile colitis during an epidemic caused by a hypervirulent strain," *Ann. Surg.*, 245(2):267-272 (2007).
Larsen et al., "Gut Microbiota in Human Adults with Type 2 Diabetes Differs from Non-Diabetic Adults," PLoS One, 5(2): e9085-e9095 (2010).
Lau et al., "Bacteraemia caused by *Anaerotruncus colihominis*and amended description of the species," *JClin Pathol*, 59:748-752 (2006).
Lawson et al.,"*Anaerotuncus colihominis* gen. nov., sp. nova, from human faeces," *International Journal of Systematic and Evolutionary Microbiology*, 54:413-417 (2004).
Lawson et al., "Anaerotruncus," *Bergey's Manual of Systematics of Archae and Bacteria*, pp. 1-4 (2009).
Lee et al., "Prioritizing candidate disease genes by network-based boosting of genome-wise association data," Genome Research, 21(1):1109-1121 (2011).
Lee et al., "The outcome and long-term follow-up of 94 patients with recurrent and refractory *Clostridium difficile* infection using single to multiple fecal microbiota transplantation vie retention enema," *European Journal Clinical Microbiology Infect Dis.*, 33:1425-1428 (2014).
Lee, "A Prospective Randomized Multi-Centre Trial of Fresh vs. Frozen-and-Thawed Human Biotherapy (Fecal Transplant) for Recurrent Clostridium difficile Infection," U.S. National Institutes of Health, Clinical Study No. NCT01398969, pp. 1-4, last updated Feb. 27, 2014, Web, May 20, 2014 <http://clinicaltrials.gov/ct2/show/NCT01398969>.
Leis et al., "Fecal microbiota transplantation: A 'How-To' guides for nurses," *Collegian*, 22:445-451 (2015).
Leslie et al., "Trehalose and Sucrose Protect Both Membranes and Proteins in Intact Bacteria During Drying," Applied and Environmental Microbiology, 61:3592-3597 (1995).
Lewis et al., "Stool form scale as a useful guide to intestinal transit time," *Scand. J Gastroenterol.*, 32(9):920-924 (1997).
Let et al., "Ecological and evolutionary forces shaping microbial diversity in the human intestine," *Cell*, 124:837-848 (2006).
Ley et al., "Evolution of mammals and their gut microbes," *Science*, 320(5883): 1647-1651 (2008).
Ley et al., "Microbial ecology: human gut microbes associated with obesity," *Nature*, 444(7122):1022-3 (2006).
Ley et al., "Worlds within worlds: evolution of the vertebrate gut microbiota," *Nat. Rev. Microbial.*, 6(10):776-788 (2008).
Lin et al., "Twelve Week Storage Trial of Microbial Viability in Lyophilized and Frozen Fecal Microbiota Preparations," Poster Presentation—Digestive Disease Week 2015, Washington, D.C. USA.
Longstreth, "Irritable bowel syndrome: A multibillion-dollar problem," Gastroenterology, 109(6):2029-2031 (1995).
Loo et al., "A predominantly clonal multi institutional outbreak of Clostridium difficile-associated diarrhea with high morbidity and mortality," *N Engl J Med*, 353(23):2442-9 (2005).
Loo et al., "Host and pathogen factors for Clostridium difficile infection and colonization," *N Engl J Med*, 365(18):1693-703 (2011).
Louie et al., "Fidaxomicin versus vancomycin for Clostridium difficile infection," *N Engl. J. Med.*, 364(5):422-431 (2011).
Louie et al., "Home-based fecal flora infusion to arrest multiply-recurrent C. difficile infection," ICAAC/IDSA Conference, Abstract #K-4201 (2008).
Louis et al., "Diversity, metabolism and microbial ecology of butyrate-producing bacteria from the human large instestine," *FEMS Microbiology Letters*, 294:1-8 (2009).
Lu, "Taboo transplant: How new poo defeats superbugs," Science News, 1:90-91 (2011).
Ludwig et al., "Taxonomic outline of the phylumFirmicutes," Bergey's Manual of Systematic Bacteriology, 3:15-17 (2009).
Lund-Tonnesen et al., "Clostridium difficile-associated diarrhea treated with homologous faeces," *Tidsskr Nor Lageforen*, 118:1027-1030 (1998).
MacConnachie et al., "Faecal transplant for recurrent Clostridium difficile-associated diarrhoea: a UK case series," *QJM*, 102(11):781-784 (2009).
MacDonald et al., "Formation of Ursodeoxycholic Acid from Chenodeoxycholic Acid by a 7b-Hydroxysteroid Dehydrogenase-Elaborating Eubacterium aerofaciens Strain Cocultured with 7a-Hydroxysteroid Dehydrogenase-Elaborating Organisms," Applied and Environmental Microbiology, 44(5):1187-1195 (1982).
Macpherson et al., "Induction of Protective IgA by Intestinal Dendritic Cells Carrying Commensal Bacteria," *Science*, 303:1662-1665 (2004).
Madsen, "The use of probiotics in gastrointestinal disease," Can J Gastroenterol, 15(12):817-22 (2001).
Maizels et al., "Regulatory T cells in Infection," *Advances in Immunology*, Chapter 3, 112:73-136 (2011).
Manichanh et al., "Reshaping the gut microbiome with bacterial transplantation and antibiotic intake," Genome Research20:1411-1419 (2010).
Marchesi et al., "The normal intestinal microbiota," *Curr. Opin. Infect. Dis.*, 20(5):508-513 (2007).

(56) References Cited

OTHER PUBLICATIONS

Martin, "Development and Delivery of a Treatment for Clostridium difficile," *Bacteriotherapy*, pp. 1-2, n.d., Web, Feb. 10, 2012 <www.bacteriotherapy.org>.
Martin-Dejardin et al., "A way to follow the viability of encapsulated Bifidobacterium bifidum subjected to a freeze-drying process in order to target the colon: Interest of flow cytometry," European Journal of Pharmaceutical Sciences, 49:166-74 (2013).
Maslowski et al., "Diet, gut microbiota and immune responses," *Nat Immunol.*, 12(1):5-9 (2011).
McDonald et al., "An Epidemic, Toxin Gene-Variant Strain of Clostridium difficile," *N Engl J Med.*, 353(23):2433-41 (2005).
McDonald et al., "Clostridium difficile Infection in Patients Discharged from US Short-stay Hospitals, 1996-2003" *Emerg. Infect. Dis*, 12(3):409-415 (2006).
McFarland et al., "Breaking the Cycle: Treatment Strategies for 163 Cases of Recurrent Clostridium difficile Disease," *Am. J. Gastroenterol.*, 97(7):1769-1775 (2002).
McFarland et al., "Implications of the changing face of Clostridium difficile disease for health care practitioners," *Am J Infect Control.*, 35(4):237-253 (2007).
McFarland et al., "meta-Analysis of Probiotics for the Prevention of Antibiotic Associated Diarrhea and the Treatment of Clostridium difficile Disease," *Am J Gastroenterol.*, 101(4):812-22 (2006).
McFarland et al., "Nosocomial Acquisition of Clostridium Difficile Infection," *N Engl J Med.*, 320(4):204-210 (1989).
McFarland et al., "Recurrent Clostridium Difficile Disease: Epidemiology and Clinical Characteristics," *Infect Control Hosp Epidemiol.*, 20(1):43-50 (1999).
McFarland et al., "Renewed interest in a difficult disease: Clostridium difficile infections—epidemiology and current treatment strategies," *Curr Opin Gastroenterol.*, 25(1):24-35 (2008).
Miller et al., "Health care-associated Clostridium difficile infection in Canada: patient age and infecting strain type are highly predictive of severe outcome and mortality," Clin Infect Dis., 50(2):194-201 (2010).
Miller et al., "Long-term follow-up of patients with fulminant Clostridium difficile colitis," *J Gastrointest. Surg.*, 13(5):956-959 (2009).
Miller et al., "Morbidity, mortality, and healthcare burden of nosocomial Clostridium difficile-associated diarrhea in Canadian hospitals," *Infect Control Hosp Epidemiol.*, 23(3):137-40 (2002).
Miller, "The fascination with probiotics for Clostridium difficile infection: lack of evidence for prophylactic or therapeutic efficacy," *ANaerobe*, 15(6):281-284 (2009).
Moayyedi et al., "Fecal Microbiota Transplantation Induces Remission in Patients With Active Ulcerative Colitis in a Randomized Controlled Trial," Gastroenterology, 149(1):102-9 (2015).
Molecular Studies in Autism, 2004 Funding Cycle, Cure Autism Now, Cure AUtism Now Foundation, pp. 1-7 (2005) <www.cureautismnow.org>.
Momose et al., "16S rRNA gene sequence-based analysis of clostridia related to conversion of germfree mice to the normal state," *Journal of Applied Microbiology*, 107:2088-2097 (2009).
Morris et al., "Clostridium difficile Colitis: An Increasingly Aggressive Iatrogenic Disease?" *Arch Surg.*, 137(10):1096-1100 (2002).
Mucosal immunity: homeostasis (WS-064): Chairpersons: Toshiaki Ohteki, Makoto Iwata, *International Immunology*, 22:Suppl 1 Pt. 3, 1-9 (2010).
Mullard, "Microbiology: The Inside Story," *Nature*, 453:578-580 (2008).
Murai et al., "Interleukin 10 acts on regulatory T cells to maintain expression of the transcription factor Foxp3 and suppressive function in mice with colitis," *Nat Immunol.*, pp. 1-20 (2009).
Mutaflor, "Brief Summary of Therapeutic Principles," Ardeypharm GmbH 0796 D-58313 Herdecke Germany, 6 pgs (2006).
Mutaflor, "For Functional and Inflammatory Bowel Diseases for Extraintestinal Manifestations for Activation of the Body's In-Built Defences," Ardeypharm GmbH 0796, D-58313 Herdecke Germany, 8 pgs (2006).
Mutaflor, "Safety of Therapy," Ardeypharm GmbH 0796, D-58313 Herdecke Germany, 4 pgs. (1988).
Muto et al., "A Large Outbreak of Clostridium difficile-Associated Disease with an Unexpected Proportion of Deaths and Colectomies at a Teaching Hospital Following Increased Fluoroquinolone Use," *Infect Control Hosp Epidemiol.*, 26(3):273-80 (2005).
Nieuwdorp et al., ["Treatment of recurrent Clostridium difficile-associated diarrhoea with a suspension of donor faeces"], *Ned Tijdschr Geneskd*, 152(35):1927-32 (2008). (English abstract).
Niu et al., "Prevalence and Impact of Bacteriophages on the Prescense of *Escherichia coli* O157:H7 in Feedlot Cattle and Their Environment," Applied and Environmental Microbiology, 75(5):1271-8 (2009).
O'Hara et al., "The gut flora as a forgotten organ," *EMBO Rep.*, 7(7):688-693 (2006).
O'Brien et al., "The emerging infectious challenge of clostridium difficile-associated disease in Massachusetts hospitals: clinical and economic consequences," Infect Control Hosp Epidemiol., 28(11):1219-27 (2007).
O'Connor et al., "clostridium difficile Infection Caused by the Epidemic BI/NAPI/027 Strain," *Gastroenterology*, 136(6):1913-1924 (2009).
Office Action dated Sep. 18, 2015, in European Patent Application No. 11 728 077.6.
O'Garra et al., "IL-10-producing and naturally occurring CD4+ Tregs: limiting collateral damage," *The Journal of Clinical Investigation*, 114:1372-1378 (2004).
O'Hara et al., "Functional modulation of human intestinal epithelial cell responses by Bifidobacterium infantis and Lactobacillus salivarius," *Immunology* 118:202-215 (2006).
Okada et al., "Effects of Fecal Microorganisms and Their Chloroform-Resistant Variants Derived from Mice, Rats, and Humans on Immunological and Physiological Characteristics of the Intestines ofExgerrnfree Mice," *Infection and Immunity*, 62(12):5442-5446 (1994).
Olson et al., "The Gut Microbiota Mediates the Anti-Seizure Effects of the Ketogenic Diet" Cell, 173:1728-1741 (2018) <https://linkinghub.elsevier.com/retrieve/pii/S0092867418305208>.
Ott et al., "Efficacy of Sterile Fecal Filtrate Transfer for Treating Patients With Clostridium difficile Infection," Gastroenterology, 152(4):799-811 (2017).
Paramsothy et al., "Gastroenterologist perceptions of faecal microbiota transplantation," *World J Gastroenterol*, 21(38): 10907-10914 (2015).
Paramsothy et al., "Multidonor intensive faecal microbiota transplantation for active ulcerative colitis: a randomised placebo-controlled trial," The Lancet, published online, 11 pages (2017).
Paterson et al., "Putting back the bugs: Bacterial treatment relieves chronic diarrhoea," *Med J Aus*, 160:232-233 (1994).
Patterson et al., "Special organism isolation: attempting to bridge the gap," *Infect Control Hosp Epidemiol.*, 15(5):335-338 (1994).
Pearce et al., "Modification of the colonic microflora using probiotics: The way forward?," *Gut*, 4l(Suppl 3):A63 (1997).
Pearce et al., "The use of probiotic therapy as a novel approach to the management of irritable bowel syndrome: a preliminary study," *J Gastroenterol & Hepatol*, 12(Suppl):A129 (1997).
Pepin et al., "Clostridium difficile-associated diarrhea in a region of Quebec from 1991 to 2003: a changing pattern of disease severity," *CMAJ*, 171(5):466-472 (2004).
Pepin et al., "Emergence of Fluoroquinolones as the Predominant Risk Factor for Clostridium difficile-Associated Diarrhea: A Cohort Study During an Epidemic in Quebec," *Clin Infect Dis.*, 41(9):1254-1260 (2005).
Pepin et al., "Management and Outcomes of a First Recurrence of Clostridium difficile-Associated Disease in Quebec, Canada," *Clin. Infect. Dis.*, 42:758-764 (2006).
Persky et al., "Treatment of recurrent Clostridium difficile-associated diarrhea by administration of donated stool directly through a colonoscope," *Am J Gastroenterol.*, 95(11):3283-3285 (2000).
Petrof et al., "Stool substitute transplant therapy for the eradication of Clostridium difficile infection: 'RePOOPulating' the gut," *Microbiome*, 1:3 (2013).
Petrof, "Harnessing the healthy gut microbiota to cure patients with recurrent C. difficile infection," U.S. National Institutes of Health,

(56) References Cited

OTHER PUBLICATIONS

Clinical Study No. NCT01372943, pp. 1-2, last updated Nov. 6, 2013, Web, May 22, 2014 <http://clinicaltrials.gov/ct2/show/NCT01372943>.
Pillai et al., "Probiotics for treatment of Clostridium difficile-associated colitis in adults (Review)," *Cochrane Database Syst Rev.*, (1):CD004611 (2008).
Porter, "Coating of pharmaceutical dosage forms," In D.B. Troy (Ed.), Remington: The Science and Practice of Pharmacy, Chapter 46, pp. 929-938 (2005).
Poster 064-03 presented at the 14th International Congress of Immunology, Aug. 22-27, 2010, in Kyoto (Atarshi et al., Regulation of colonic regulatory T cells by Clostridium species).
Prakash et al., "Colon-targeted delivery of live bacterial cell biotherapeutics including microencapsulated live bacterial cells," *Biologics: Targets & Therapy*, 2(3):355-378 (2008).
Prevention of Sudden Infant Death Syndrome, Healthtouch.com, Thomson Micromedex, pp. 1-4, n.d., Web, Nov. 23, 2005.
Qiu et al., "*Faecalibacterium prausnitzii* upregulates regulatory T cells and anti-inflammatory cytokines in treating TNBS-induced colitis," *Journal of Crohn's and Colitis*, 7:e558-e568 (2013).
Rabeneck et al., "Bleeding and perforation after outpatient colonoscopy and their risk factors in usual clinical practice," *Gastroenterology*, 135(6):1899-1906 (2008).
Rager et al., "Evaluation of rumen transfaunation after surgical correction of left-sided displacement of the abomasum in cows," *J Am. Vet. Med. Assoc.*, 225(6):915-920 (2004).
Ramesh et al., "Prevention of Clostridium difficile-induced ileocecitis with Bacteriophage," *Anaerobe*, 5:69-78 (1999).
Rao et al., "Evaluation of gastrointestinal transit in clinical practice: position paper of the American and European Neurogastroenterology and Motility Societies," *Neurogastroenterol. Motil.*, 23(1):8-23 (2011).
Rautava, "Potential uses of probiotics in the neonate," Seminars in Fetal & Neonatal Medicine, 12:45-53 (2007).
Rea et al., "Gut solutions to a gut problem: bacteriocins, probiotics and bacteriophage for control of Clostridium difficile infection," Journal of Medical Microbiology, 62:1369-1378 (2013).
Redelings et al., "Increase in Clostridium difficile-related mortality rates, United States, 1999-2004, " *Emerg Infect Dis.*, 13(9):1417-1419 (2007).
Response to Office Action filed Feb. 25, 2014, in European Patent Application No. 11728077.6.
Response to Office Action filed Jan. 28, 2015, in European Patent Application No. 11728077.6.
Response to Office Action filed Nov. 18, 2015, in European Patent Application No. 11728077.6.
Rex et al., "American College of Gastroenterology guidelines for colorectal cancer screening 2008," *Am. J. Gastroenterol.*, 104(3):739-750 (2009).
Ricciardi et al., "Increasing prevalence and severity of Clostridium difficile colitis in hospitalized patients in the United States," *Arch Surg.*, 142(7):624-631 (2007).
Roberts, Generation and Development Microbial Drug Products, CSO Vedanta Biosciences, 1st Microbiome Drug Development Summit, pp. 1-17 (2016).
Rodemann et al., "Incidence of Clostridium difficile infection in inflammatory bowel disease," *Clin Gastroenterol Hepatol.*, 5(3):339-344 (2007).
Rohlke et al., "Fecal flora reconstitution for recurrent clostridium difficile infection: results and methodology," *J Clin Gastroenterol.*, 44(8):567-570 (2010).
Rolfe et al., "bacterial interference between Clostridium difficile and normal fecal flora," *J Infect Dis.*, 143(3):470-475 (1981).
Rossen et al., "Findings From a Randomized Controlled Trial of Fecal Transplantation for Patients with Ulcerative Colitis," Gastroenterology, 149(1):110-8 (2015).
Round et al., "Inducible Foxp3+ regulatory T-cell development by a commensal bacterium of the intestinal microbiota," *PNAS*, 107(27):12204-12209 (2010).
Round et al., "The gut microbiota shapes intestinal immune responses during health and disease," *Nat. Rev. Immunol.*, 9(5):313-323 (2009).
Rupnik et al., "Clostridium difficile infection: new developments in epidemiology and pathogenesis," *nat. Rev. Microbial.*, 7(7):526-36 (2009).
Russell et al., "Fecal bacteriotherapy for relapsing Clostridium difficile infection in a child: a proposed treatment protocol," *Pediatrics*, 126(1):e239-42 (2010).
Sambol et al., "Colonization for the prevention of *Clostridium difficile* disease in hamsters," *J Infect. Dis.*, 186(12):1781-1789 (2002).
Sanchez et al., "The Role of Natural Regulatory T cells in Infection," *Immunol res.*, 49(0):124-134 (2011).
Sandler et al., "Possible Gut-Brain Interaction Contributing to Delayed Onset Autism Symptomatology," Fourth Int. Symp. Brain-Gut Interactions, Blackwell Science Ltd., 10(4):33 (1998).
Sandler et al., "Short-Term Benefit From Oral Vancomycin Treatment of Regressive-Onset Autism," Journal of Child Neurology, 15(7):429-435 (2000).
Sartor, "Therapeutic correction of bacterial dysbiosis discovered by molecular techniques," *PNAS*, 105(43):16413-16414 (2008).
Schiller, Review article, "the therapy of constipation," Ailment Pharmacol. Ther., 15:749-763 (2001).
Schloss, "Introducing mothur: Open-Source, Platform-Independent, Community-Supported Software for Describing and Comparing Microbial Communities," *Appl. Environ. Microbial.*, 75(23):7537-7541 (2009).
Schwan et al., "Relapsing *Clostridium difficile* Enterocolitis Cured by Rectal Infusion of Homologous Faeces," *The Lancet*, 322(8354):845 (1983).
Schwan et al., "Relapsing *Clostridium difficile* Enterocolitis Cured by Rectal Infusion of Normal Faeces," *Scand. J Infect. Dis.*, 16(2):211-215 (1984).
Seeff et al., "How many endoscopies are performed for colorectal cancer screening? Results from CDC's survey of endoscopic capacity," *Gastroenterology*, 127:1670-1677 (2004).
Sekirov et al., "Gut microbiota in health and disease," *Physiol. Rev.*, 90(3):859-904.
Sell et al., "Bacteriophage and Bacteriocin Typing Scheme for Clostridium difficile," Journal of Clinical Microbiology, 17(6):1148-1152 (1983).
Setlow, "I Will Survive: Protecting and Reparing Spore DNA," Journal of Bacteriology, 174(9):2737-2741 (1992).
Setlow, "The bacterial spore: nature's survival package," Culture, 26(2):1-4 (2005).
Sghir et al., "Quantification of Bacterial Groups within Human Fecal Flora by Oligonucleotide Prode Hybridization," *Applied and Environmental Microbiology*, 66(5):2263-2266 (2000).
Shi et al., "Fecal Microbiota Transplantation for Ulcerative Colitis: A Systematic Review and Meta-Analysis," PLOS One, 1-18 (2016).
Shim et al., "Primary symptomless colonisation by *Clostridium difficile* and decreased risk of subsequent diarrhea," *The Lancet*, 251(9103):633-666 (1998).
Silverman et al., "Success of self-administered home fecal transplantation for chronic Clostridium difficile infection," *Clin. Gastoenterol. Hepatol.*, 8(5):471-473 (2010).
Simor et al., "Clostridium difficile in long-term-care facilities for the elderly," *Infect Control Hosp Epidemiol.*, 23(11):696-703 (2002).
Singhet al., "Do NSAIDs, antibiotics, infections, or stress trigger flares in IBD?" *Am J Gastroenterol.*, 104(5):1298-1313 (2009).
Sleator, "The human superorganism—of microbes and men," *Med. Hypotheses*, 74(2):214-215 (2010).
Smits et al., "Therapeutic potential of fecal microbiota transplantation," Gastroenterology, 145:946-953 (2013).
Sokol et al., *Faecalibacterium prausnitzii* is an anti-inflammatory commensal bacterium identified by gut microbiota analysis of Crohn disease patients, *Proceedings of the National Academy of Sciences*, 105(43):16731-16736 (2008).
Sokol et al., "Low Counts of *Faecalibacterium prausnitzii* in Colitis Microbiota," *Inflamm. Bowel Dis.*, pp. 1-7 (2009).
Sullivan et al., "Effect of supplement with lactic-acid producing bacteria on fatigue and physical activity inpatients with chronic fatigue syndrome," Nutritional Journal, 8(4):1-6 (2009).

(56) References Cited

OTHER PUBLICATIONS

Sunil et al., "Design and evaluation of lomoxicam bilayered tablets for biphasic release," Brazilian Journal of Pharmaceutical Sciences, 48(4):609-19 (2012).
Surawicz et al., "Treatment of refractory and recurrent Clostridium difficile infection," Nat. Rev. Gastroenterol. Hepatol., 8(6):330-339 (2011).
Surawicz, "Reining in Recurrent Clostridium difficile Infection—Who's at Risk?," Gastroenterology, 136:1152-1154 (2009).
Sutherland et al., "Lyophilized Clostridium perfringens 3 alpha- and Clostridium bifermentans 7 alpha-hydroxysteroid dehydrogenases: two new stable enzyme preparations for routine bile acide analysis," Biochim Biophys Acta, 962(1):116-121 (1988).
Takaishi et al., "Imbalance in intestinal microflora constitution could be involved in the pathogenesis of inflammatory bowel disease," J. Med. Microbial., 298:463-472 (2008).
Takedad et al., "Serum Haloperidol Levels of Schizophrenics Receiving Treatment for Tuberculosis," Clinical Neuropharmacology, 9(4):386-397 (1986).
Tannock et al., "A new macrocyclic antibiotic, fidaxomicin (OPT-80), causes less alteration to the bowel microbiota of Clostridium difficile-infected patients than does vancomycin," Microbiology, 156(11):3354-3359 (2010).
Tanoue et al., "Immune response to gut microbiota-commensals and pathogens," Gut Microbes, 1(4):224-233 (2010).
Taras et al., "Reclassification fo Eubacterium formicigenerans Holdeman and Moore 1974 as *Dorea formicigenerans* gen. nov., comb. nov., and description of*Dorea longicatena* sp. nov., isolated from human faeces," International Journal of Systematic.
Teasley et al., "Prospective randomised trial of metronidazole versus vancomycin for Clostridium-difficile-associated diarrhoea and colitis," The Lancet, 2(8358):1043-1046 (1983).
Tian et al., "Freeze-dried, Capsulized Fecal Microbiota Transplantation for Relapsing Clostridium difficile Infection," Journal of Clinical Gastroenterology, 49(6):537-538 (2015).
Tilg et al., "Gut microbiome, obesity, and metabolic dysfunction," J Clin. Invest., 121(6):2126-2132 (2011).
Tvede et al., "Bacteriotherapy for chronic relapsing Clostridium difficile diarrhea in six patients," The Lancet, 1:1156-1160 (1989).
Van Andel et al., "Interleukin-12 Has a Role in Mediating Resistance of Murine Strains to Tyzzer's Disease," Infect. Immun., 66(10):4942-4946 (1998).
Van der Waaij et al., "Direct Flow Cytometry of Anaerobic Bacteria in Human Feces," Cytometry, 16:270-279 (1994).
Van Immerseel et al., "Butyric acid-producing anaerobic bacteria as a novel probiotic treatment approach for inflammatory bowel disease," Journal of Medical Microbiology, 59:141-143 (2010).
Van Nood et al., "Struggling with Recurrent Clostridium difficile Infections: Is Donor Faeces the Solution?," Euro Surveill., 14(34):1-6 (2009).
Van Nood, "Duodenal infusion of donor feces for recurrent Clostridium difficile," New England Journal of Medicine, 368(5):407-415 (2013).
Vaughn et al., "Novel treatment options for ulcerative colitis," Future Science, 1-20 (2013).
Veldhuyzen van Zanten et al., "Drug Treatment of Functional Dyspepsia: A Systematic Analysis of Trial Methodology with Recommendations for Design of Future Trials," Am. J Gastroenterol., 91(4):660-673 (1996).
Veldhuyzen van Zanten et al., "Validation of a 7-point Global Overall Symptom scale to measure the severity of dyspepsia symptoms in clinical trials," Ailment Pharmacol. Ther., 23(4):521-529 (2006).
Venugopal et al., "Fidaxomicin: A Novel Macrocyclic Antibiotic Approved for Treatment of Clostridium difficile Infection," Clin Infect Dis, 54(4):568-74 (2012).
Vrieze et al., "The environment within: how gut microbiota may influence metabolism and body composition," Diabetologia, 53(4):606-613 (2010).
Vulevic et al., "Modulation of the fecal microflora profile and immune function by a novel trans-galactooligosaccharide mixture (B-GOD) in healthy elderly volunteers," Am J Clin Nutr, 88:1438-46 (2008).
Wachsmann et al., "Characterization of an Orotic Acid Fermenting Bacterium, Zymobacterium oroticum, nov. gen., nov. spec.," Journal of Bacteriology, 68(4):400-404 (1954).
Walter et al., "Host-microbial symbiosis in the vertebrate gastrointestinal tract and the Lactobaillus reuteri paradigm," PNAS USA, 108(Suppl 1):4645-4652 (2011).
Warny et al., "Toxin production by an emerging strain of Clostridium difficile associated with outbreaks of severe disease in North America and Europe," Lancet, 366(9491):1079-84 (2005).
Warren et al., "*Clostridium aldenense* sp. nov. and *Clostridium citroniae* sp. nov. Isolated from Human Clinical Infections," Journal of Clinical Microbiology, 44(7):2416-2422 (2006).
Wasfy et al., "Comparison of Preservation Media for Storage of Stool Samples," Journal of Clinical MIcrobiology, 33(8):2176-2178 (1995).
Weingarden et al., "Dynamic changes in short- and long-term bacterial composition following fecal microbiota transplantation for recurrent Clostridium difficile infection," Microbiome, 3(10), 8 pages (2015).
Weissman et al., "Stool Transplants: Ready for Prime Time?," Current Gastroenterology Reports, 14:313-316 (2012).
Wells et al., "Clostridia: Sporeforming Anaerobic Bacilli," medical Microbiology—NCBI Bookshelf4th Edition, Chapter 18, pp. 1-20 (1996) <https://www.ncbi.nlm.nih.gov/books/NBK8219/?report=printable>.
Wenisch et al., "Comparison of Vancomycin, Teicoplanin, Metronidazole, and Fusidic Acid for the Treatment of Clostridium difficile-Associated Diarrhea," Clin Infect Dis., 22(5):813-818 (1996).
Wettstein et al., "Fecal bacteriotherapy—An effective treatment for Relapsing Symptomatic Clostridium difficile Infection," Abstract, 15th United European Gastroenterology Week (UEGW) Poster presentations, United European Gastroenterology Federation, France, A303 (2007).
Wettstein et al., "Skewered diverticulum: another cause of abdominal pain," Internal MedJ, 31(8):495-496 (2001).
Wikoff et al., "Metabolomics analysis reveals large effects of gut microflora on mammalian blood metabolites," PNAS, 106(10):3698-3703 (2009).
Wilson et al., "Human Colonic Biota Studied by Ribosomal DNA Sequence Analysis," Appl. Environ. Microbial., 62(7):2273-2278 (1996).
Yoon et al., "Treatment of Refractory/Recurrent C. difficile-associated Disease by Donated Stool Transplanted Via Colonoscopy: A Case Series of 12 patients," J Clin Gastroenterol., 44(8):562-566 (2010).
You et al., "Successful treatment of fulminant Clostridium difficile infection with fecal bacteriotherapy," Ann. Intern. Med., 148(8):632-633 (2008).
Youngster et al., "Oral, Capsulized, Frozen Microbiota Transplantation for Relapsing Clostridium difficile Infection," American Medical Association, 312 (174) 1772-1778 (2014).
Yue et al., "Similarity Measure Based on Species Proportions," Common. Stat. Theor. Methods, 34(11):2123-2131 (2005).
Zar et al., "A Comparison of Vancomycin and Metronidazole for the Treatment of Clostridium difficile-Associated Diarrhea, Stratified by Disease Severity," Clin Infect Dis., 45(3):302-307 (2007).
Zhang et al, "Influence of Microbiota on Intestinal Immune System in Ulcerative Colitis and Its Intervention," Frontiers in Immunology, 8(Article 1674):1-11 (2017).
Zhang et al., "Altered gut microbiome composition in children with refractory epilepsy after ketogenic diet," Epilepsy Research (2018) <https://doi.org/10.1016/j.eplepsyres.2018.06.15>.
Zhou et al., "Total fecal microbiota transplantation alleviates high-fat diet-induced steatohepatitis in mice via beneficial regulation of gut microbiota," Scientific Reports (Nature), 7(1529):1-11 (2017).
Zilberberg et al., "Clostridium difficile Infections among Hospitalized Children," Emerg. Infect. Dis, 16(4):604-609 (2010).
Zilberberg et al., "Clostridium difficile-related Hospitalizations among US Adults," Emerg. Infect. Dis, 15(1):122-124 (2009).

(56) References Cited

OTHER PUBLICATIONS

Zilberbert et al., "Increase in Adult Clostridium difficile-related Hospitalization and Case-Fatality Rate," Emerg. Infect. Dis, 14(6):929-931 (2008).

Zilberberg et al., "Increase in Clostridium difficile-related Hospitalizations Amoung Infants in the United States, 2001-2005" Pediatr Infect Dis. J, 27(12):1111-1113 (2008).

Zoppi et al., "Oral Bacteriotherapy in Clinical Practice," Eur J. Pediatr, 139(1):18-21 (1982).

Zoppi et al., "The Intenstinal Ecosystem in Chronic Functional Constipation," ACTA Paediatr, 836-841 (1998).

Zuhua et al., "Lyophilization of Ecological Products and Application of Protective Agents," Chinese Journal of Microecology, vol. 9, No. 6 (1997) (electronic).

\* cited by examiner

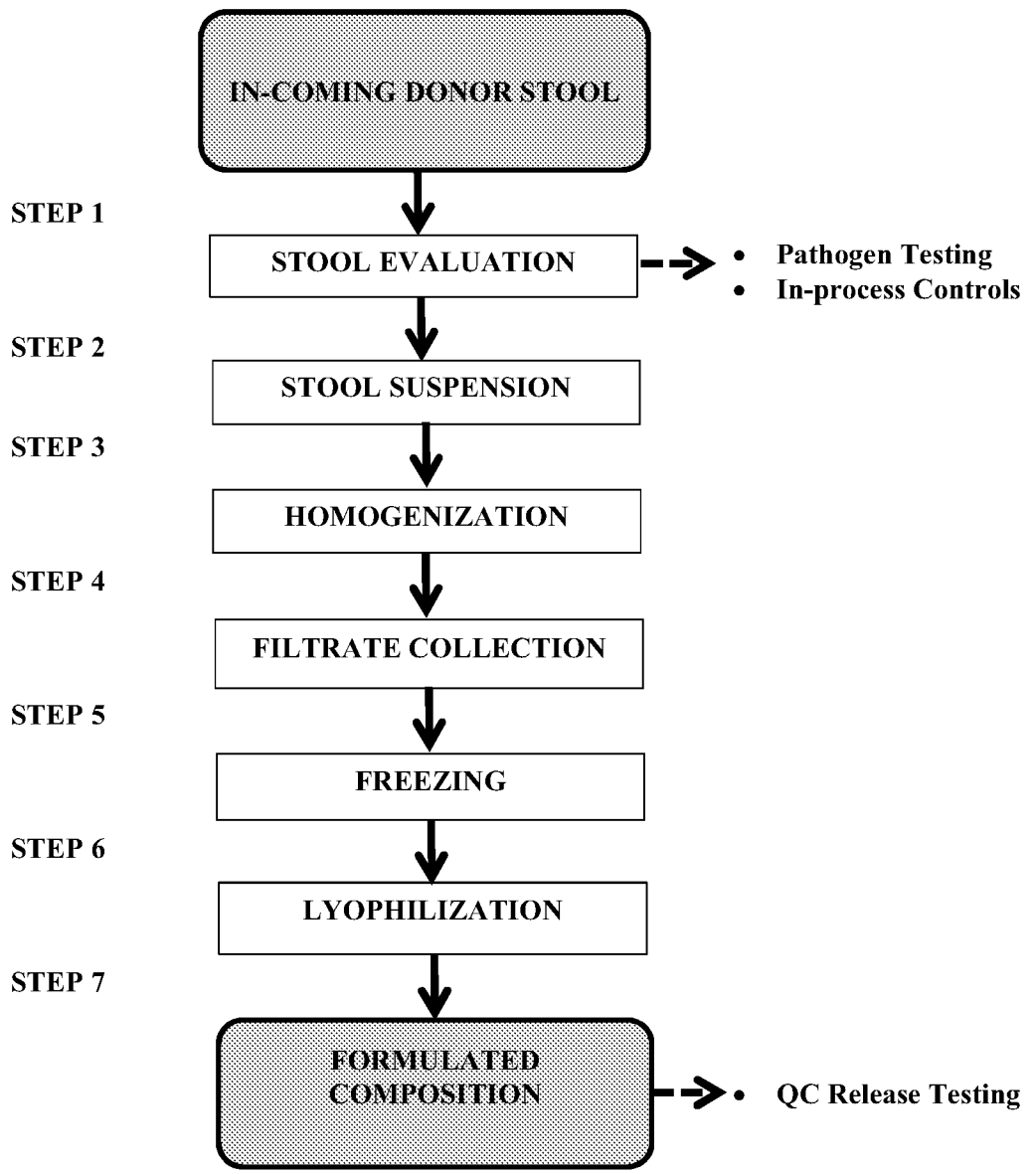

LYOPHILIZED COMPOSITIONS COMPRISING FECAL MICROBE-BASED THERAPEUTIC AGENTS AND METHODS FOR MAKING AND USING SAME

CROSS-REFERENCE TO RELATED APPLICATION

This application is a U.S. National Stage of International Application No. PCT/US2018/034673, filed May 25, 2018, which claims priority to U.S. Provisional Application No. 62/511,776, filed May 26, 2017, both of which are incorporated by reference herein in its entirety.

TECHNICAL FIELD

This disclosure generally relates to medicine and gastroenterology, pharmacology and microbiology. In one aspect, compositions provided herein are used for the stabilization, amelioration, treatment and/or prevention of constipation, for the treatment of abdominal pain, particularly non-specific abdominal pain, and diarrhea, including diarrhea caused by a drug side effect, a psychological condition, a disease or a condition such as autism, Crohn's Disease, a poison, a toxin or an infection, e.g., a toxin-mediated traveller's diarrhea, or *C. difficile* or the pseudo-membranous colitis associated with this infection. In one aspect, pharmaceuticals and products (articles) of manufacture provided herein are delivered to an individual, e.g., a human or an animal, in need thereof.

BACKGROUND

Implantation or administration of human colonic microbiota into the bowel of a sick patient is often referenced as Fecal Microbiota Transplantation (FMT). It is a therapeutic process originally designed to treat *Clostridium difficile* infection (CDI) and others. It entails infusions through a colonoscope, an enema or via a nasojejunal tube of human microbiota either in the form of homogenized stool, extracts of homogenized stool, or cultured stool components such as Clostridia, to implant in the colon and so displace or eradicate the pathogenic *Clostridium difficile*; and it has a high success rate. In treating *C. difficile* infection, FMT is a highly efficacious treatment which carries well over a 90% cure rate with a single infusion and higher rate with multiple infusions. Hence, FMT can be life-saving given the current CDI mortality in the US of some 30,000 persons/year. Such a therapeutic process has also been used in treating other gut infective agents such as *E. coli* and Vancomycin resistant Enterococci (VRE).

There is growing demand for FMT primarily for the treatment of CDI. However, use of the therapy is restricted by the logistics of obtaining fresh FMT material from pre-screened donors in a timely fashion. Access to pre-prepared FMT material, stored frozen or lyophilized, would improve access to the therapy. Here, Applicant provides, among other uses, the production and use of lyophilized pharmaceutical compositions comprising a lyophilization formulation that uses a cryoprotectant, such as trehalose with or without a reducing agent such as cysteine, sodium ascorbate, or ascorbic acid to preserve microbial cell viability at an unexpectedly high efficiency.

SUMMARY

In one aspect, the present disclosure provides a pharmaceutical composition comprising a lyophilized fecal microbe preparation comprising a lyophilization formulation comprising at least about 12.5% trehalose, wherein the lyophilization formulation is capable of providing a cell integrity maintenance ratio of at least about 20%. In another aspect, a pharmaceutical composition comprises a lyophilization formulation further comprising cysteine selected from the group consisting of D-cysteine and L-cysteine.

In another aspect, the present disclosure provides a lyophilized fecal microbe composition comprising a lyophilization formulation comprising trehalose and cysteine, wherein the lyophilization formulation is capable of maintaining at least about 30% cell viability immediately post lyophilization relative to a pre-lyophilization cell viability.

In one aspect, the present disclosure provides lyophilized fecal microbiota pharmaceutical composition comprising a lyophilization formulation comprising at least about 12.5% trehalose, wherein the lyophilization formulation is capable of providing a cell integrity maintenance ratio of at least 35%.

In one aspect, the present disclosure provides a method of preparing a lyophilized fecal microbe preparation, the method comprising:
a. obtaining a liquid fecal microbe preparation in a lyophilization formulation comprising between 12.5% and 17.5% trehalose; and
b. freeze-drying the liquid fecal microbe preparation, wherein the lyophilization formulation is capable of providing a cell integrity maintenance ratio of at least about 30%.

In another aspect, the present disclosure provides a frozen fecal microbe composition comprising trehalose, wherein the frozen fecal microbe composition is capable of being thawed at least once without loss of microbial cell membrane integrity of more than 50%. In another aspect, a frozen fecal microbe composition further comprises cysteine selected from the group consisting of D-cysteine and L-cysteine.

In another aspect, this disclosure provides a method for treating a disorder or condition in a subject in need thereof, comprising administering to the subject a therapeutically effective amount of a pharmaceutical composition or a previously frozen fecal microbe composition disclosed herein, wherein the disorder or condition is selected from the group consisting of Acne, AIDS Enteropathy, AIDS-related Gastroenteritis, Alopecia Totalis, Alzheimers Disease, Amyloidosis, Amyotrophic Lateral Sclerosis, Ankylosing Spondylitis, Anorexia, Antibiotic Associated Colitis, Asbergers Syndrome, Attention Deficit Disorder (ADD), Attention Deficit Hyperactivity Disorder (ADHD), Autism Spectrum Disorder (ASD), Behcet's Syndrome, Chronic *Clostridium difficile* Infection (CDI), Chronic constipation, Chronic Depression, Chronic Fatigue Syndrome (CFS), Chronic Idiopathic Pseudo Obstructive Syndrome, Chronic Inflammation Demyelinating Polyneuropathy, Chronic Nausea, Chronic Urticaria, Coeliac Disease, Collagenous Colitis, Colonic Polyps, Constipation Predominant FBD, Crohn's Disease, Cryptogenic Cirrhosis, Cyclic Vomiting, Dermatitis Herpetiformis, Diabetes, Familial Mediterranean Fever, Fatty Liver, Functional Bowel Disease (FBD), Gastro-oesophageal Reflux, Gillian-Barre Syndrome, Glomerulonephritis, Haemolytic Uraemic Syndrome, Halitosis, IBS constipation-predominant, IBS diarrhea/constipation alternating, IBS diarrhea-predominant, IBS pain-predominant, Idiopathic Thrombocytopenic Purpura (ITP), Idiopathic/Simple Constipation, Indeterminate Colitis, Inflammatory Bowel Disease (IBD), Irritable bowel syndrome (IBS), Juvenile Diabetes Mellitus, Lyme Disease, Manic Depressive Illness, Metabolic Syndrome, Microscopic Colitis, Migraine, Mixed Cryoglobulinaemia, Mucous Colitis, Multiple Sclerosis, Myasthenia Gravis, NASH (Nonalcoholic Steatohepatitis), Non-Rheumatoid Arthritis, Non-Rheumatoid Factor Positive Arthritis, Non-ulcer Dyspepsia, Norwalk Viral Gastroenteritis, Obesity, Obsessive Compulsive Disorder, Pain Predominant FBD, Parkinson's Disease, Polyarteritis, Polyposis *Coli*, Primary Biliary Cirrhosis, Primary *Clostridium difficile* Infection (CDI), Primary Sclerosing Cholangitis (PSC), Pseudomembranous Colitis, Psychotic Disorders, Reiter's Syndrome, Relapsing Diverticulitis, Rett Syndrome, Rheumatoid Arthritis, Rosacea, Rotavirus Gastroenteritis, Sacroiliitis, Schizophrenia, Scleroderma, Sjogren's Syndome, Small Bowel Bacterial Overgrowth, Sudden Infant Death Syndrome (SIDS), Systemic Lupus Erythematosus, Ulcerative Colitis, Upper Abdominal FBD, Vasculitic Disorders, Viral Gastroenteritis, pre-diabetic syndrome, type I diabetes, type II diabetes, depression, schizophrenia, and a mood disorder.

In another aspect, this disclosure provides a method for treating a disorder or condition in a subject in need thereof, comprising administering to the subject a therapeutically effective amount of a pharmaceutical composition or a previously frozen fecal microbe composition disclosed herein, wherein the disorder or condition is selected from the group consisting of recurrent or primary *C. difficile* infection, autism spectrum disorder (ASD), ulcerative colitis, Crohn's disease, and irritable bowel syndrome.

BRIEF DESCRIPTION OF THE DRAWINGS

FIG. 1. shows a flowchart illustrating an exemplary process for manufacturing a composition described herein.

DETAILED DESCRIPTION

Unless defined otherwise herein, terms are to be understood according to conventional usage by those of ordinary skill in the relevant art.

As used herein, "lyophilization" or "freeze drying" refers to the process of drying a material by first freezing it and then encouraging the ice within it to sublimate in a vacuum environment.

As used herein, a "cell integrity maintenance ratio" is defined as the percentage of microbial cells maintaining integral cell membrane post-lyophilization relative to pre-lyophilization. As used herein, "microbial cell membrane integrity" refers to the actual percent of microbial cells that possess integral cell membrane in a population of microbes. As used herein, a "post-lyophilization cell membrane integrity percentage" refers to the percentage of microbial cells with cell membrane being intact in a lyophilized composition. The "cell integrity maintenance ratio" is based on a comparison between post-lyophilization and pre-lyophilization and thus reflects changes in cell integrity after a lyophilization process. The "microbial cell membrane integrity" and "post-lyophilization cell membrane integrity percentage" reflect the actual percentage of cells that contain integral cell membrane in a composition. Membrane integrity can be measured using a variety of methods including flow cytometry-based method and fluorescence microscope-based method. Cells can be stained with dyes that specifically recognize cells with intact, integral, or compromised membranes. In some instances multiple dyes can be used simultaneously to detect live and dead cells in a population of cells. For example, one aliquot of cells is stained with SYTO™ BC dye (Invitrogen, CA) to stain cells and Prolong Anti-Fade Reagent (Invitrogen, CA) to minimize photobleaching of dye. A second aliquot is stained with another dye, Propidium Iodide (Invitrogen, CA). Whereas the SYTO BC dye penetrates all cells which stain green, the Propidium Iodide (PI) dye only penetrates cells with a loss of membrane integrity (i.e. injured or dead cells), and the PI stained cells appear red when visualized under the epifluorescence microscope using the specific red filter. Details of an exemplary cell staining protocol can be found in Example 2.

As used herein, "viable" means possessing the ability to multiply. Here, the viability of bacterial populations is monitored as a function of the membrane integrity of the cell. Cells with a compromised membrane are considered to be dead or dying (which include injured cells or cells with compromised membrane that are live but unable to divide), whereas cells with an intact membrane are considered live.

As used herein, unless indicated otherwise, percent concentration refers to weight-to-volume percent (% w/v). For example, 15% trehalose refers to a solution which contains 15 g of trehalose per 100 mL of solution.

As used herein, a "cryoprotectant" refers to a substance that is added to a formulation in order to protect an active ingredient during freezing.

As used herein, a "reducing agent" refers to a substance that is added to a formulation in order to bring about reduction by being oxidized. In an aspect of the present disclosure, a reducing agent is selected from the group comprising cysteine, ascorbic acid, sodium ascorbate, thioglycolic acid, sodium sulfite, sodium bisulfate, sodium metabisulfite, potassium metabisulfite, Glutathione, Methionine, thioglycerol, and alpha tocopherol.

As used herein, a "lyoprotectant" refers to a substance that is added to a formulation in order to protect an active ingredient during the drying stage of a lyophilization (also known as freeze-drying) process.

As used herein, a "microbiota" and "flora" refer to a community of microbes that live in or on a subject's body, both sustainably and transiently, including eukaryotes, archaea, bacteria, and viruses (including bacterial viruses (i.e., phage)). A "fecal microbiota" or "fecal microbiota preparation" refers to a community of microbes present in a subject's feces. A non-selected fecal microbiota refers to a community or mixture of fecal microbes derived from a donor's fecal sample without selection and substantially resembling microbial constituents and population structure found in such fecal sample.

As used herein, "colony forming units" (cfu) refers to an estimate of the number of viable microorganism cells in a given sample.

As used herein, "isolated" or "purified" refers to a bacterium or other entity or substance that has been (1) separated from at least some of the components with which it was associated when initially produced (whether in nature or in an experimental setting), and/or (2) produced, prepared, purified, and/or manufactured by the hand of man. Isolated or purified bacteria can be separated from at least about 10%, about 20%, about 30%, about 40%, about 50%, about 60%, about 70%, about 80%, about 90%, about 92%, about 94%, about 96%, about 98%, about 99% or more of the other components with which they were initially associated.

As used herein, the terms "pathogen" and "pathogenic" in reference to a bacterium or any other organism or entity includes any such organism or entity that is capable of causing or affecting a disease, disorder or condition of a host organism containing the organism or entity.

As used herein, "spore" or a population of "spores" includes bacteria (or other single-celled organisms) that are generally viable, more resistant to environmental influences such as heat and bacteriocidal agents than vegetative forms of the same bacteria, and typically capable of germination and out-growth. "Spore-formers" or bacteria "capable of forming spores" are those bacteria containing the genes and other necessary abilities to produce spores under suitable environmental conditions.

As used herein, "subject" refers to any animal subject including humans, laboratory animals (e.g., primates, rats, mice), livestock (e.g., cows, sheep, goats, pigs, turkeys, chickens), and household pets (e.g., dogs, cats, rodents, etc.). The subject or patient may be healthy, or may be suffering from an infection due to a gastrointestinal pathogen or may be at risk of developing or transmitting to others an infection due to a gastrointestinal pathogen.

As used herein, "Shannon Diversity Index" refers to a diversity index that accounts for abundance and evenness of species present in a given community using the formula $H=-\Sigma_{i=1}^{R} p_i \ln p_i$, where H is Shannon Diversity Index, R is the total number of species in the community, and $p_i$ is the proportion of R made up of the ith species. Higher values indicate diverse and equally distributed communities, and a value of 0 indicates only one species is present in a given community. For further reference, see Shannon and Weaver, (1949) The mathematical theory of communication. The University of Illinois Press, Urbana. 117pp.

As used herein, "antibiotic" refers to a substance that is used to treat and/or prevent bacterial infection by killing bacteria, inhibiting the growth of bacteria, or reducing the viability of bacteria.

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures.

As used herein, "therapeutically effective amount" or "pharmaceutically active dose" refers to an amount of a composition which is effective in treating the named disease, disorder or condition.

As used herein, the term "substantially", when used to modify a quality, generally allows certain degree of variation without that quality being lost. For example, in certain aspects such degree of variation can be less than 0.1%, about 0.1%, about 0.2%, about 0.3%, about 0.4%, about 0.5%, about 0.6%, about 0.7%, about 0.8%, about 0.9%, about 1%, between 1-2%, between 2-3%, between 3-4%, between 4-5%, or greater than 5%.

In one aspect, the present disclosure provides a pharmaceutical composition comprising a lyophilized fecal microbe preparation comprising a lyophilization formulation comprising at least about 12.5% trehalose, wherein the lyophilization formulation is capable of providing a cell integrity maintenance ratio of at least about 30%.

In one aspect, a lyophilization formulation comprises at least about 5%, at least about 7.5%, at least about 10%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20%, at least about 22.5%, at least about 25%, at least about 27.5%, at least about 30%, at least about 32.5%, at least about 35%, at least about 37.5%, at least about 40%, at least about 42.5%, at least about 45%, at least about 47.5%, at least about 50%, at least about 52.5%, at least about 55%, at least about 57.5%, or at least about 60% trehalose.

In another aspect, a lyophilization formulation comprises between about 12.5% and about 60%, between about 13% and about 60%, between about 13.5% and about 60%, between about 14% and about 60%, between about 14.5% and about 60%, between about 15% and about 60%, between about 15.5% and about 60%, between about 16% and about 60%, between about 16.5% and about 60%, between about 17% and about 60%, between about 17.5% and about 60%, between about 18% and about 60%, between about 18.5% and about 60%, between about 19% and about 60%, between about 19.5% and about 60%, between about 20% and about 60%, between about 22.5% and about 60%, between about 25% and about 60%, between about 27.5% and about 60%, between about 30% and about 60%, between about 32.5% and about 60%, between about 35% and about 60%, or between about 37.5% and about 60% trehalose.

In one aspect, a lyophilization formulation comprises between about 12.5% and about 40%, between about 13% and about 40%, between about 13.5% and about 40%, between about 14% and about 40%, between about 14.5% and about 40%, between about 15% and about 40%, between about 15.5% and about 40%, between about 16% and about 40%, between about 16.5% and about 40%, between about 17% and about 40%, between about 17.5% and about 40%, between about 18% and about 40%, between about 18.5% and about 40%, between about 19% and about 40%, between about 19.5% and about 40%, between about 20% and about 40%, between about 22.5% and about 40%, between about 25% and about 40%, between about 27.5% and about 40%, between about 30% and about 40%, between about 32.5% and about 40%, between about 35% and about 40%, or between about 37.5% and about 40% trehalose.

In another aspect, a lyophilization formulation comprises between about 12.5% and about 30%, between about 13% and about 30%, between about 13.5% and about 30%, between about 14% and about 30%, between about 14.5% and about 30%, between about 15% and about 30%, between about 15.5% and about 30%, between about 16% and about 30%, between about 16.5% and about 30%, between about 17% and about 30%, between about 17.5% and about 30%, between about 18% and about 30%, between about 18.5% and about 30%, between about 19% and about 30%, between about 19.5% and about 30%, between about 20% and about 30%, between about 22.5% and about 30%, between about 25% and about 30%, or between about 27.5% and about 30% trehalose.

In one aspect, a lyophilization formulation comprises between about 12.5% and about 25%, between about 13% and about 25%, between about 13.5% and about 25%, between about 14% and about 25%, between about 14.5% and about 25%, between about 15% and about 25%, between about 15.5% and about 25%, between about 16% and about 25%, between about 16.5% and about 25%, between about 17% and about 25%, between about 17.5% and about 25%, between about 18% and about 25%, between about 18.5% and about 25%, between about 19% and about 25%, between about 19.5% and about 25%, between about 20% and about 25%, or between about 22.5% and about 25% trehalose.

In another aspect, a lyophilization formulation comprises between about 12.5% and about 20%, between about 13% and about 20%, between about 13.5% and about 20%, between about 14% and about 20%, between about 14.5% and about 20%, between about 15% and about 20%, between about 15.5% and about 20%, between about 16% and about 20%, between about 16.5% and about 20%, between about 17% and about 20%, between about 17.5% and about 20%, between about 18% and about 20%, between about 18.5% and about 20%, between about 19% and about 20%, or between about 19.5% and about 20% trehalose.

In one aspect, a lyophilization formulation comprises between about 12.5% and about 17.5%, between about 13% and about 17.5%, between about 13.5% and about 17.5%, between about 14% and about 17.5%, between about 14.5% and about 17.5%, between about 15% and about 17.5%, between about 15.5% and about 17.5%, between about 16% and about 17.5%, between about 16.5% and about 17.5%, or between about 17% and about 17.5% trehalose.

In another aspect, a lyophilization formulation comprises between about 12.5% and about 17.5%, between about 13% and about 17%, between about 13.5% and about 16.5%, between about 14% and about 16%, or between about 14.5% and about 15.5% trehalose.

In one aspect, a lyophilization formulation comprises about 15% trehalose. In another aspect, a lyophilization formulation comprises 15% trehalose.

In one aspect, a lyophilization formulation is capable of providing a cell integrity maintenance ratio of at least about 25%, at least about 27.5%, at least about 30%, at least about 32.5%, at least about 35%, at least about 37.5%, at least about 40%, at least about 42.5%, at least about 45%, at least about 47.5%, at least about 50%, at least about 52.5%, at least about 55%, at least about 57.5%, at least about 60%, at least about 62.5%, at least about 65%, at least about 67.5%, at least about 70%, at least about 72.5%, at least about 75%, at least about 77.5%, at least about 80%, at least about 82.5%, at least about 85%, at least about 87.5%, at least about 90%, at least about 92.5%, or at least about 95%.

In another aspect, a lyophilization formulation is capable of providing a cell integrity maintenance ratio of between about 32.5% and about 90%, between about 35% and about 90%, between about 37.5% and about 90%, between about 40% and about 90%, between about 42.5% and about 90%, between about 45% and about 90%, between about 47.5% and about 90%, between about 50% and about 90%, between about 52.5% and about 90%, between about 55% and about 90%, between about 57.5% and about 90%, between about 60% and about 90%, between about 62.5% and about 90%, between about 65% and about 90%, between about 67.5% and about 90%, between about 70% and about 90%, between about 72.5% and about 90%, between about 75% and about 90%, between about 77.5% and about 90%, between about 80% and about 90%, between about 82.5% and about 90%, between about 85% and about 90%, or between about 87.5% and about 90%.

In one aspect, a lyophilization formulation is capable of providing a cell integrity maintenance ratio of between about 32.5% and about 80%, between about 35% and about 80%, between about 37.5% and about 80%, between about 40% and about 80%, between about 42.5% and about 80%, between about 45% and about 80%, between about 47.5% and about 80%, between about 50% and about 80%, between about 52.5% and about 80%, between about 55% and about 80%, between about 57.5% and about 80%, between about 60% and about 80%, between about 62.5% and about 80%, between about 65% and about 80%, between about 67.5% and about 80%, between about 70% and about 80%, between about 72.5% and about 80%, between about 75% and about 80%, or between about 77.5% and about 80%.

In another aspect, a lyophilization formulation is capable of providing a cell integrity maintenance ratio of between about 32.5% and about 70%, between about 35% and about 70%, between about 37.5% and about 70%, between about 40% and about 70%, between about 42.5% and about 70%, between about 45% and about 70%, between about 47.5% and about 70%, between about 50% and about 70%, between about 52.5% and about 70%, between about 55% and about 70%, between about 57.5% and about 70%, between about 60% and about 70%, between about 62.5% and about 70%, between about 65% and about 70%, or between about 67.5% and about 70%.

In one aspect, a lyophilization formulation is capable of providing a cell integrity maintenance ratio of between about 32.5% and about 60%, between about 35% and about 60%, between about 37.5% and about 60%, between about 40% and about 60%, between about 42.5% and about 60%, between about 45% and about 60%, between about 47.5% and about 60%, between about 50% and about 60%, between about 52.5% and about 60%, between about 55% and about 60%, or between about 57.5% and about 60%.

In another aspect, a lyophilization formulation is capable of providing a cell integrity maintenance ratio of between about 32.5% and about 50%, between about 35% and about 50%, between about 37.5% and about 50%, between about 40% and about 50%, between about 42.5% and about 50%, between about 45% and about 50%, or between about 47.5% and about 50%.

In one aspect, a lyophilization formulation is capable of providing a cell integrity maintenance ratio of between about 32.5% and about 80%, between about 35% and about 77.5%, between about 37.5% and about 75%, between about 40% and about 67.5%, between about 42.5% and about 65%, between about 45% and about 62.5%, between about 47.5% and about 60%, between about 50% and about 57.5%, or between about 52.5% and about 55%.

In another aspect, a lyophilization formulation is capable of providing a cell integrity maintenance ratio of between about 32.5% and about 90%, between about 35% and about 87.5%, between about 37.5% and about 85%, between about 40% and about 82.5%, between about 42.5% and about 77.5%, between about 45% and about 75%, between about 47.5% and about 72.5%, between about 50% and about 70%, between about 52.5% and about 67.5%, between about 55% and about 65%, or between about 57.5% and about 62.5%.

In one aspect, a lyophilization formulation is capable of providing a post-lyophilization cell membrane integrity percentage of at least about 20%, at least about 22.5%, at least about 25%, at least about 27.5%, at least about 30%, at least about 32.5%, at least about 35%, at least about 37.5%, at least about 40%, at least about 42.5%, at least about 45%, at least about 47.5%, at least about 50%, at least about 52.5%, at least about 55%, at least about 57.5%, at least about 60%, at least about 62.5%, at least about 65%, at least about 67.5%, at least about 70%, at least about 72.5%, at least about 75%, at least about 77.5%, at least about 80%.

In one aspect, a lyophilization formulation is capable of providing a post-lyophilization cell membrane integrity percentage of between about 20% and about 80%, between about 22.5% and about 80%, between about 25% and about 80%, between about 27.5% and about 80%, between about 30% and about 80%, between about 32.5% and about 80%, between about 35% and about 80%, between about 37.5% and about 80%, between about 40% and about 80%, between about 42.5% and about 80%, between about 45% and about 80%, between about 47.5% and about 80%, between about 50% and about 80%, between about 52.5% and about 80%, between about 55% and about 80%, between about 57.5% and about 80%, between about 60% and about 80%, between about 62.5% and about 80%, between about 65% and about 80%, between about 67.5% and about 80%, between about 70% and about 80%, between about 72.5% and about 80%, between about 75% and about 80%, or between about 77.5% and about 80%.

In one aspect, a lyophilization formulation is capable of providing a post-lyophilization cell membrane integrity percentage of between about 20% and about 70%, between about 22.5% and about 70%, between about 25% and about 70%, between about 27.5% and about 70%, between about 30% and about 70%, between about 32.5% and about 70%, between about 35% and about 70%, between about 37.5% and about 70%, between about 40% and about 70%, between about 42.5% and about 70%, between about 45% and about 70%, between about 47.5% and about 70%, between about 50% and about 70%, between about 52.5% and about 70%, between about 55% and about 70%, between about 57.5% and about 70%, between about 60% and about 70%, between about 62.5% and about 70%, between about 65% and about 70%, or between about 67.5% and about 70%.

In one aspect, a lyophilization formulation is capable of providing a post-lyophilization cell membrane integrity percentage of between about 20% and about 60%, between about 22.5% and about 60%, between about 25% and about 60%, between about 27.5% and about 60%, between about 30% and about 60%, between about 32.5% and about 60%, between about 35% and about 60%, between about 37.5% and about 60%, between about 40% and about 60%, between about 42.5% and about 60%, between about 45% and about 60%, between about 47.5% and about 60%, between about 50% and about 60%, between about 52.5% and about 60%, between about 55% and about 60%, or between about 57.5% and about 60%.

In one aspect, a lyophilization formulation is capable of providing a post-lyophilization cell membrane integrity percentage of between about 20% and about 50%, between about 22.5% and about 50%, between about 25% and about 50%, between about 27.5% and about 50%, between about 30% and about 50%, between about 32.5% and about 50%, between about 35% and about 50%, between about 37.5% and about 50%, between about 40% and about 50%, between about 42.5% and about 50%, between about 45% and about 50%, or between about 47.5% and about 50%.

In one aspect, a lyophilization formulation is capable of providing a post-lyophilization cell membrane integrity percentage of between about 20% and about 40%, between about 22.5% and about 40%, between about 25% and about 40%, between about 27.5% and about 40%, between about 30% and about 40%, between about 32.5% and about 40%, between about 35% and about 40%, or between about 37.5% and about 40%.

In one aspect, a lyophilization formulation is capable of providing a post-lyophilization cell membrane integrity percentage of between about 32.5% and about 80%, between about 35% and about 77.5%, between about 37.5% and about 75%, between about 40% and about 67.5%, between about 42.5% and about 65%, between about 45% and about 62.5%, between about 47.5% and about 60%, between about 50% and about 57.5%, or between about 52.5% and about 55%.

In another aspect, a lyophilization formulation is capable of providing a post-lyophilization cell membrane integrity percentage of between about 32.5% and about 90%, between about 35% and about 87.5%, between about 37.5% and about 85%, between about 40% and about 82.5%, between about 42.5% and about 77.5%, between about 45% and about 75%, between about 47.5% and about 72.5%, between about 50% and about 70%, between about 52.5% and about 67.5%, between about 55% and about 65%, or between about 57.5% and about 62.5%.

In one aspect, a lyophilization formulation is capable of providing a post-lyophilization cell membrane integrity percentage of between about 25% and about 55%, between about 27.5% and about 52.5%, between about 30% and about 50%, between about 32.5% and about 47.5%, between about 35% and about 45%, or between about 37.5% and about 42.5%.

In one aspect, a pharmaceutical composition comprises a lyophilization formulation further comprising cysteine selected from the group consisting of D-cysteine and L-cysteine. In another aspect, cysteine is at a concentration of at least about 0.025%. In one aspect, cysteine is at a concentration of about 0.025%. In another aspect, cysteine is at a concentration of 0.025%. In another aspect, another reducing agent other than cysteine is used in lieu of, or in combination with cysteine. In an aspect, another reducing agent is selected from the group comprising ascorbic acid, sodium ascorbate, thioglycolic acid, sodium sulfite, sodium bisulfite, sodium metabisulfite, potassium metabisulfite, Glutathione, Methionine, thioglycerol, and alpha tocopherol. Any cysteine concentration mentioned in this disclosure is equally applicable to any of the foregoing reducing agents. For simplicity, concentration is not repeated. However, in all instances where a cysteine concentration or concentration range is mentioned, any one of the foregoing group of reducing agents is deemed also described with the same concentration or concentration ranges.

In one aspect, cysteine is at a concentration of at least about 0.005%, at least about 0.01%, at least about 0.015%, at least about 0.02%, at least about 0.025%, at least about 0.03%, at least about 0.035%, at least about 0.04%, at least about 0.045%, at least about 0.05%, at least about 0.055%, at least about 0.06%, at least about 0.065%, at least about 0.07%, at least about 0.075%, at least about 0.08%, at least about 0.085%, at least about 0.09%, at least about 0.095%, at least about 0.1%, at least about 0.12%, at least about 0.14%, at least about 0.16%, at least about 0.18%, at least about 0.2%, at least about 0.25%, at least about 0.3%, at least about 0.4%, at least about 0.5%, at least about 0.6%, at least about 0.7%, at least about 0.8%, at least about 0.9%, at least about 1%, at least about 2%, at least about 4%, at least about 6%, at least about 8%, at least about 10%, at least about 12%, at least about 14%, at least about 16%, at least about 18%, at least about 20%, at least about 22%, at least about 24%, or at least about 26%.

In another aspect, cysteine is at a concentration of between about 0.001% and about 0.005%, between about 0.005% and about 0.1%, between about 0.01% and about 0.1%, between about 0.015% and about 0.1%, between about 0.02% and about 0.1%, between about 0.025% and about 0.1%, between about 0.03% and about 0.1%, between about 0.035% and about 0.1%, between about 0.04% and about 0.1%, between about 0.045% and about 0.1%, between about 0.05% and about 0.1%, between about 0.055% and about 0.1%, between about 0.06% and about 0.1%, between about 0.065% and about 0.1%, between about 0.07% and about 0.1%, between about 0.075% and about 0.1%, between about 0.08% and about 0.1%, between about 0.085% and about 0.1%, between about 0.09% and about 0.1%, between about 0.095% and about 0.1%, between about 0.1% and about 0.3%, between about 0.3% and about 0.5%, between about 0.5% and about 0.7%, between about 0.7% and about 0.9%, between about 0.9% and about 1.0%, between about 0.1% and about 1.0%, between about 0.5% and about 1.0%.

In one aspect, cysteine is at a concentration of between about 0.005% and about 0.08%, between about 0.01% and about 0.08%, between about 0.015% and about 0.08%, between about 0.02% and about 0.08%, between about 0.025% and about 0.08%, between about 0.03% and about 0.08%, between about 0.035% and about 0.08%, between about 0.04% and about 0.08%, between about 0.045% and about 0.08%, between about 0.05% and about 0.08%, between about 0.055% and about 0.08%, between about 0.06% and about 0.08%, between about 0.065% and about 0.08%, between about 0.07% and about 0.08%, or between about 0.075% and about 0.08%.

In another aspect, cysteine is at a concentration of between about 0.005% and about 0.06%, between about 0.01% and about 0.06%, between about 0.015% and about 0.06%, between about 0.02% and about 0.06%, between about 0.025% and about 0.06%, between about 0.03% and about 0.06%, between about 0.035% and about 0.06%, between about 0.04% and about 0.06%, between about 0.045% and about 0.06%, between about 0.05% and about 0.06%, or between about 0.055% and about 0.06%.

In one aspect, cysteine is at a concentration of between about 0.005% and about 0.04%, between about 0.01% and about 0.04%, between about 0.015% and about 0.04%, between about 0.02% and about 0.04%, between about 0.025% and about 0.04%, between about 0.03% and about 0.04%, or between about 0.035% and about 0.04%.

In another aspect, cysteine is at a concentration of between about 0.005% and about 0.06%, between about 0.01% and about 0.05%, between about 0.015% and about 0.04%, or between about 0.02% and about 0.03%.

In another aspect, the present disclosure provides a lyophilized fecal microbe composition comprising a lyophilization formulation comprising trehalose and cysteine, wherein the lyophilization formulation is capable of maintaining at least about 30% cell viability immediately post lyophilization relative to a pre-lyophilization cell viability. In one aspect, a lyophilization formulation comprises at least 15% trehalose and at least 0.025% L-cysteine.

In one aspect, the present disclosure provides lyophilized fecal microbiota pharmaceutical composition comprising a lyophilization formulation comprising at least about 12.5% trehalose, wherein the lyophilization formulation is capable of providing a cell integrity maintenance ratio of at least 35%.

In one aspect, the present disclosure provides a method of preparing a lyophilized fecal microbe preparation, the method comprising:
  a. obtaining a liquid fecal microbe preparation in a lyophilization formulation comprising between 12.5% and 17.5% trehalose; and
  b. freeze-drying the liquid fecal microbe preparation, wherein the lyophilization formulation is capable of providing a cell integrity maintenance ratio of at least about 30%.

In another aspect, a method further comprises producing a liquid fecal microbe preparation from a stool in the absence of culturing of fecal microbes prior to mixing the stool with a homogenization buffer (see FIG. 1). For example, fresh feces can be directly homogenized in a buffer without culturing. In an aspect, unprocessed stool is directly mixed with a formulation described here (e.g., comprising trehalose, cysteine, or both) without culturing the fecal microbes.

FIG. 1 illustrates an example embodiment of a process for manufacturing a composition as described herein. At Step 1, fresh donor stool is evaluated for the presence of pathogens and the general health of the donor. At Step 2, the stool is combined with a liquid composition (e.g. homogenization buffer comprising saline, trehalose and reducing agent such as cysteine) to facilitate homogenization. At Step 3, the stool is homogenized in the liquid composition to produce a stool liquid suspension. At Step 4, the stool liquid suspension is filtered and the filtrate collected. At Step 5, the filtrate is frozen. At Step 6, the frozen filtrate is lyophilized to give rise a formulated composition as described herein. Such final composition can then be tested for safety and efficacy and administered to a subject in need thereof. In addition, in certain embodiments, the filtrate collected at Step 4 can be directly administered to a subject, without freezing or lyophilization.

In another aspect, the present disclosure provides a frozen fecal microbe composition comprising trehalose, wherein the frozen fecal microbe composition is capable of being thawed at least once without loss of microbial cell membrane integrity of more than 50%. In one aspect, a frozen fecal microbe composition is capable of being thawed at least 2, 3, 4, 5, or 6 times without loss of microbial cell membrane integrity of more than 50%. In another aspect, a frozen fecal microbe is capable of being thawed at least once, 2, 3, 4, 5, or 6 times without loss of microbial cell membrane integrity of more than 40%, more than 35%, more than 30%, more than 25%, more than 20%, more than 15%, more than 10%, or more than 5%. In another aspect, a frozen fecal microbe composition further comprises cysteine selected from the group consisting of D-cysteine and L-cysteine.

In another aspect, this disclosure provides a method for treating a disorder or condition in a subject in need thereof, comprising administering to the subject a therapeutically effective amount of a pharmaceutical composition or a previously frozen fecal microbe composition disclosed herein, wherein the disorder or condition is selected from the group consisting of Acne, AIDS Enteropathy, AIDS-related Gastroenteritis, Alopecia Totalis, Alzheimers Disease, Amyloidosis, Amyotrophic Lateral Sclerosis, Ankylosing Spondylitis, Anorexia, Antibiotic Associated Colitis, Asbergers Syndrome, Attention Deficit Disorder (ADD), Attention Deficit Hyperactivity Disorder (ADHD), Autism Spectrum Disorder (ASD), Behcet's Syndrome, Chronic *Clostridium difficile* Infection (CDI), Chronic constipation, Chronic Depression, Chronic Fatigue Syndrome (CFS), Chronic Idiopathic Pseudo Obstructive Syndrome, Chronic Inflammation Demyelinating Polyneuropathy, Chronic Nausea, Chronic Urticaria, Coeliac Disease, Collagenous Colitis, Colonic Polyps, Constipation Predominant FBD, Crohn's Disease, Cryptogenic Cirrhosis, Cyclic Vomiting, Dermatitis Herpetiformis, Diabetes, Familial Mediterranean Fever, Fatty Liver, Functional Bowel Disease (FBD), Gastro-oesophageal Reflux, Gillian-Barre Syndrome, Glomerulonephritis, Haemolytic Uraemic Syndrome, Halitosis, IBS constipation-predominant, IBS diarrhea/constipation alternating, IBS diarrhea-predominant, IBS pain-predominant, Idiopathic Thrombocytopenic Purpura (ITP), Idiopathic/Simple Constipation, Indeterminate Colitis, Inflammatory Bowel Disease (IBD), Irritable bowel syndrome (IBS), Juvenile Diabetes Mellitus, Lyme Disease, Manic Depressive Illness, Metabolic Syndrome, Microscopic Colitis, Migraine, Mixed Cryoglobulinaemia, Mucous Colitis, Multiple Sclerosis, Myasthenia Gravis, NASH (Nonalcoholic Steatohepatitis), Non-Rheumatoid Arthritis, Non-Rheumatoid Factor Positive Arthritis, Non-ulcer Dyspepsia, Norwalk Viral Gastroenteritis, Obesity, Obsessive Compulsive Disorder, Pain Predominant FBD, Parkinson's Disease, Polyarteritis, Polyposis *Coli*, Primary Biliary Cirrhosis, Primary *Clostridium difficile* Infection (CDI), Primary Sclerosing Cholangitis (PSC), Pseudomembranous Colitis, Psychotic Disorders, Reiter's Syndrome, Relapsing Diverticulitis, Rett Syndrome, Rheumatoid Arthritis, Rosacea, Rotavirus Gastroenteritis, Sacroiliitis, Schizophrenia, Scleroderma, Sjogren's Syndome, Small Bowel Bacterial Overgrowth, Sudden Infant Death Syndrome (SIDS), Systemic Lupus Erythematosus, Ulcerative Colitis, Upper Abdominal FBD, Vasculitic Disorders, Viral Gastroenteritis, pre-diabetic syndrome, type I diabetes, type II diabetes, depression, schizophrenia, and a mood disorder.

In another aspect, this disclosure provides a method for treating a disorder or condition in a subject in need thereof, comprising administering to the subject a therapeutically effective amount of a pharmaceutical composition or a previously frozen fecal microbe composition disclosed herein, wherein the disorder or condition is selected from the group consisting of recurrent *C. difficile* infection, autism spectrum disorder (ASD), constipation predominant functional bowel disease (FBD), pain predominant FBD, upper abdominal FBD, non-ulcer dyspepsia (NUD), gastro-oesophageal reflux, indeterminate colitis, microscopic colitis, pseudomembranous colitis, viral gastroenteritis, Norwalk viral gastroenteritis, rotavirus gastroenteritis, AIDS related gastroenteritis, non rheumatoid factor positive arthritis, Lyme disease, systemic lupus, idiopathic thrombocytopenic purpura, Sjogren's syndrome, haemolytic uremic syndrome or scleroderma, Gillain-Barre syndrome, Chronic Inflammatory Demyelinating Polyneuropathy, chronic depression, schizophrenia, psychotic disorders, manic depressive illness, Asbergers syndrome, Rett syndrome, attention deficit hyperactivity disorder (ADHD), attention deficit disorder (ADD), sudden infant death syndrome (SIDS), and anorexia nervosa.

In another aspect, this disclosure provides a method for treating a disorder or condition in a subject in need thereof, comprising administering to the subject a therapeutically effective amount of a pharmaceutical composition or a previously frozen fecal microbe composition disclosed herein, wherein the disorder or condition is selected from the group consisting of recurrent or primary *C. difficile* infection, autism spectrum disorder (ASD), ulcerative colitis, Crohn's disease, and irritable bowel syndrome.

In one aspect, a fecal microbiota preparation comprises a donor's entire or substantially complete microbiota. In one aspect, a fecal microbiota preparation comprises a non-selected fecal microbiota. In another aspect, a fecal microbiota preparation comprises an isolated or purified population of live non-pathogenic fecal bacteria. In a further aspect, a fecal microbiota preparation comprises a non-selected and substantially complete fecal microbiota preparation from a single donor.

In one aspect, bacterial cell viability is measured by using imaging assays that measure membrane permeability. A combination of membrane permeant and impermeant DNA dyes stains are used (e.g., intact cells stained green and dead cells stained red). In one aspect, a SYTO BC dye and propidium idodide are used to stain and differentiate live and dead bacteria. See Example 2. In one aspect, SYTO 9 and propidium idodide are used to stain and differentiate live and dead bacteria. See Stocks, Cytometry A. 2004 October; 61(2):189-95. In another aspect, live cell determination is combined with fluorescent Gram staining. In another aspect, the number of viable bacterial cells in a sample is assessed by a colorimetric method, e.g., a Dojindo's Microbial Viability Assay Kit-WST.

In one aspect, bacterial cell viability assessed by counting the number of colonies on an agar plate is the standard method for determining the number of viable bacterial cells in samples. In another aspect, cell viability is evaluated via molecular viability analyses, e.g., a PCR-based approach, which can differentiate nucleic acids associated with viable cells from those associated with non-viable cells. See Cangelosi and Meschcke, Appl Environ Microbiol. 2014 October; 80(19): 5884-5891.

In one aspect, a therapeutic composition comprises a cryoprotectant. In another aspect, a cryoprotectant comprises, consists essentially of, or consists of polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof. In an aspect of the present disclosure, a cryoprotectant can be selected from the group comprising 5% Sucrose; 10% Sucrose; 10% Skim milk; 10% Trehalose with 2.5% sucrose; 5% Trehalose with 2.5% sucrose; 5% Mannitol; 5% Mannitol with 0.1% Polysorbate 80; 10% Mannitol; 10% Mannitol with 0.1% Polysorbate 80; 5% Trehalose; 5% Trehalose with 0.1% Polysorbate 80; 10% Trehalose; and 10% Trehaolse with 0.1% Polysorbate 80.

In another aspect, a therapeutic composition comprises a lyoprotectant. In one aspect, the same substance or the same substance combination is used as both a cryoprotectant and a lyoprotectant. Exemplary lyoprotectants include sugars such as sucrose or trehalose; an amino acid such as monosodium glutamate or histidine; a methylamine such as betaine; a lyotropic salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In one aspect, a lyoprotectant is a non-reducing sugar, such as trehalose or sucrose. In one aspect, a cryoprotectant or a lyoprotectant consists essentially of, or consists of, one or more substances mentioned in this paragraph and the paragraph above.

In one aspect, a cryoprotectant or a lyoprotectant comprise an intracellular agent, e.g., DMSO, Glycerol, or PEG, which penetrates inside the cell preventing the formation of ice crystals that could result in membrane rupture. In another aspect, a cryoprotectant or a lyoprotectant comprise an extracellular agent, e.g., sucrose, trehalose, or dextrose, which does not penetrate into the cell membrane but acts to improve the osmotic imbalance that occurs during freezing.

In one aspect, a lyophilized formulation comprises trehalose. In one aspect, a lyophilized formulation comprises 2% to 30%, 3% to 25%, 4% to 20%, 5% to 15%, 6% to 10%, 2% to 30%, 2% to 25%, 2% to 20%, 2% to 15%, or 2% to 10% trehalose. In one aspect, a lyophilized formulation comprises at least 2%, 3%, 4%, 5%, 6%, 7%, 8%, 9%, 10%, or 15% trehalose. In one aspect, a lyophilized formulation comprises at most 2%, 3%, 4%, 5%, 6%, 7%, 8%, 9%, 10%, or 15% trehalose. In one aspect, a lyophilized formulation comprises about 5% trehalose. In one aspect, a lyophilized formulation comprises trehalose and sucrose. In one aspect, a lyophilized formulation comprises between about 8% to 12% trehalose with between about 1.5% to 3.5% sucrose and between about 0.5% to 1.5% NaCl.

In one aspect, the preparation of a fecal microbiota preparation involves a treatment selected from the group consisting of ethanol treatment, detergent treatment, heat treatment, irradiation, and sonication, or a combination thereof. In one aspect, the preparation of a fecal microbiota preparation involves no treatment selected from the group consisting of ethanol treatment, detergent treatment, heat treatment, irradiation, and sonication. In one aspect, the preparation of a fecal microbiota preparation involves a separation step selected from the group consisting of filtering, sieving, density gradients, filtration, chromatography, and a combination thereof. In one aspect, the preparation of a fecal microbiota preparation does not require one or more separation steps selected from the group consisting of filtering, sieving, density gradients, filtration, and chromatography. In one aspect, a fecal microbiota preparation is substantially free of non-living matter. In one aspect, a fecal microbiota preparation is substantially free of acellular material selected from the group consisting of residual fiber, DNA, viral coat material, and non-viable material. In one aspect, a fecal microbiota preparation is substantially free of eukaryotic cells from the fecal microbiota's donor.

In one aspect, a pharmaceutical composition provided here, after at least 12 weeks of storage at ambient temperature or lower, is effective for treating one or more disorders selected from the group consisting of recurrent or primary C. difficile infection, autism spectrum disorder (ASD), ulcerative colitis, Crohn's disease, and irritable bowel syndrome. In another aspect, a pharmaceutical composition remains effective after at least 4, 8, 10, 16, 20, 24, 30, 40, 50, 60, 70, 80 or 100 weeks of storage at ambient temperature or lower.

In one aspect, the present disclosure provides a method for treating a disorder (e.g., C. difficile infection, autism spectrum disorder (ASD), ulcerative colitis, Crohn's disease, or another indication listed herein) in a subject in need thereof, where the method comprises administering to the subject a pharmaceutically active dose of a therapeutic composition described herein. In one aspect, the present disclosure provides a method for treating a disorder (e.g., C. difficile infection, ASD, ulcerative colitis, or Crohn's disease) in a subject in need thereof, where the method comprises administering daily to the subject a pharmaceutically active dose of a therapeutic composition described herein. In one aspect, a therapeutic composition is administered to a patient in need thereof at least once daily for at least two consecutive days. In one aspect, a therapeutic composition is administered at least once daily for at least 3, 4, 5, 6, 7, 8, 9, 10, 11, 12, 13, 14, or 15 consecutive days. In another aspect, a therapeutic composition is administered at least once daily for at least 1, 2, 3, 4, 5, 6, 7, 8, 9, 10, 11, or 12 consecutive weeks. In another aspect, a therapeutic composition is administered at least twice, three times, four times, or five times per week for at least 1, 2, 3, 4, 5, 6, 7, 8, 9, 10, 11, or 12 consecutive weeks. In one aspect, a therapeutic composition is administered at least once daily for at most 4, 5, 6, 7, 8, 9, 10, 11, 12, 13, 14, 15, 16, 17, 18, 19, or 20 consecutive days or weeks. In another aspect, a therapeutic composition is administered at least once daily for at most 1, 2, 3, 4, 5, 6, 7, 8, 9, 10, 11, or 12 consecutive weeks or months. In a further aspect, a therapeutic composition is administered at least once for at least 1, 2, 3, 4, 5, 6, 7, 8, 9, 10, 11, or 12 consecutive months or years, chronically for a subject's entire life span, or an indefinite period of time.

In one aspect, a therapeutic composition is administered to a patient in need thereof at least twice daily for at least two consecutive days. In one aspect, a therapeutic composition is administered at least twice daily for at least 3, 4, 5, 6, 7, 8, 9, 10, 11, 12, 13, 14, or 15 consecutive days. In another aspect, a therapeutic composition is administered at least twice daily for at least 1, 2, 3, 4, 5, 6, 7, 8, 9, 10, 11, or 12 consecutive weeks. In one aspect, a therapeutic composition is administered at least twice daily for at most 4, 5, 6, 7, 8, 9, 10, 11, 12, 13, 14, 15, 16, 17, 18, 19, or 20 consecutive days or week. In another aspect, a therapeutic composition is administered at least twice daily for at most 1, 2, 3, 4, 5, 6, 7, 8, 9, 10, 11, or 12 consecutive weeks or months. In a further aspect, a therapeutic composition is administered at least twice for at least 1, 2, 3, 4, 5, 6, 7, 8, 9, 10, 11, or 12 consecutive months or years, chronically for a subject's entire life span, or an indefinite period of time.

In one aspect, a therapeutic composition is administered to a patient in need thereof at least three times daily for at least two consecutive days. In one aspect, a therapeutic composition is administered at least three times daily for at least 3, 4, 5, 6, 7, 8, 9, 10, 11, 12, 13, 14, or 15 consecutive days. In another aspect, a therapeutic composition is administered at least three times daily for at least 1, 2, 3, 4, 5, 6, 7, 8, 9, 10, 11, or 12 consecutive weeks. In one aspect, a therapeutic composition is administered at least three times daily for at most 4, 5, 6, 7, 8, 9, 10, 11, 12, 13, 14, 15, 16, 17, 18, 19, or 20 consecutive days or weeks. In another aspect, a therapeutic composition is administered at least three times daily for at most 1, 2, 3, 4, 5, 6, 7, 8, 9, 10, 11, or 12 consecutive weeks or months. In a further aspect, a therapeutic composition is administered at least three times for at least 1, 2, 3, 4, 5, 6, 7, 8, 9, 10, 11, or 12 consecutive months or years, chronically for a subject's entire life span, or an indefinite period of time.

In one aspect, the present disclosure provides a method for treating a disorder (e.g., C. difficile infection, ASD, ulcerative colitis, or Crohn's disease) in a subject in need thereof, where the method comprises administering orally to the subject a pharmaceutically active dose of a therapeutic composition comprising live, non-pathogenic, synthetic bacterial mixture or live, non-pathogenic, purified or extracted, fecal microbiota in a lyophilized formulation described herein, where the dose is administered at a dosing schedule of at least once or twice daily for at least three consecutive days or weeks. In another aspect, a dose is administered at least once, twice, or three times daily for a period between 1 and 12 weeks, between 2 and 12 weeks, between 3 and 12 weeks, between 4 and 12 weeks, between 5 and 12 weeks, between 6 and 12 weeks, between 7 and 12 weeks, between 8 and 12 weeks, between 9 and 12 weeks, between 10 and 12 weeks, between 1 and 2 weeks, between 2 and 3 weeks, between 3 and 4 weeks, between 4 and 5 weeks, between 5 and 6 weeks, between 6 and 7 weeks, between 7 and 8 weeks, between 8 and 9 weeks, between 9 and 10 weeks, or between 10 and 11 weeks.

In one aspect, the present disclosure provides a method for treating a disorder (e.g., C. difficile infection, ASD, ulcerative colitis, or Crohn's disease) in a subject in need thereof by administering a pharmaceutical composition described herein, where the method comprises a first dosing schedule followed by a second dosing schedule. In one aspect, a first dosing schedule comprises a treatment or induction dose. In one aspect, a first dosing schedule comprises a continuous dosing schedule. In another aspect, a second dosing schedule comprises a maintenance dose lower than or equal to a pharmaceutically active dose of a first dosing schedule. In another aspect, a second dosing schedule lasts for at least about 2, 4, 6, 8, 10, 12, 18, 24, 36, 48, 72, or 96 months. In one aspect, a second dosing schedule lasts permanently, for a treated subject's entire life span, or an indefinite period of time. In one aspect, a second dosing schedule is a continuous dosing schedule. In another aspect, a second dosing schedule is an intermittent dosing schedule. In a further aspect, a second dosing schedule is an intermittent dosing schedule comprising a treatment period of at least 1, 2, 3, 4, 5, 6, 7, 8, 9, 10, 11, 12, 13, or 14 days followed by a resting period of at least 1, 2, 3, 4, 5, 6, 7, 8, 9, 10, 11, 12, 13, or 14 days. In another aspect, a second dosing schedule comprises administering a second dose (e.g., a maintenance dose) every other day, every two days, or every 3, 4, 5, 6, 7, 8 days. In another aspect, a maintenance dose is administered for an extended period of time with or without titration (or otherwise changing the dosage or dosing schedule). In one aspect, the interval between a first and a second dosing schedule is at least about 1, 2, 3, 4, 5, 6, 7, 8, 9, 10, 11, or 12 weeks. In another aspect, a second dosing schedule (e.g., a maintenance dose) comprises a dosage about 2, 5, 10, 50, 100, 200, 400, 800, 1000, 5000 or more fold lower than the dosage used in a first dosing schedule (e.g., an initial treatment dose). In another aspect, a second dosing schedule (e.g., a maintenance dosing schedule) has an equal or lower dosing frequency than a first dosing schedule (e.g., an initial treatment dosing schedule). In another aspect, a second dosing schedule (e.g., a maintenance dosing schedule) has a higher dosing interval than a first dosing schedule (e.g., an initial treatment dosing schedule).

In one aspect, a first or second dosing schedule used in a method can be once-a-week, twice-a-week, or thrice-a-week. The term "once-a-week" means that a dose is administered once in a week, preferably on the same day of each week. "Twice-a-week" means that a dose is administered two times in a week, preferably on the same two days of each weekly period. "Thrice-a-week" means that a dose is administered three times in a week, preferably on the same three days of each weekly period.

In one aspect, a subject being treated is a subject already with a disorder (e.g., ulcerative colitis or Crohn's disease). Administration of a disclosed therapeutic composition to a clinically asymptomatic human subject who is genetically predisposed or prone to a disorder (e.g., ulcerative colitis or Crohn's disease) is also useful in preventing or inhibiting the onset of clinical symptoms. A human subject genetically predisposed or prone to ulcerative colitis can be a human subject having a close family member or relative exhibiting or having suffered a disorder (e.g., ulcerative colitis or Crohn's disease). In another aspect, a subject being treated is a subject in which ulcerative colitis is to be prevented or inhibited. In another aspect, a subject being treated is predisposed or susceptible to a disorder (e.g., ulcerative colitis or Crohn's disease). In another aspect, a subject being treated is a subject diagnosed as having a disorder (e.g., ulcerative colitis or Crohn's disease). In one aspect, a subject being treated is a patient in need thereof.

In one aspect, a subject being treated is a human patient. In one aspect, a patient is a male patient. In one aspect, a patient is a female patient. In one aspect, a patient is a premature newborn. In one aspect, a patient is a term newborn. In one aspect, a patient is a neonate. In one aspect, a patient is an infant. In one aspect, a patient is a toddler. In one aspect, a patient is a young child. In one aspect, a patient is a child. In one aspect, a patient is an adolescent. In one aspect, a patient is a pediatric patient. In one aspect, a patient is a geriatric patient. In one aspect, a human patient is a child patient below about 18, 15, 12, 10, 8, 6, 4, 3, 2, or 1 year old. In another aspect, a human patient is an adult patient. In another aspect, a human patient is an elderly patient. In a further aspect, a human patient is a patient above about 30, 35, 40, 45, 50, 55, 60, 65, 70, 75, 80, 85, 90, or 95 years old. In another aspect, a patient is about between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old. In one aspect, a patient is a young old patient (65-74 years). In one aspect, a patient is a middle old patient (75-84 years). In one aspect, a patient is an old patient (>85 years).

In one aspect, a method comprises administering a therapeutic composition orally, by enema, or via rectal suppository. In one aspect, a pharmaceutical composition is formulated as a geltab, pill, microcapsule, capsule, or tablet. In one aspect, a therapeutic composition is formulated as an enteric coated capsule or microcapsule, acid-resistant capsule or microcapsule, or formulated as part of or administered together with a food, a food additive, a dairy-based product, a soy-based product or a derivative thereof, a jelly, or a yogurt. In another aspect, a therapeutic composition is formulated as an acid-resistant enteric coated capsule. A therapeutic composition can be provided as a powder for sale in combination with a food or drink. A food or drink can be a dairy-based product or a soy-based product. In another aspect, a food or food supplement contains enteric-coated and/or acid-resistant microcapsules containing a therapeutic composition.

In an aspect, a therapeutic composition comprises a liquid culture. In another aspect, a therapeutic composition is lyophilized, pulverized and powdered. It may then be infused, dissolved such as in saline, as an enema. Alternatively the powder may be encapsulated as enteric-coated and/or acid-resistant capsules for oral administration. These capsules may take the form of enteric-coated and/or acid-resistant microcapsules. A powder can preferably be provided in a palatable form for reconstitution for drinking or for reconstitution as a food additive. In a further aspect, a food is yogurt. In one aspect, a powder may be reconstituted to be infused via naso-duodenal infusion. In another aspect, therapeutic compositions are designed for targeted delivery of an active ingredient into the distal small bowel or the colon.

In another aspect, a therapeutic composition is in a liquid, frozen, freeze-dried, spray-dried, foam-dried, lyophilized, or powder formulation. In a further aspect, a therapeutic composition is formulated as a delayed or gradual enteric release form. In another aspect, a therapeutic composition comprises an excipient, a saline, a buffer, a buffering agent, or a fluid-glucose-cellobiose agar (RGCA) media.

In one aspect, a therapeutic composition further comprises an acid suppressant, an antacid, an H2 antagonist, a proton pump inhibitor or a combination thereof. In one aspect, a therapeutic composition is substantially free of non-living matter. In another aspect, a therapeutic composition is substantially free of acellular material selected from the group consisting of residual fiber, DNA, viral coat material, and non-viable material.

In one aspect, a therapeutic composition also comprises or is supplemented with a prebiotic nutrient selected from the group consisting of polyols, fructooligosaccharides (FOSs), oligofructoses, inulins, galactooligosaccharides (GOSs), xylooligosaccharides (XOSs), polydextroses, monosaccharides, tagatose, and/or mannooligosaccharides.

In one aspect, a method further comprises pretreating a subject with an antibiotic composition prior to administering a therapeutic bacterial or microbiota composition. In one aspect, an antibiotic composition comprises an antibiotic selected from the group consisting of rifabutin, clarithromycin, clofazimine, vancomycin, rifampicin, nitroimidazole, chloramphenicol, and a combination thereof. In another aspect, an antibiotic composition comprises an antibiotic selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof. In a further aspect, a method further comprises pretreating a subject with an anti-inflammatory drug prior to administration of a therapeutic bacterial or microbiota composition.

In one aspect, every about 200 mg of a pharmaceutical composition comprises a pharmacologically active dose. In one aspect, every about 75, 100, 125, 150, 175, 200, 250, 300, 350, 400, 450, 500, 750, 1000, 1500, or 2000 mg of a pharmaceutical composition comprises a pharmacologically active dose.

In one aspect, a pharmaceutically active or therapeutic effective dose comprises at least about $10^5$, $10^6$, $10^7$, $10^8$, $10^9$, $10^{10}$, $10^{11}$, $10^{12}$, or $10^{13}$ cfu. In another aspect, a pharmaceutically active therapeutic effective dose comprises at most about $10^5$, $10^6$, $10^7$, $10^8$, $10^9$, $10^{10}$, $10^{11}$, $10^{12}$, $10^{13}$, $10^{14}$, or $10^{15}$ cfu. In a further aspect, a pharmacologically active therapeutic effective dose is selected from the group consisting of from $10^8$ cfu to $10^{14}$ cfu, from $10^9$ cfu to $10^{13}$ cfu, from $10^{10}$ cfu to $10^{12}$ cfu, from $10^9$ cfu to $10^{14}$ cfu, from $10^9$ cfu to $10^{12}$ cfu, from $10^9$ cfu to $10^{11}$ cfu, from $10^9$ cfu to $10^{10}$ cfu, from $10^{10}$ cfu to $10^{14}$ cfu, from $10^{10}$ cfu to $10^{13}$ cfu, from $10^{11}$ cfu to $10^{14}$ cfu, from $10^{11}$ cfu to $10^{13}$ cfu, from $10^{12}$ cfu to $10^{14}$ cfu, and from $10^{13}$ cfu to $10^{14}$ cfu.

In one aspect, a pharmaceutically active or therapeutic effective dose comprises at least about $10^5$, $10^6$, $10^7$, $10^8$, $10^9$, $10^{10}$, $10^{11}$, $10^{12}$, or $10^{13}$ cells or spores. In another aspect, a pharmaceutically active or therapeutic effective dose comprises at most about $10^5$, $10^6$, $10^7$, $10^8$, $10^9$, $10^{10}$, $10^{11}$, $10^{12}$, or $10^{13}$ total cells or spores. In a further aspect, a pharmacologically active or therapeutic effective dose is selected from the group consisting of from $10^8$ to $10^{14}$, from $10^9$ to $10^{13}$, from $10^{10}$ to $10^{12}$, from $10^9$ to $10^{14}$, from $10^9$ to $10^{12}$, from $10^9$ to $10^{11}$, from $10^9$ to $10^{10}$, from $10^{10}$ to $10^{14}$, from $10^{10}$ to $10^{13}$, from $10^{11}$ to $10^{14}$, from $10^{11}$ to $10^{13}$, from $10^{12}$ to $10^{14}$, and from $10^{13}$ to $10^{14}$ cells or spores. In an aspect, the pharmaceutically active or therapeutic effective dose cell count is directed to live cells.

In one aspect, a therapeutic composition comprises one or more, two or more, three or more, four or more, or five or more isolated, purified, or cultured microorganisms selected from the group consisting of *Clostridium, Bacillus, Collinsella, Bacteroides, Eubacterium, Fusobacterium, Propionibacterium, Lactobacillus, Ruminococcus, Escherichia coli, Gemmiger, Desulfomonas, Peptostreptococcus, Bifidobacterium, Coprococcus, Dorea,* and *Monilia.*

In one aspect, a fecal microbiota preparation described herein comprises a purified or reconstituted fecal bacterial mixture. In one aspect, a fecal microbiota preparation comprises one or more, one or more, two or more, three or more, four or more, or five or more live fecal microorganisms are selected from the group consisting of *Acidaminococcus, Akkermansia, Alistipes, Anaerotruncus, Bacteroides, Bifidobacterium, Blautia, Butyrivibrio, Clostridium, Collinsella, Coprococcus, Corynebacterium, Dorea, Enterococcus, Escherichia, Eubacterium, Faecalibacterium, Haemophilus, Holdemania, Lactobacillus, Moraxella, Parabacteroides, Prevotella, Propionibacterium, Raoultella, Roseburia, Ruminococcus, Staphylococcus, Streptococcus, Subdoligranulum,* and *Veillonella.* In one aspect, a fecal microbiota preparation comprises one or more, one or more, two or more, three or more, four or more, or five or more live fecal microorganisms selected from the group consisting of *Bacteroides fragilis* ssp. *vulgatus, Collinsella aerofaciens, Bacteroides fragilis* ssp. *thetaiotaomicron, Peptostreptococcus productus* II, *Parabacteroides distasonis, Faecalibacterium prausnitzii, Coprococcus eutactus, Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ssp. A, *Eubacterium biforme, Bifidobacterium infantis, Eubacterium rectale, Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Coprococcus catus, Aerostipes hadrus, Eubacterium cylindroides, Eubacterium ruminantium, Staphylococcus epidermidis, Eubacterium limosum, Tissirella praeacuta, Fusobacterium mortiferum* I, *Fusobacterium naviforme, Clostridium innocuum, Clostridium ramosum, Propionibacterium acnes, Ruminococcus flavefaciens, Bacteroides fragilis* ssp. *ovatus, Fusobacterium nucleatum, Fusobacterium mortiferum, Escherichia coli, Gemella morbillorum, Finegoldia magnus, Streptococcus intermedius, Ruminococcus lactaris, Eubacterium tenue, Eubacterium ramulus, Bacteroides clostridiiformis* ssp. *clostridliformis, Bacteroides coagulans, Prevotella oxalis, Prevotella ruminicola, Odoribacter splanchnicus,* and *Desuifomonas pigra.*

In one aspect, a fecal microbiota preparation lacks or is substantially devoid of one or more, two or more, three or more, four or more, or five or more live fecal microorganisms selected from the group consisting of *Acidaminococcus, Akkermansia, Alistipes, Anaerotruncus, Bacteroides, Bifidobacterium, Blautia, Butyrivibrio, Clostridium, Collinsella, Coprococcus, Corynebacterium, Dorea, Enterococcus, Escherichia, Eubacterium, Faecalibacterium, Haemophilus, Holdemania, Lactobacillus, Moraxella, Parabacteroides, Prevotella, Propionibacterium, Raoultella, Roseburia, Ruminococcus, Staphylococcus, Streptococcus, Subdoligranulum,* and *Veillonella.* In one aspect, a fecal microbiota preparation lacks or is substantially devoid of one or more, two or more, three or more, four or more, or five or live more fecal microorganisms are selected from the group consisting of *Bacteroides fragilis* ssp. *vulgatus, Collinsella aerofaciens, Bacteroides fragilis* ssp. *thetaiotaomicron, Peptostreptococcus productus* II, *Parabacteroides distasonis, Faecalibacterium prausnitzii, Coprococcus eutactus, Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens,*

*Bacteroides eggerthii, Clostridium leptum, Bacteroides fragilis* ssp. A, *Eubacterium biforme, Bifidobacterium infantis, Eubacterium rectale, Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Coprococcus catus, Aerostipes hadrus, Eubacterium cylindroides, Eubacterium ruminantium, Staphylococcus epidermidis, Eubacterium limosum, Tissirella praeacuta, Fusobacterium mortiferum* I, *Fusobacterium naviforme, Clostridium innocuum, Clostridium ramosum, Propionibacterium acnes, Ruminococcus flavefaciens, Bacteroides fragilis* ssp. *ovatus, Fusobacterium nucleatum, Fusobacterium mortiferum, Escherichia coli, Gemella morbillorum, Finegoldia magnus, Streptococcus intermedius, Ruminococcus lactaris, Eubacterium tenue, Eubacterium ramulus, Bacteroides clostridiiformis* ssp. *clostridliformis, Bacteroides coagulans, Prevotella oralis, Prevotella ruminicola, Odoribacter splanchnicus*, and *Desuifomonas pigra*.

In another aspect, a therapeutic composition comprises a fecal microbiota further supplemented, spiked, or enhanced with a fecal microorganism. In one aspect, a fecal microbiota is supplemented with a non-pathogenic (or with attenuated pathogenicity) bacterium of *Clostridium, Collinsella, Dorea, Ruminococcus, Coprococcus, Prevotella, Veillonella, Bacteroides, Baccillus*, or a combination thereof. In another aspect, a therapeutic composition comprises a fecal microbiota further supplemented, spiked, or enhanced with a species of Veillonellaceae, Firmicutes, Gammaproteobacteria, Bacteroidetes, or a combination thereof. In another aspect, a therapeutic composition comprises a fecal microbiota further supplemented with fecal bacterial spores. In one aspect, fecal bacterial spores are *Clostridium* spores, *Bacillus* spores, or both.

In an aspect, a therapeutic composition comprises a fecal microbiota from a subject selected from the group consisting of a human, a bovine, a dairy calf, a ruminant, an ovine, a caprine, or a *cervine*. In another aspect, a therapeutic composition can be administered to a subject selected from the group consisting of a human, a bovine, a dairy calf, a ruminant, an ovine, a caprine, or a *cervine*. In an aspect, a therapeutic composition is substantially or nearly odourless.

In an aspect, a therapeutic composition provided here comprises a fecal microbiota comprising a Shannon Diversity Index of greater than or equal to 0.3, greater than or equal to 0.4, greater than or equal to 0.5, greater than or equal to 0.6, greater than or equal to 0.7, greater than or equal to 0.8, greater than or equal to 0.9, greater than or equal to 1.0, greater than or equal to 1.1, greater than or equal to 1.2, greater than or equal to 1.3, greater than or equal to 1.4, greater than or equal to 1.5, greater than or equal to 1.6, greater than or equal to 1.7, greater than or equal to 1.8, greater than or equal to 1.9, greater than or equal to 2.0, greater than or equal to 2.1, greater than or equal to 2.2, greater than or equal to 2.3, greater than or equal to 2.4, greater than or equal to 2.5, greater than or equal to 3.0, greater than or equal to 3.1, greater than or equal to 3.2, greater than or equal to 3.3, greater than or equal to 3.4, greater than or equal to 3.5, greater than or equal to 3.6, greater than or equal to 3.7, greater than or equal to 3.8, greater than or equal to 3.9, greater than or equal to 4.0, greater than or equal to 4.1, greater than or equal to 4.2, greater than or equal to 4.3, greater than or equal to 4.4, greater than or equal to 4.5, or greater than or equal to 5.0. In another aspect, a therapeutic composition comprises fecal microbiota comprising a Shannon Diversity Index of between 0.1 and 3.0, between 0.1 and 2.5, between 0.1 and 2.4, between 0.1 and 2.3, between 0.1 and 2.2, between 0.1 and 2.1, between 0.1 and 2.0, between 0.4 and 2.5, between 0.4 and 3.0, between 0.5 and 5.0, between 0.7 and 5.0, between 0.9 and 5.0, between 1.1 and 5.0, between 1.3 and 5.0, between 1.5 and 5.0, between 1.7 and 5.0, between 1.9 and 5.0, between 2.1 and 5.0, between 2.3 and 5.0, between 2.5 and 5.0, between 2.7 and 5.0, between 2.9 and 5.0, between 3.1 and 5.0, between 3.3 and 5.0, between 3.5 and 5.0, between 3.7 and 5.0, between 31.9 and 5.0, or between 4.1 and 5.0. In one aspect, a Shannon Diversity Index is calculated at the phylum level. In another aspect, a Shannon Diversity Index is calculated at the family level. In one aspect, a Shannon Diversity Index is calculated at the genus level. In another aspect, a Shannon Diversity Index is calculated at the species level. In a further aspect, a therapeutic composition comprises a preparation of flora in proportional content that resembles a normal healthy human fecal flora.

In a further aspect, a therapeutic composition comprises fecal bacteria from at least 1, 2, 3, 4, 5, 6, 7, 8, 9, or 10 different families. In another aspect, a therapeutic composition comprises fecal bacteria from at least 11, 12, 13, 14, 15, 16, 17, 18, 19, or 20 different families. In yet another aspect, a therapeutic composition comprises fecal bacteria from at least 21, 22, 23, 24, 25, 26, 27, 28, 29, or 30 different families. In a further aspect, a therapeutic composition comprises fecal bacteria from at least 31, 32, 33, 34, 35, 36, 37, 38, 39, or 40 different families. In another aspect, a therapeutic composition comprises fecal bacteria from at least 41, 42, 43, 44, 45, 46, 47, 48, 49, or 50 different families. In another aspect, a therapeutic composition comprises fecal bacteria from between 1 and 10, between 10 and 20, between 20 and 30, between 30 and 40, between 40 and 50 different families. In an aspect, a therapeutic composition provided here comprises a fecal microbiota comprising no greater than 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material. In another aspect, a therapeutic composition provided here comprises a fecal microbiota comprising no greater than 20%, 25%, 30%, 35%, 40%, 45%, 50%, 55%, 60%, 65%, 70%, 75%, 80%, 85%, 90%, or 95% weight non-living material/weight biological material. In another aspect, a therapeutic composition provided here comprises, consists of, or consists essentially of, particles of non-living material and/or particles of biological material of a fecal sample that passes through a sieve, a column, or a similar filtering device having a sieve, exclusion, or particle filter size of 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, 0.004 mm, 0.002 mm, 0.001 mm or 0.0005 mm. "Non-living material" does not include an excipient, e.g., a pharmaceutically inactive substance, such as a cryoprotectant, added to a processed fecal material. "Biological material" refers to the living material in fecal material, and includes microbes including prokaryotic cells, such as bacteria and archaea (e.g., living prokaryotic cells and spores that can sporulate to become living prokaryotic cells), eukaryotic cells such as protozoa and fungi, and viruses. In one aspect, "biological material" refers to the living material, e.g., the microbes, eukaryotic cells, and viruses, which are present in the colon of a normal healthy human. In an aspect, a therapeutic composition provided or comprises an extract of human feces where the composition is substantially odorless. In an aspect, a therapeutic composition provided or comprises fecal material or a fecal floral preparation in a lyophilized, crude, semi-purified or purified formulation.

In an aspect, a fecal microbiota in a therapeutic composition comprises highly refined or purified fecal flora, e.g., substantially free of non-floral fecal material. In an aspect, a fecal microbiota can be further processed, e.g., to undergo microfiltration before, after, or before and after sieving. In another aspect, a highly purified fecal microbiota product is ultra-filtrated to remove large molecules but retain the therapeutic microflora, e.g., bacteria.

In another aspect, a fecal microbiota in a therapeutic composition used herein comprises or consists essentially of a substantially isolated or a purified fecal flora or entire (or substantially entire) microbiota that is (or comprises) an isolate of fecal flora that is at least about 40%, 45%, 50%, 55%, 60%, 65%, 70%, 75%, 80%, 85%, 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9%, 1.0%, 2%, 5%, 10%, 15%, 20%, 25%, 30%, 35%, 40%, 45%, 50%, 55% or more non-fecal floral material; or, a substantially isolated, purified, or substantially entire microbiota as described in Sadowsky et al., WO 2012/122478 A1, or as described in Borody et al., WO 2012/016287 A2. In one aspect, a fecal microbiota preparation comprises a weight ratio between fecal-derived non-living material and fecal-derived biological material of no greater than about 0.1%, 0.2%, 0.3%, 0.4%, 0.5%, 0.6%, 0.7%, 0.8%, 0.9%, 1%, 2%, 5%, 8%, 10%, 15%, 20%, 30%, 40%, or 50%.

In an aspect, a fecal microbiota in a therapeutic composition comprises a donor's substantially entire or non-selected fecal microbiota, reconstituted fecal material, or synthetic fecal material. In another aspect, the fecal microbiota in a therapeutic composition comprises no antibiotic resistant population. In another aspect, a therapeutic composition comprises a fecal microbiota and is largely free of extraneous matter (e.g., non-living matter including acellular matter such as residual fiber, DNA, RNA, viral coat material, non-viable material; and living matter such as eukaryotic cells from the fecal matter's donor).

In an aspect, a fecal microbiota in a therapeutic composition used herein is derived from disease-screened fresh homologous feces or equivalent freeze-dried and reconstituted feces. In an aspect, a fresh homologous feces does not include an antibiotic resistant population. In another aspect, a fecal microbiota in a therapeutic composition is derived from a synthetic fecal composition. In an aspect, a synthetic fecal composition comprises a preparation of viable flora which preferably in proportional content, resembles normal healthy human fecal flora which does not include antibiotic resistant populations. Suitable microorganisms may be selected from the following: *Bacteroides, Eubacterium, Fusobacterium, Propionibacterium, Lactobacillus, Ruminococcus, Escherichia coli, Gemmiger, Clostridium, Desulfomonas, Peptostreptococcus, Bifidobacterium, Collinsella, Coprococcus, Dorea*, and *Ruminococcus*.

In an aspect, a therapeutic composition is combined with other adjuvants such as antacids to dampen bacterial inactivation in the stomach. (e.g., Mylanta, Mucaine, Gastrogel). In another aspect, acid secretion in the stomach could also be pharmacologically suppressed using H2-antagonists or proton pump inhibitors. An example H2-antagonist is ranitidine. An example proton pump inhibitor is omeprazole. In one aspect, an acid suppressant is administered prior to administering, or in co-administration with, a therapeutic composition.

In an aspect, a therapeutic composition is administered in the form of: an enema composition which can be reconstituted with an appropriate diluent; enteric-coated capsules; enteric-coated microcapsules; acid-resistant tablet; acid-resistant capsules; acid-resistant microcapsules; powder for reconstitution with an appropriate diluent for naso-enteric infusion or colonoscopic infusion; powder for reconstitution with appropriate diluent, flavoring and gastric acid suppression agent for oral ingestion; powder for reconstitution with food or drink; or food or food supplement comprising enteric-coated and/or acid-resistant microcapsules of the composition, powder, jelly, or liquid.

In an aspect, a treatment method effects a cure, reduction of the symptoms, or a percentage reduction of symptoms of a disorder (e.g., IBD such as ulcerative colitis or Crohn's disease). The change of flora is preferably as "near-complete" as possible and in one embodiment the flora is replaced by viable organisms which will crowd out any remaining, original flora. Typically the change in enteric flora comprises introduction of an array of predetermined flora into the gastro-intestinal system, and thus in a preferred form the method of treatment comprises substantially or completely displacing pathogenic enteric flora in patients requiring such treatment.

In another aspect, a therapeutic composition can be provided together with a pharmaceutically acceptable carrier. As used herein, a "pharmaceutically acceptable carrier" refers to a non-toxic solvent, dispersant, excipient, adjuvant, or other material which is mixed with a live bacterium in order to permit the formation of a pharmaceutical composition, e.g., a dosage form capable of administration to the patient. A pharmaceutically acceptable carrier can be liquid (e.g., saline), gel or solid form of diluents, adjuvant, excipients or an acid resistant encapsulated ingredient. Suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof. In another aspect, a therapeutic composition may contain auxiliary substances such as wetting or emulsifying agents, stabilizing or pH buffering agents. In an aspect, a therapeutic composition contains about 1%-5%, 5%-10%, 10%-15%, 15-20%, 20%-25%, 25-30%, 30-35%, 40-45%, 50%-55%, 1%-95%, 2%-95%, 5%-95%, 10%-95%, 15%-95%, 20%-95%, 25%-95%, 30%-95%, 35%-95%, 40%-95%, 45%-95%, 50%-95%, 55%-95%, 60%-95%, 65%-95%, 70%-95%, 45%-95%, 80%-95%, or 85%-95% of active ingredient. In an aspect, a therapeutic composition contains about 2%-70%, 5%-60%, 10%-50%, 15%-40%, 20%-30%, 25%-60%, 30%-60%, or 35%-60% of active ingredient.

In an aspect, a therapeutic composition can be incorporated into tablets, drenches, boluses, capsules or premixes. Formulation of these active ingredients into such dosage forms can be accomplished by means of methods well known in the pharmaceutical formulation arts. See, e.g., U.S. Pat. No. 4,394,377. Filling gelatin capsules with any desired form of the active ingredients readily produces capsules. If desired, these materials can be diluted with an inert powdered diluent, such as sugar, starch, powdered milk, purified crystalline cellulose, or the like to increase the volume for convenience of filling capsules.

In an aspect, conventional formulation processes can be used to prepare tablets containing a therapeutic composition.

In addition to the active ingredients, tablets may contain a base, a disintegrator, an absorbent, a binder, and a lubricant. Typical bases include lactose, sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents include starch and lactose. Magnesium carbonate is also useful for oily substances. As a binder there can be used, for example, gelatin, gums, starch, dextrin, polyvinyl pyrrolidone and various cellulose derivatives. Among the commonly used lubricants are magnesium stearate, talc, paraffin wax, various metallic soaps, and polyethylene glycol.

In an aspect, for preparing solid compositions such as tablets, an active ingredient is mixed with a pharmaceutical carrier, e.g., conventional tableting ingredients such as corn starch, lactose, sucrose, sorbitol, talc, stearic acid, magnesium stearate, dicalcium phosphate or gums, or other pharmaceutical diluents, e.g. water, to form a solid preformulation composition containing a homogeneous mixture of a composition of the present disclosure. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing a desired amount of an active ingredient (e.g., at least about $10^5$, $10^6$, $10^7$, $10^8$, $10^9$, $10^{10}$, $10^{11}$, $10^{12}$, or $10^{13}$ cfu or total cell count). A therapeutic composition used herein can be flavored.

In an aspect, a therapeutic composition can be a tablet or a pill. In one aspect, a tablet or a pill can be coated or otherwise compounded to provide a dosage form affording the advantage of prolonged action. For example, a tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

In an aspect, a therapeutic composition is formulated as a delayed or gradual enteric release form. In an aspect, a delayed or gradual enteric release formulation comprises the use of cellulose acetate, polyethylene glycerol, or both. In an aspect, a delayed or gradual enteric release formulation comprises the use of a hydroxypropylmethylcellulose (HPMC), a microcrystalline cellulose (MCC), magnesium stearate, or a combination thereof. In an aspect, a delayed or gradual enteric release formulation comprises the use of a poly(meth)acrylate, a methacrylic acid copolymer B, a methyl methacrylate, a methacrylic acid ester, a polyvinylpyrrolidone (PVP), a PVP-K90, or a combination thereof. In an aspect, a delayed or gradual enteric release formulation comprises the use of a solid inner layer sandwiched between two outer layers; wherein the solid inner layer comprises the pharmaceutical composition and another component selected from the group consisting of a disintegrant, an exploding agent, an effervescent or any combination thereof; wherein the outer layer comprises a substantially water soluble, a crystalline polymer, or both. In an aspect, a delayed or gradual enteric release formulation comprises the use of a non-swellable diffusion matrix.

In another aspect, a delayed or gradual enteric release formulation comprises the use of a bilayer tablet or capsule which comprises a first layer comprising a polyalkylene oxide, a polyvinylpyrrolidone, a lubricant, or a mixture thereof, and a second osmotic push layer comprising polyethylene oxide, carboxy-methylcellulose, or both. In an aspect, a delayed or gradual enteric release formulation comprises the use of a release-retarding matrix material selected from the group consisting of an acrylic polymer, a cellulose, a wax, a fatty acid, shellac, zein, hydrogenated vegetable oil, hydrogenated castor oil, polyvinylpyrrolidine, a vinyl acetate copolymer, a vinyl alcohol copolymer, polyethylene oxide, an acrylic acid and methacrylic acid copolymer, a methyl methacrylate copolymer, an ethoxyethyl methacrylate polymer, a cyanoethyl methacrylate polymer, an aminoalkyl methacrylate copolymer, a poly(acrylic acid), a poly(methacrylic acid), a methacrylic acid alkylamide copolymer, a poly(methyl methacrylate), a poly(methacrylic acid anhydride), a methyl methacrylate polymer, a polymethacrylate, a poly(methyl methacrylate) copolymer, a polyacrylamide, an aminoalkyl methacrylate copolymer, a glycidyl methacrylate copolymer, a methyl cellulose, an ethylcellulose, a carboxymethylcellulose, a hydroxypropylmethylcellulose, a hydroxymethyl cellulose, a hydroxyethyl cellulose, a hydroxypropyl cellulose, a crosslinked sodium carboxymethylcellulose, a crosslinked hydroxypropylcellulose, a natural wax, a synthetic wax, a fatty alcohol, a fatty acid, a fatty acid ester, a fatty acid glyceride, a hydrogenated fat, a hydrocarbon wax, stearic acid, stearyl alcohol, beeswax, glycowax, castor wax, carnauba wax, a polylactic acid, polyglycolic acid, a co-polymer of lactic and glycolic acid, carboxymethyl starch, potassium methacrylate/divinylbenzene copolymer, crosslinked polyvinylpyrrolidone, poly inylalcohols, polyvinylalcohol copolymers, polyethylene glycols, non-crosslinked polyvinylpyrrolidone, polyvinylacetates, polyvinylacetate copolymers, or any combination thereof. In an aspect, a delayed or gradual enteric release formulation comprises the use of a microenvironment pH modifier.

In an aspect, a therapeutic composition can be a drench. In one aspect, a drench is prepared by choosing a saline-suspended form of a therapeutic composition. A water-soluble form of one ingredient can be used in conjunction with a water-insoluble form of the other by preparing a suspension of one with an aqueous solution of the other. Water-insoluble forms of either active ingredient may be prepared as a suspension or in some physiologically acceptable solvent such as polyethylene glycol. Suspensions of water-insoluble forms of either active ingredient can be prepared in oils such as peanut, corn, sesame oil or the like; in a glycol such as propylene glycol or a polyethylene glycol; or in water depending on the solubility of a particular active ingredient. Suitable physiologically acceptable adjuvants may be necessary in order to keep the active ingredients suspended. Adjuvants can include and be chosen from among the thickeners, such as carboxymethylcellulose, polyvinyl pyrrolidone, gelatin and the alginates. Surfactants generally will serve to suspend the active ingredients, particularly the fat-soluble propionate-enhancing compounds. Most useful for making suspensions in liquid nonsolvents are alkylphenol polyethylene oxide adducts, naphthalene-sulfonates, alkylbenzene-sulfonates, and the polyoxyethylene sorbitan esters. In addition many substances, which affect the hydrophilicity, density and surface tension of the liquid, can assist in making suspensions in individual cases. For example, silicone anti-foams, glycols, sorbitol, and sugars can be useful suspending agents.

In an aspect, a therapeutic composition comprises non-pathogenic spores of one or more, two or more, three or more, or four or more *Clostridium* species selected from the group consisting of *Clostridium absonum, Clostridium argentinense, Clostridium baratii, Clostridium botulinum, Clostridium cadaveris, Clostridium carnis, Clostridium celatum, Clostridium chauvoei, Clostridium clostridioforme, Clostridium cochlearium, Clostridium fallax, Clostridium felsineum, Clostridium ghonii, Clostridium glycolicum, Clostridium haemolyticum, Clostridium hastiforme, Clostridium histolyticum, Clostridium indolis, Clostridium irregulare, Clostridium limosurn, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertium, Clostridium tetani, Clostridium welchii*, and *Clostridium villosum*.

In an aspect, a therapeutic composition comprises purified, isolated, or cultured viable non-pathogenic *Clostridium* and a plurality of purified, isolated, or cultured viable non-pathogenic microorganisms from one or more genera selected from the group consisting of *Collinsella, Coprococcus, Dorea, Eubacterium*, and *Ruminococcus*. In another aspect, a therapeutic composition comprises a plurality of purified, isolated, or cultured viable non-pathogenic microorganisms from one or more genera selected from the group consisting of *Clostridium, Collinsella, Coprococcus, Dorea, Eubacterium*, and *Ruminococcus*.

In an aspect, a therapeutic composition comprises two or more genera selected from the group consisting of *Collinsella, Coprococcus, Dorea, Eubacterium*, and *Ruminococcus* In another aspect, a therapeutic composition comprises two or more genera selected from the group consisting of *Coprococcus, Dorea, Eubacterium*, and *Ruminococcus*. In a further aspect, a therapeutic composition comprises one or more, two or more, three or more, four or more, or five or more species selected from the group consisting of *Coprococcus catus, Coprococcus comes, Dorea longicatena, Eubacterium eligens, Eubacterium hadrum, Eubacterium hallii, Eubacterium rectale*, and *Ruminococcus torques*.

In one aspect, a pharmaceutical composition is in an anaerobic package or container. In another aspect, a pharmaceutical composition further comprises an oxygen scavenger. In one aspect, a container can be made oxygen free by e.g., incorporating into the container a built in or clipped-on oxygen-scavenging mechanism, e.g., oxygen scavenging pellets as described e.g., in U.S. Pat. No. 7,541,091. In another aspect, the container itself is made of an oxygen scavenging material, e.g., oxygen scavenging iron, e.g., as described by O2BLOCK™, or equivalents, which uses a purified and modified layered clay as a performance-enhancing carrier of oxygen-scavenging iron; the active iron is dispersed directly in the polymer. In one aspect, oxygen-scavenging polymers are used to make the container itself or to coat the container, or as pellets to be added; e.g., as described in U.S. Pat. App. Pub. 20110045222, describing polymer blends having one or more unsaturated olefinic homopolymers or copolymers; one or more polyamide homopolymers or copolymers; one or more polyethylene terephthalate homopolymers or copolymers; that exhibit oxygen-scavenging activity. In one aspect, oxygen-scavenging polymers are used to make the container itself or to coat the container, or as pellets to be added; e.g., as described in U.S. Pat. App. Pub. 20110008554, describing compositions comprising a polyester, a copolyester ether and an oxidation catalyst, wherein the copolyester ether comprises a polyether segment comprising poly(tetramethylene-co-alkylene ether). In one aspect, oxygen-scavenging polymers are used to make the container itself or to coat the container, or as pellets to be added; e.g., as described in U.S. Pat. App. Pub. 201000255231, describing a dispersed iron/salt particle in a polymer matrix, and an oxygen scavenging film with oxygen scavenging particulates.

In one aspect, of the pharmaceutical compositions provided herein, the pharmaceutical compositions are manufactured, labelled or formulated for human or animal use, and optionally the animal use is for a veterinary use.

In one aspect, the pharmaceutical compositions provided herein are further processed or manufactured or formulated as a liquid, a suspension, a cream, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation.

In one aspect, provided herein are delivery vehicles, products of manufacture, containers or devices comprising a pharmaceutical composition as provided herein, optionally formulated for or calibrated for repeat or multiple implantations, administration, delivery or infusions.

In one aspect, provided herein are delivery vehicles, products of manufacture, containers or devices, further comprising one or more of: an additive, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent, coloring agent, at least one vitamin, mineral and/or dietary supplement, or a prebiotic nutrient.

In one aspect, provided herein are methods for making a pharmaceutical composition comprising a lyophilized, cryodesiccated, freeze-dried or dehydrated bacterial flora, comprising:

(a) providing a composition, isolate or preparation comprising, or consisting essentially of, or consisting of:

an entire (or substantially entire) fecal microbiota, optionally isolated and/or stored in a partially, substantially or completely anaerobic environment, a treated or untreated fecal flora sample, a complete or partial fecal flora sample, optionally isolated and/or stored in a partially, substantially or completely anaerobic environment, a fecal flora substantially or completely purified of non-fecal floral fecal material, wherein optionally the fecal flora is separated from a rough particulate matter in a fecal sample by: homogenizing, centrifuging and/or filtering a rough particulate matter or a non-floral matter of the fecal material, or by plasmapheresis, centrifugation, celltrifuge, column chromatography or by immunoprecipitation, and optionally the substantially or completely purified fecal flora has no greater than about 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material, a partially, substantially or completely isolated or purified fecal flora or fecal flora filtrate, wherein optionally the purification process comprises filtering a fecal sample with a filter medium, wherein optionally the filter medium includes at least one sieve size of no greater than about 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, or 0.01 mm, or a sieve size of 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm, to result in or to generate a filtrate, a disease screened fresh homologous feces, optionally substantially or completely purified of non-fecal floral fecal material, or optionally isolated and/or stored in a partially, substantially or completely anaerobic environment, and optionally the fecal flora is initially derived from an individual screened or tested for a disease or an infection, and/or the fecal flora is initially derived from an individual screened to have a normal, healthy or wild type population of fecal flora, a reconstituted feces, optionally reconstituted using cultured viable non-pathogenic or attenuated microorganisms, a synthetic fecal composition of predetermined flora, a synthetic or reconstituted fecal composition comprising a preparation of viable flora in proportional content that resembles a normal healthy human fecal flora, which does not include antibiotic resistant populations, a composition comprising viable, non-pathogenic colonic bacterial cells selected from the group consisting of a Clostridia, a *Collinsella*, a *Bacteroides*, a Fusobacteria, a Propionibacteria, a Lactobacilli, an anaerobic cocci, a *Ruminococcus*, an *E. coli*, a *Gemmiger*, a Desu/fomonas, a *Peptostreptococcus*, a Bifidobacteria and any combination thereof;

a composition comprising viable, non-pathogenic colonic bacterial components of fecal flora, wherein the bacterial components comprise *Clostridium bifermentans*, *Clostridium innocuum*, *Clostridium butyricum*, *Escherichia coli*, *Bacteroides* and *Peptostreptococcus productus*, a composition comprising viable, non-pathogenic colonic bacterial components of fecal flora, wherein the bacterial components comprise a *Bacteroides*, an *Escherichia coli*, and a non-pathogenic Clostridia, wherein optionally the non-pathogenic Clostridia comprise a *Clostridium innocuum*, a *Clostridium bifermentans* and a *Clostridium ramosum*, a composition comprising a plurality of viable non-pathogenic Clostridia and a plurality of viable non-pathogenic *Collinsella*, and optionally with no viable Lactobacilli, Bifidobacteria or Eubacteria, and optionally with no viable *Bacteroides, Fusobacteria, Propionibacteria, Lactobacilli, anaerobic cocci, Ruminococcus, E. coli, Gemmiger*, Desulfomonas, *Peptostreptococcus* or Bifidobacteria, a composition comprising a plurality of viable non-pathogenic Clostridia, wherein optionally the plurality of viable non-pathogenic Clostridia comprise non-pathogenic Clostridia spores, a composition comprising a plurality of viable non-pathogenic Clostridia and a plurality of viable non-pathogenic *Collinsella*, wherein optionally the plurality of viable non-pathogenic Clostridia comprise non-pathogenic Clostridia spores and/or the plurality of viable non-pathogenic Clostridia comprise non-pathogenic *Collinsella* spores, wherein optionally the plurality of viable non-pathogenic Clostridia and are from a first pure culture and the plurality of viable non-pathogenic *Collinsella* cells from a second pure culture, and/or a composition comprising viable non-pathogenic Clostridia spores, a viable non-pathogenic *Bacteroides*, and a viable non-pathogenic *Escherichia coli*, wherein optionally the composition, isolate or preparation has at least about $10^6$ viable cells/g, $10^7$ viable cells/g, $10^8$ viable cells/g, at least about $10^9$ viable cells/g, $10^{10}$ viable cells/g, $10^{11}$ viable cells/g, $10^{12}$ viable cells/g, $10^{13}$ viable cells/g, $10^{14}$ viable cells/g, or $10^{15}$ viable cells/g, or between about $10^6$ and $10^{15}$, between about $10^8$ and $10^{15}$ viable cells/g, or between about $10^{10}$ and $10^{12}$ viable cells/g;

(b) providing a cryoprotectant and optionally a surfactant or an emulsifier, wherein optionally the cryoprotectant comprises: a dimethyl sulfoxide (DMSO) or equivalent; a glycerol, a polyethylene glycol (PEG) or equivalent; a polysaccharide; a sugar, or an amino acid, wherein optionally the amino acid comprises an alanine, a glycine, a proline, or the sugar comprises a mannitol, a sucrose, a glucose, a lactose, a ribose or trehalose, or the polysaccharide comprises a hydroxypropyl-β-cyclodextrin (HPβCD), or the cryoprotectant comprises any combination of different cryoprotectant compounds, wherein optionally the surfactant or emulsifier comprises a polysorbate (polyoxyethylene sorbitan monolaurate) or a PEG-ylated sorbitan, optionally a Polysorbate 80 (polyoxyethylene (80) sorbitan monolaurate);

(c) homogenizing the composition, isolate or preparation of (a) with a mixture of saline and cryoprotectant, or with a mixture of saline, cryoprotectant and a surfactant or an emulsifier, wherein optionally the homogenization is about 1:2, 1:3, 1:4 or 1:5 (w/w) with a solution comprising saline, and optionally the cryoprotectant is present at a concentration of at least 1%, 2%, 3%, 4%, 5%, 6%, 7%, 8%, 9%, or 10% (vol/vol);

(d) lyophilizing, cryodesiccating, freeze-drying or dehydrating the homogenized composition, isolate or preparation mixture of (c), wherein optionally after the lyophilizing, cryo-desiccating, freeze-drying or dehydrating the final water activity (aw) is less than about 0.1, 0.2, 0.3 or 0.4; and (e) storing, keeping and/or maintaining the lyophilized, cryo-desiccated, freeze-dried or dehydrated composition, isolate or preparation at ambient temperature, room temperature, approximately room temperature, freezing temperature, or at between about 2° C. to 8° C., or at between about 15° C. to 26° C., or at about 20° C., 21° C., 22° C., 23° C., 24° C., 25° C., 26° C., 27° C. or 28° C., wherein optionally the stored pharmaceutical composition has at least about $10^8$ viable cells/g, $10^9$ viable cells/g, $10^{10}$ viable cells/g, $10^{12}$ viable cells/g, $10^{13}$ viable cells/g, or $10^{14}$ viable cells/g, or between about $10^7$ and $10^{12}$ viable cells/g, or between about $10^9$ and $10^{11}$ viable cells/g.

In one aspect, the pharmaceutical compositions are formulated in a gastric acid resistant capsule.

In one aspect, provided are methods for treating a disorder in a subject in need thereof, the method comprising administering to the subject an amount of the pharmaceutical composition disclosed herein, wherein the disorder is selected from the group consisting of recurrent *C. difficile* infection, autism, constipation predominant functional bowel disease (FBD), pain predominant FBD, upper abdominal FBD, non-ulcer dyspepsia (NUD), gastro-oesophageal reflux, indeterminate colitis, microscopic colitis, pseudomembranous colitis, viral gastroenteritis, Norwalk viral gastroenteritis, rotavirus gastroenteritis, AIDS related gastroenteritis, non-rheumatoid factor positive arthritis, Lyme disease, systemic lupus, idiopathic thrombocytopenic purpura, Sjogren's syndrome, haemolytic uremic syndrome or scleroderma, Gillain-Barre syndrome, Chronic Inflammatory Demyelinating Polyneuropathy, chronic depression, schizophrenia, psychotic disorders, manic depressive illness, Asbergers syndrome, Rett syndrome, attention deficit hyperactivity disorder (ADHD), and attention deficit disorder (ADD), sudden infant death syndrome (SIDS), anorexia nervosa.

In one aspect, provided are methods comprising storing the pharmaceutical composition as provided herein at ambient temperature, room temperature, approximately room temperature, freezing temperature, or at between about 2° C. to 8° C., or at between about 15° C. to 26° C., or at about 20° C., 21° C., 22° C., 23° C., 24° C., 25° C., 26° C., 27° C. or 28° C.; and optionally, at least 50%, at least 55%, at least 60%, at least 65%, at least 70%, at least 75%, at least 80%, at least 85%, at least 90%, or at least 95% microbial viability of the microflora material of the pharmaceutical composition is maintained, or between about 40% and 95% of the microflora material of the pharmaceutical composition is maintained, after about 2, about 4, about 8, about 12, about 20, about 30, about 40, about 50, or about 60 weeks of storage from (after) preparation of the pharmaceutical composition, or after between about 2 to 60 weeks from (after) preparation of the pharmaceutical composition. or after between about 1 to 12 months, or 2 to 24 months, from (after) preparation of the pharmaceutical composition.

In one aspect, provided are methods and compositions facilitating prolonged viability or longer term survival of FMT, e.g., filtered fecal microbiota, at e.g., ambient temperatures, e.g., at room temperatures (including storage, including long term storage at ambient temperatures, e.g., at room temperatures); and while the disclosure is not limited by any particular mechanism of action, this prolonged viability or longer term survival can be achievable through the use of a cryoprotectant and/or a mix of cryoprotectants at various mix compositions, thus, storage at ambient temperature (e.g., prolonged shelf-life in pharmacy or home) may be achieved. In one aspect, the cryoprotectants and associated liquids include trehalose, sucrose, normal saline, mannitol, and polysorbate(s), e.g., a polysorbate 80, in various combinations.

In one aspect, provided are compositions having the ability to isolate, prepare, formulate and/or reduce the volume of the FMT product so as to store it in a delivery system, e.g., as a bottle-top of a drink, e.g., a chocolate drink, as a side compartment of yoghurt, or a two-layered aluminized top of ice-cream tub for kids, e.g., for autism, and methods of preparation of same.

In one aspect, provided are compositions prepared and/or formulated in a powdered form, or equivalent; these formulations can be useful for storage in e.g., a tablet or capsule, or in an ampoule to e.g., crack open and dissolve in a liquid for, e.g., insertion, mixing or injection into e.g. a channel of a colonoscope or a naso-enteric tube, and the like; or as a powder in a bag ready to add e.g., as a solution which can be e.g., infused into an NG tube (or equivalent), or a colonoscope, or a gastroscope for e.g., stoma gastrostomy, or a PEG tube.

In one aspect, provided are freeze dried or lyophilized materials, which can be formulated or manufactured into or as an edible or friable product, e.g., a biscuit-like product, which can be e.g., crushed into a powder to dissolve in a drink or to insert into a tablet or a capsule. In one aspect, provided are FMT-comprising formulations that are orally ingestible, or can be a rectally applied product. In one aspect, provided are FMT-comprising formulations in the form of a dry lozenge or a chewing gum or equivalent. In one aspect, use of all of these formulations, foods, drinks, and products of manufacture are facilitated by the ability to manufacture, ship and store at room temperature, at an ambient temperature, at a freezing temperature, or at between about 2° C. to 8° C., as provided by this disclosure.

In one aspect, provided herein are compositions, e.g., formulations and pharmaceutical preparations, products of manufacture, and containers and delivery vehicles, and devices and delivery materials, comprising treated and/or isolated faecal (fecal) material for faecal floral transplantation. In one aspect, the treated and/or isolated fecal material provided herein comprise faecal floral (e.g., bacteria) transplanted between different individuals, e.g., human to human or between animals. In one aspect, the treated fecal material provided herein is transplanted back into the same individual from which it was collected, e.g., to repopulate a colon after drug treatment (e.g., antibiotic treatment or chemotherapy) or after an orthostatic lavage, e.g., for inducing the purgation (e.g., cleansing) of a gastrointestinal (GI) tract, including a colon.

In one aspect, compositions, e.g., formulations and pharmaceutical preparations, products of manufacture, and containers and delivery vehicles, and devices and delivery materials provided herein are used for the amelioration, stabilization, or treatment of a bowel disease or infection comprising use of a delivery vehicle, formulation, product of manufacture, or container or device provided herein; e.g., as a fecal bacteriotherapy, fecal transfusion, fecal transplant, or human probiotic infusion (HPI). In one aspect, provided herein are methods for using compositions provided herein for e.g., ameliorating, stabilizing, treating or preventing any infection, bowel disease or condition having a bowel dysfunction component, for example, a poisoning, a pseudomembranous colitis, a *Clostridium difficile* infection, an inflammatory bowel disease (IBD), Crohn's disease, hepatic encephalopathy, enteritis, colitis, irritable bowel syndrome (IBS), fibromyalgia (FM), alopecia areata/totalis, anorexia nervosa, autism, chronic fatigue syndrome (CFS), depression, attention deficit/hyperactivity disorder (ADHD), multiple sclerosis (MS), systemic lupus erythematosus (SLE), travellers' diarrhea, small intestinal bacterial overgrowth, chronic pancreatitis, or a pancreatic insufficiency.

For example, in one aspect, as antibiotics do not eradicate *C. difficile* and its spore, a delivery vehicle, formulation, product of manufacture, or container or device as provided herein, e.g., comprise treated and/or isolated fecal flora for use to ameliorate, stabilize or eradicate *C. difficile* (or the pseudo-membranous colitis associated with this infection) when infused into a colon of the infected or ill individual, e.g., a patient or animal. In one aspect, the fecal flora obtained from a donor comprises a part of, substantially all of, or all of the infected or ill recipient's missing or inadequate (e.g., in numbers or function) fecal flora, e.g., bacteria. While the disclosure is not limited by any particular mechanism of action, in some aspects it is the transfer of the equivalent of: a part of, substantially all of, or all of the fecal flora of the infected individual from the donor to the recipient (e.g., from human to human) that ameliorates or eradicates the infection or the pseudo-membranous colitis associated with this infection.

In one aspect, the compositions, e.g., formulations and pharmaceutical preparations, and devices, delivery materials, delivery vehicles, products of manufacture, containers and devices provided herein allow the safe transplantation of fecal flora (e.g., human flora) components to individuals in need thereof, e.g., to infected, sick and dying patients, thus providing a consistently safe yet functioning flora for delivery to a recipient or patient.

In one aspect, provided herein is a reliable method for producing standardized fresh fecal flora which can have a long shelf life. In one aspect, the delivery vehicle, formulation, pharmaceutical preparation, product of manufacture, container or device comprising the fecal flora comprises a substantially or completely oxygen-free environment. In another aspect, nutrients such as "prebiotic nutrients" can be added (e.g., in dry or liquid forms) to a composition provided herein. A prebiotic nutrient can be any ingredient that stimulates the stability, growth and/or activity of the fecal flora, e.g., bacteria; for example, in one aspect, polyols, fructooligosaccharides (FOSs), oligofructoses, inulins, galactooligosaccharides (GOSs), xylooligosaccharides (XOSs), polydextroses, monosaccharides such as tagatose, and/or mannooligosaccharides are used as prebiotics to practice this disclosure. In one aspect, the prebiotics are added to prevent "shock" to the fecal flora subsequent to their isolation or purification, freezing, freeze-drying, spray-drying, reconstitution in solution and the like.

In one aspect, components of the compositions, e.g., delivery vehicles, formulations and pharmaceutical preparations, products of manufacture, or containers or devices, provided herein comprise an entire (or substantially entire) microbiota, or a *Bacteroides* and/or Firmicutes in large numbers (e.g., a larger proportion of *Bacteroides* and/or Firmicutes is present that is normally found in situ), e.g., to be able to ameliorate and/or eradicate a *C. difficile* infection and/or the pseudo-membranous colitis associated with this infection. In one aspect, the compositions, e.g., delivery vehicles, formulations and pharmaceutical preparations, products of manufacture, or containers or devices, provided herein can be available (e.g., formulated and/or dosaged for) for recurrent use in individuals, e.g., in patients or animals, with the more difficult to treat conditions such as colitis (e.g., the pseudo-membranous colitis of a *C. difficile* infection) and constipation.

In one aspect, components of the compositions e.g., delivery vehicles, formulations and pharmaceutical preparations, products of manufacture, or containers or devices, provided herein comprise a selection of bacterial species e.g. *Bacteroides*, Firmicutes, *Bacillus thuringiensis* (a bacterium capable of producing peptide antibiotics for *C. difficile*). The bacterial species may be separated by celltrifugation or plasmapheresis.

In one aspect, the selection of bacterial species e.g. *Bacteroides*, Firmicutes, *Bacillus thuringiensis* may be added to components of the compositions, e.g., delivery vehicles, formulations and pharmaceutical preparations, products of manufacture, or containers or devices as fortification of concentrations comprising the bacterial species to contain wild types of bacteria.

In one aspect, compositions provided herein can be re-formulated as fecal slurries, saline or buffered suspensions (e.g., for an enema, suspended in a buffer or a saline), in a drink (e.g., a milk, yoghurt, a shake, a flavoured drink or equivalent) for oral delivery, and the like.

In one aspect, compositions provided herein can be formulated or re-formulated as an enema product, a spray dried product, reconstituted enema, a small capsule product, a small capsule product suitable for administration to children, a bulb syringe, a bulb syringe suitable for a home enema with a saline addition, a powder product, a powder product in oxygen deprived sachets, a powder product in oxygen deprived sachets that can be added to, for example, a bulb syringe or enema, or a spray dried product in a device that can be attached to a container with an appropriate carrier medium such as yoghurt or milk and that can be directly incorporated and given as a dosing for example for children.

In one aspect, compositions provided herein can be delivered directly in a carrier medium via a screw-top lid wherein the fecal material is suspended in the lid and released on twisting the lid straight into the carrier medium.

In one aspect, provided herein include fecal slurries formulated for insertion/administration into the bowel, e.g., via an enema suspended in saline or a buffer, orally in a drink (e.g., a milk, yoghurt, a flavoured drink and the like), via a small bowel infusion via a nasoduodenal tube, via a gastrostomy, or by using a colonoscope. In some aspect, there may be advantages delivering via a colonoscope to infuse as proximally as possible, and to detect any colonic pathology.

In one aspect, methods, fecal flora used in compositions provided herein are initially derived (entirely or in part) from an individual screened or tested for a disease or infection, and/or the fecal flora is initially derived from an individual screened to have a normal, healthy or normal, representative "wild type" population of fecal flora; e.g., a normal complement of a *Bacteroides* and/or Firmicutes, and/or other fecal flora such as *Bacillus Thuringiensis*. In one aspect, depending on a deficiency of a floral (e.g., bacterial) specie or species in a donor fecal material, or to achieve a desired effect, one or more additional (or "supplemental") species, e.g., *Bacteroides*, Firmicutes and/or *Bacillus Thuringiensis* species, is added to (or is administered with) the delivered product either initially when the product is made, or at the time of delivery, e.g., the additional species is/are mixed in before application to the individual (e.g., patient or animal), e.g., when a powder, lyophilate, or freeze-dried composition is reconstituted for delivery; or the one or more additional (or "supplemental") species can be co-administered. These additional floral species can be directly isolated or purified from a donor, or can be expanded (cultured) for a time in vitro before addition, or can come from (be derived from) a pure culture, e.g., from an ATTC stock. For example, in some applications, e.g., to achieve a desired effect or therapeutic outcome, a delivery of an enhanced amount of one or more fecal flora (e.g., bacterial) species is used, e.g., the delivered product (e.g., an entire (or substantially entire) microbiota, or a composition comprising a complete or partial fecal flora, or a partially, substantially or completely isolated or purified fecal flora) is enhanced with (is "spiked" with) one or more additional (or "supplemental") species, e.g., *Bacteroides*, Firmicutes and/or *Bacillus Thuringiensis* species, which can be directly isolated from a donor, or can come from a pure culture, and the like.

In some aspects, selection of the donor is of crucial importance, e.g., to avoid infecting the recipient with a separate infection or disease. In one aspect, the donor is tested (screened) at least for e.g., retrovirus (e.g., human immunodeficiency virus, HIV); hepatitis A, B, and/or C; cytomegalovirus; Epstein-Barr virus, detectable parasites and/or bacterial pathogens, depending on the specie of the donor and recipient, e.g., human or animal.

In one aspect, provided herein is a process for preparing fecal flora (e.g., an entire (or substantially entire) microbiota) for transplantation, first comprising a collection from one or more healthy (e.g., screened) donor(s). In one aspect, a fresh stool is transported via a stool collection device, which can provide or comprises a suitably oxygen free (or substantially oxygen free) appropriate container. In one aspect, the container can be made oxygen free by e.g., incorporating into the container a built in or clipped-on oxygen-scavenging mechanism, e.g., oxygen scavenging pellets as described e.g., in U.S. Pat. No. 7,541,091. In another aspect, the container itself is made of an oxygen scavenging material, e.g., oxygen scavenging iron, e.g., as described by O2BLOCK™, or equivalents, which uses a purified and modified layered clay as a performance-enhancing carrier of oxygen-scavenging iron; the active iron is dispersed directly in the polymer. In one aspect, oxygen-scavenging polymers are used to make the container itself or to coat the container, or as pellets to be added; e.g., as described in U.S. Pat. App. Pub. 20110045222, describing polymer blends having one or more unsaturated olefinic homopolymers or copolymers; one or more polyamide homopolymers or copolymers; one or more polyethylene terephthalate homopolymers or copolymers; that exhibit oxygen-scavenging activity. In one aspect, oxygen-scavenging polymers are used to make the container itself or to coat the container, or as pellets to be added; e.g., as described in U.S. Pat. App. Pub. 20110008554, describing compositions comprising a polyester, a copolyester ether and an oxidation catalyst, wherein the copolyester ether comprises a polyether segment comprising poly(tetramethylene-co-alkylene ether). In one aspect, oxygen-scavenging polymers are used to make the container itself or to coat the container, or as pellets to be added; e.g., as described in U.S. Pat. App. Pub. 201000255231, describing a dispersed iron/salt particle in a polymer matrix, and an oxygen scavenging film with oxygen scavenging particulates.

Alternatively, in addition to or in place of the oxygen-scavenging mechanism, the air in the container can be replaced (completely or substantially) with nitrogen and/or other inert non-reactive gas or gases. In one aspect, the container simulates (creates) partially, substantially or completely an anaerobic environment.

In one aspect, the stool (e.g., fecal sample) is held in an aesthetically acceptable container that will not leak nor smell yet maintain an anaerobic environment. In one aspect, the container is sterile before receiving the fecal flora.

In one aspect, the compositions provided herein are maintained at room temperature during most or all of its preparation, transportation and/or storage at e.g., a "stool bank" or at the site where the transplantation will take place. For example, once delivered to a "processing stool bank" it is stored in at ambient temperature, e.g., room temperature. In one aspect, stabilizing agents such as glycerol are added to the harvested and/or stored material.

In one aspect, the stool is tested for various pathogens, as noted above. In one aspect, once cleared of infective agents, it is homogenized and filtered to remove large particles of matter. In one aspect, it is subdivided into desired volumes, e.g., which can be between 5 cc and 3 or more liters. For example, in one aspect, a container comprises a 50 gram (g) stool, which can be held in an appropriate oxygen resistant plastic, e.g., a metallized polyethylene terephthalate polyester film, or a metallized MYLAR™.

In one aspect, the FMT material is subject to homogenization.

In one aspect, compositions provided herein are placed into a container, e.g., a bag, that can be attached to a nasogastric or naso-duodenal tube to allow the contents to be infused e.g., into either a stomach, duodenum or the distal jejunum. Alternatively it can be kept in a container, e.g., a bag, which can be attached to an enema tip to be given as an enema.

In one aspect, to separate the non-bacterial components and produce a product that can be lyophilized and have a long shelf life, the stool can be homogenized and filtered from rough particulate matter. In one aspect, the microscopic fiber/nonliving matter is then separated from the bacteria. Several methods can be used, including e.g., recurrent filtration with filter sizes, e.g., coming down to the size of the bacterium.

In one aspect, different filters are used to isolate bacterial spp., or a technique as used by Williams in WO 2011/033310A1, which uses a crude technique of filtration with a gauze.

In one aspect, a filtration procedure for filtering whole stool is suitably used to reach the highest concentration of almost 100% bacteria. In one aspect, the filtering procedure is a two-step procedure suitably using glass fibre depth filters for initial clarification. In one aspect, the stool is filtered under positive pressure. In one aspect, this would be using a combination or sandwich configuration with a 30 micron PVDF filter. In one aspect, this sandwich procedure will be filtering the product under positive pressure. Later, membrane concentration can, in one aspect, be used as another step to reduce the volume of the filtrate. In one aspect, this can be done prior to freeze drying or spray drying under nitrogen cover.

Alternative membranes that can be used for filtration include, but not limited to, nylon filters, cellulose nitrate filters, polyethersulfone (PES) filters, polytetrafluoroethylene (PTFE) filters, TEFLON™ filters, mixed cellulose Ester filters, polycarbonate filters, polypropylene filters, Polyvinylchloride (PVC) filters or quartz filters. Various combinations of these can be used to achieve a high purity of bacteria with solids and liquid removed ready for freezing, spray-drying or lyophilisation.

For freeze-drying, in one aspect, bacteria are held in a liquid that will prevent bursting of cells on thawing. This can include various stabilizers, e.g., glycerol and appropriate buffers, and/or ethylene glycol. In one aspect, cryo-protectance uses final concentrations of stabilizer(s) of between about 10% to 80%, 20% to 70%, 30% to 60%, or 40% to 50%, depending on the stabilizer(s) used; in one aspect, this helps stabilize proteins by preventing formation of ice crystals that would otherwise destroy protein structures.

In one aspect, the methods and compositions of the disclosure comprise use of one cryoprotectant or a mixture of cryoprotectants, e.g., comprising: a dimethyl sulfoxide (DMSO) or equivalent; a glycerol, a polyethylene glycol (PEG) or equivalent; a polysaccharide; a sugar, or an amino acid, wherein the amino acid can comprise an alanine, a glycine, a proline, or the sugar can comprise a mannitol, a sucrose, a glucose, a lactose, a ribose or trehalose, or the polysaccharide can comprise a hydroxypropyl-β-cyclodextrin (HPβCD), or the cryoprotectant can comprise any combination of different cryoprotectant compounds. In one aspect, these cryoprotectants, e.g., trehalose, also function as a component upon reconstitution or as an additional agent prior to spray-drying or freeze-drying.

In one aspect, pharmaceutical compositions provided herein comprise lyophilized, cryodesiccated, freeze-dried or dehydrated microflora material from a formulation comprising one or more, two or more, three or more, four or more additives selected from the group consisting of trehalose, mannitol, sucrose, NaCl, and polysorbate 80, wherein the two or more components are effective in reducing or minimizing microbial viability loss in the microflora material. Used herein, additives include, but are not limited to, cryoprotectants, surfactants, and emulsifiers.

In one aspect, stabilizers that help reduce destruction of living bacteria include skim milk, erythritol, arabitol, sorbitol, glucose, fructose and other polyols. Polymers such as dextran and polyethylene glycol can also be used to stabilize the fecal bacterial cells.

In one aspect, an entire (or substantially entire) microbiota, or an isolated and/or treated (e.g., purified or isolated) fecal material and/or flora, is lyophilized or freeze dried, and the product is stored at ambient temperatures (e.g., room temperature), at a freezing temperature, or at between about 2° C. to 8° C. In one aspect, freeze-drying allows the majority of cells to remain viable, and produces a powdered form of the product that can be gently pulverized into a powder. The powder, or lyophilized or freeze-dried flora or isolate, then can be encapsulated into a carrier, e.g., a tablet, geltab, pill or capsule, e.g., an enteric-coated capsule, or placed into oil-filled capsules for ingestion. Alternatively, the freeze-dried or lyophilized product, or powder, can be reconstituted at ambient temperatures before delivery to an individual in e.g., a fluid, e.g., a sterile fluid, such as saline, a buffer or a media such as a fluid-glucose-cellobiose agar (RGCA) media.

In one aspect, an entire (or substantially entire) microbiota, or an isolated and/or treated (e.g., purified or isolated) fecal material and/or flora also can be spray-dried or foam-dried.

In one aspect, the entire (or substantially entire) microbiota, or isolated and/or treated fecal material and/or flora, is supplemented with wild type bacteria which has been derived from normal animal (e.g., human) flora and/or recombinantly treated bacteria, e.g., recombinant microorganisms that can synthesize a protein, small molecule or carbohydrate that has a self-protective or ameliorative effect; or recombinant microorganisms that can self-destruct when provided with an appropriate signal, e.g., a chemical delivered by ingestion.

In some aspects, pharmaceutical compositions provided herein include at least 2 different phyla of gut, colon or intestinal bacteria extracted or prepared from the gut, colon or intestine, and a cryoprotectant, wherein the phyla include a Bacteroidetes, a Firmicutes, a Proteobacteria a Tenericutes phylum, or a combination thereof, wherein optionally the phyla are chosen from Bacteroidetes, Firmicutes, Proteobacteria, Tenericutes, or a combination thereof, wherein the compositions, upon reconstitution with water, include no greater than about 0.05%, 0.1%, 0.2%, 0.3%, 0.4%, 0.5%, 0.6%, 0.7%, 0.8%, 0.9% 1%, 2%, 3%, 4%, 5%, 6%, 7%, 8%, 9%, or 10% weight non-living material/weight biological material, wherein the biological material includes human gut, colon or intestinal fecal microbes, and optionally the biological material includes human gut, colon or intestinal bacteria, and wherein optionally the compositions include a pharmaceutically acceptable carrier, and optionally the composition is a formulation for oral administration.

In some aspects, pharmaceutical compositions provided herein include an extract of human feces and a cryoprotectant, wherein the composition, upon reconstitution with water, is substantially odorless, wherein the composition includes biological material, and optionally wherein the biological material includes microbes, and wherein optionally the composition includes a pharmaceutically acceptable carrier, and optionally the composition is a formulation for oral administration.

In one aspect, the microflora material of a pharmaceutical composition provided herein comprises predominantly spores. In some aspects, at least 50%, 60%, 70%, 80%, 90%, 95%, 97%, 99% of the microbes in the microflora material are in a spore form. "Spore" refers to a microbial entity, which is in a dormant, non-vegetative and non-reproductive stage. Spores are generally resistant to environmental stress including, but not limited to radiation, desiccation, enzymatic treatment, temperature variation, nutrient deprivation, and chemical disinfectants. A collection of spores may be purified from a fecal sample, e.g. via ethanol or heat treatment or other known methods in the art. Alternatively, a collection of spores may be derived through culture methods starting from isolated spore former species or from a mixture of such species, either in vegetative or spore form.

In some aspects, pharmaceutical compositions provided herein comprise non-pathogenic Clostridia spores. In other aspects, pharmaceutical compositions also comprises viable non-pathogenic *Collinsella*. In some aspects, pharmaceutical compositions further comprise viable non-pathogenic organisms from at least one of the groups consisting of *Bacteroides*, Fusobacteria, Propionibacteria, Lactobacilli, anaerobic cocci, *Ruminococcus*, *E. coli*, *Gemmiger*, Desulfomonas, *Peptostreptococcus*, and Bifidobacteria. In further aspects, pharmaceutical compositions further comprises one or more viable non-pathogenic microorganisms selected from the group consisting of a *Bacteroides fragilis* ss. Vulgatus, *Collinsella aerofaciens*, *Bacteroides fragilis* ss. Thetaiotaomicron, *Peptostreptococcus productus* II, *Parabacteroides distasonis*, *Fusobacterium prausnitzii*, *Coprococcus eutactus*, *Collinsella aerofaciens* III, *Peptostreptococcus productus* I, *Ruminococcus bromii*, *Bifidobacterium adolescentis*, *Gemmiger formicilis*, *Bifidobacterium longum*, *Eubacterium siraeum*, *Ruminococcus torques*, *Eubacterium rectale*, *Eubacterium eligens*, *Bacteroides eggerthii*, *Clostridium leptum*, *Bacteroides fragilis* ss. A, *Eubacterium biforme*, *Bifidobacterium infantis*, *Eubacterium rectale Coprococcus comes*, *Pseudoflavonifractor capillosus*, *Ruminococcus albus*, *Dorea formicigenerans*, *Eubacterium hallii*, *Eubacterium ventriosum* I, *Fusobacterium russi*, *Ruminococcus obeum*, *Eubacterium rectale*, *Clostridium ramosum*, *Lactobacillus leichmannii*, *Ruminococcus callidus*, *Butyrivibrio crossotus*, *Acidaminococcus fermentans*, *Eubacterium ventriosum*, *Bacteroides fragilis* ss. *fragilis*, *Bacteroides* AR, *Coprococcus catus*, *Aerostipes hadrus*, *Eubacterium cylindroides*, *Eubacterium ruminantium*, *Eubacterium* CH-1, *Staphylococcus epidermidis*, *Peptostreptococcus* BL, *Eubacterium limosum*, *Tissirella praeacuta*, *Bacteroides* L, *Fusobacterium mortiferum* I, *Fusobacterium naviforme*, *Clostridium innocuum*, *Clostridium ramosum*, *Propionibacterium acnes*, *Ruminococcus flavefaciens*, *Ruminococcus* AT, Peptococcus AU-1, *Bacteroides fragilis* ss. *ovatus*, -ss. d, -ss. f; *Bacteroides* L-1, L-5; *Fusobacterium nucleatum*, *Fusobacterium mortiferum*, *Escherichia coli*, *Gemella morbillorum*, *Finegoldia magnus*, Peptococcus G, -AU-2; *Streptococcus intermedius*, *Ruminococcus lactaris*, *Ruminococcus* CO *Gemmiger* X, *Coprococcus* BH, —CC; *Eubacterium tenue*, *Eubacterium ramulus*, *Bacteroides clostridiiformis* ss. *clostridliformis*, *Bacteroides coagulans*, *Prevotella oralis*, *Prevotella rumini-* cola, *Odoribacter splanchnicus, Desuifomonas pigra, Lactobacillus* G, *Succinivibrio* A, and a combination thereof.

In some aspects, pharmaceutical compositions provided herein comprise non-pathogenic Clostridia spores and viable non-pathogenic *Collinsella* without organisms from at least one of the groups consisting of *Bacteroides*, Fusobacteria, Propionibacteria, Lactobacilli, anaerobic cocci, *Ruminococcus, E. coli, Gemmiger*, Desulfomonas, *Peptostreptococcus*, and Bifidobacteria. In other aspects, pharmaceutical compositions comprise no viable non-pathogenic microorganisms selected from the group consisting of a *Bacteroides fragilis* ss. Vulgatus, *Collinsella aerofaciens, Bacteroides fragilis* ss. Thetaiotaomicron, *Peptostreptococcus productus* II, *Parabacteroides distasonis, Fusobacterium prausnitzii, Coprococcus eutactus, Collinsella aerofaciens* III, *Peptostreptococcus productus* I, *Ruminococcus* bromii, *Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ss. A, *Eubacterium biforme, Bifidobacterium infantis, Eubacterium rectale Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ss. *fragilis, Bacteroides* AR, *Coprococcus catus, Aerostipes hadrus, Eubacterium cylindroides, Eubacterium ruminantium, Eubacterium* CH-1, *Staphylococcus epidermidis, Peptostreptococcus* BL, *Eubacterium limosum, Tissirella praeacuta, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Bacteroides fragilis* ss. *ovatus*, -ss. d, -ss. f; *Bacteroides* L-1, L-5; *Fusobacterium nucleatum, Fusobacterium mortiferum, Escherichia coli, Gemella morbillorum, Finegoldia magnus*, *Peptococcus* G, -AU-2; *Streptococcus intermedius, Ruminococcus lactaris, Ruminococcus* CO *Gemmiger* X, *Coprococcus* BH, —CC; *Eubacterium tenue, Eubacterium ramulus, Bacteroides clostridiiformis* ss. clostridhformis, *Bacteroides coagulans, Prevotella oralis, Prevotella ruminicola, Odoribacter splanchnicus, Desuifomonas pigra, Lactobacillus* G, *Succinivibrio* A, and a combination thereof.

In one aspect, the transplantation product (e.g., a composition provided herein) is delivered by an infusion, e.g., through the rectum, stoma or down the upper gastrointestinal (GI) tract, or it can be used in a suppository pill, tablet or encapsulated form, e.g., with an enteric-coated graded release capsule or a tablet, e.g., with the addition of excipients. In one aspect, the transplantation product is administered as a suppository to give the highest concentration in the rectum.

In one aspect, the transplantation product (e.g., a composition provided herein, e.g., comprising an isolated or purified fecal flora or an entire (or substantially entire) microbiota) is stored at room temperature before or during delivery to an individual, e.g., in a fluid, e.g., a sterile fluid, such as saline, a buffer or a media such as a fluid-glucose-cellobiose agar (RGCA) media.

In one aspect, the compositions provided herein are used to ameliorate, stabilize, prevent and/or treat: various gastrointestinal conditions, e.g., *C. difficile* infection, *C. perfringens* welchii and other *Clostridium* infections, irritable bowel syndrome, constipation, pouchitis, Crohn's disease and microscopic colitis; neurological conditions such as autism, Parkinson's disease, myoclonus dystonia, autism, amyotrophic lateral sclerosis and multiple sclerosis, Grand mal seizures or petit mal seizures. In one aspect, the neurological conditions are treated by encapsulated or frozen material. In one aspect, for colitis patients, recurrent administration is required to suppress and reverse the inflammatory bowel disease and irritable bowel syndrome.

In one aspect, a crude collected stool is filtered and/or homogenized, and then its bacterial cells are separated (e.g., from the "crud" which contains the undigested food and fiber) by plasmapheresis, centrifugation, celltrifuge, column chromatography (e.g., affinity chromatography), immunoprecipitation (e.g., antibodies fixed to a solid surface, such as beads or a plate). Centrifugation, including use of a "celltrifuge" (e.g., a Baxter model MEDIFUGE 1215™) are processes that involve centrifugal force to separate mixtures. For "celltrifugation", the densest components will then fly to the outside of the spinning plates while the rest of the components will migrate to the axis. The effect of the gravitational force will be increased by spinning the flattened product between rapidly moving glass plates. The centrifuge or celltrifuge can be set up such that the stool will be diluted adequately and set on a spinning cycle and collection of cells will occur only peripherally on the centrifuge.

In one aspect, wild type bacterial cells (including e.g., an entire (or substantially entire) microbiota) separated or purified e.g., by centrifugation, celltrifugation, plasmapheresis and the like. In one aspect, this material is stored at room temperature in a container, e.g., a bag, which can then be used to infuse through a colonoscope, naso-duodenal or nasogastric tube. In one aspect, it can be delivered to a facility (e.g., a hospital pharmacy) to be kept at room temperature, e.g., at between about 20° C. to 26° C. In one aspect, compositions provided herein are used either in a solution, gels, geltabs, pills, capsules or tablets, or suppositories, e.g., to be reconstituted later as an enema or infuse set through a colonoscope.

In one aspect, solutions, gels, geltabs, pills, capsules or tablets comprising compositions provided herein (e.g., isolated or purified fecal flora or an entire (or substantially entire) microbiota) can be taken long term, e.g., on a daily basis long term, e.g., for one, two, three or four weeks or months or more, to treat, stabilize, ameliorate or prevent a chronic and/or an immune condition such as e.g., autism, persistent infection, rheumatoid arthritis, systemic lupus erythematosus, autoimmune renal diseases, e.g., nephritis, severe obstruction, inflammatory bowel disease (IBD), irritable bowel syndrome (IBS), and other conditions set forth herein.

In one aspect, this application provides for the following embodiments:

Embodiment 1. A pharmaceutical composition comprising a lyophilized fecal microbe preparation comprising a lyophilization formulation comprising at least about 10% trehalose, wherein said lyophilization formulation is capable of providing a cell integrity maintenance ratio of at least about 20%.

Embodiment 2. The pharmaceutical composition of embodiment 1, wherein said lyophilization formulation comprises at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20%, at least about 22.5%, at least about 25%, at least about 27.5%, at least about 30%, at least about 32.5%, at least about 35%, at least about 37.5%, at least about 40%, at least about 42.5%, at least about 45%, at least about 47.5%, at least about 50%, at least about 52.5%, at least about 55%, at least about 57.5%, or at least about 60% trehalose.

Embodiment 3. The pharmaceutical composition of embodiment 1, wherein said lyophilization formulation comprises between about 12.5% and about 60%, between about 13% and about 60%, between about 13.5% and about 60%, between about 14% and about 60%, between about 14.5% and about 60%, between about 15% and about 60%, between about 15.5% and about 60%, between about 16% and about 60%, between about 16.5% and about 60%, between about 17% and about 60%, between about 17.5% and about 60%, between about 18% and about 60%, between about 18.5% and about 60%, between about 19% and about 60%, between about 19.5% and about 60%, between about 20% and about 60%, between about 22.5% and about 60%, between about 25% and about 60%, between about 27.5% and about 60%, between about 30% and about 60%, between about 32.5% and about 60%, between about 35% and about 60%, or between about 37.5% and about 60% trehalose.

Embodiment 4. The pharmaceutical composition of embodiment 1, wherein said lyophilization formulation comprises between about 12.5% and about 40%, between about 13% and about 40%, between about 13.5% and about 40%, between about 14% and about 40%, between about 14.5% and about 40%, between about 15% and about 40%, between about 15.5% and about 40%, between about 16% and about 40%, between about 16.5% and about 40%, between about 17% and about 40%, between about 17.5% and about 40%, between about 18% and about 40%, between about 18.5% and about 40%, between about 19% and about 40%, between about 19.5% and about 40%, between about 20% and about 40%, between about 22.5% and about 40%, between about 25% and about 40%, between about 27.5% and about 40%, between about 30% and about 40%, between about 32.5% and about 40%, between about 35% and about 40%, or between about 37.5% and about 40% trehalose.

Embodiment 5. The pharmaceutical composition of embodiment 1, wherein said lyophilization formulation comprises between about 12.5% and about 30%, between about 13% and about 30%, between about 13.5% and about 30%, between about 14% and about 30%, between about 14.5% and about 30%, between about 15% and about 30%, between about 15.5% and about 30%, between about 16% and about 30%, between about 16.5% and about 30%, between about 17% and about 30%, between about 17.5% and about 30%, between about 18% and about 30%, between about 18.5% and about 30%, between about 19% and about 30%, between about 19.5% and about 30%, between about 20% and about 30%, between about 22.5% and about 30%, between about 25% and about 30%, or between about 27.5% and about 30% trehalose.

Embodiment 6. The pharmaceutical composition of embodiment 1, wherein said lyophilization formulation comprises between about 12.5% and about 25%, between about 13% and about 25%, between about 13.5% and about 25%, between about 14% and about 25%, between about 14.5% and about 25%, between about 15% and about 25%, between about 15.5% and about 25%, between about 16% and about 25%, between about 16.5% and about 25%, between about 17% and about 25%, between about 17.5% and about 25%, between about 18% and about 25%, between about 18.5% and about 25%, between about 19% and about 25%, between about 19.5% and about 25%, between about 20% and about 25%, or between about 22.5% and about 25% trehalose.

Embodiment 7. The pharmaceutical composition of embodiment 1, wherein said lyophilization formulation comprises between about 12.5% and about 20%, between about 13% and about 20%, between about 13.5% and about 20%, between about 14% and about 20%, between about 14.5% and about 20%, between about 15% and about 20%, between about 15.5% and about 20%, between about 16% and about 20%, between about 16.5% and about 20%, between about 17% and about 20%, between about 17.5% and about 20%, between about 18% and about 20%, between about 18.5% and about 20%, between about 19% and about 20%, or between about 19.5% and about 20% trehalose.

Embodiment 8. The pharmaceutical composition of embodiment 1, wherein said lyophilization formulation comprises between about 12.5% and about 17.5%, between about 13% and about 17.5%, between about 13.5% and about 17.5%, between about 14% and about 17.5%, between about 14.5% and about 17.5%, between about 15% and about 17.5%, between about 15.5% and about 17.5%, between about 16% and about 17.5%, between about 16.5% and about 17.5%, or between about 17% and about 17.5% trehalose.

Embodiment 9. The pharmaceutical composition of embodiment 1, wherein said lyophilization formulation comprises between about 12.5% and about 17.5%, between about 13% and about 17%, between about 13.5% and about 16.5%, between about 14% and about 16%, or between about 14.5% and about 15.5% trehalose.

Embodiment 10. The pharmaceutical composition of embodiment 1, wherein said lyophilization formulation comprises about 15% trehalose.

Embodiment 11. The pharmaceutical composition of embodiment 1, wherein said lyophilization formulation comprises 15% trehalose.

Embodiment 12. The pharmaceutical composition of any one of embodiments 1 to 11, wherein said lyophilization formulation is capable of providing a cell integrity maintenance ratio of at least about 22.5%, at least about 25%, at least about 27.5%, at least about 30%, at least about 32.5%, at least about 35%, at least about 37.5%, at least about 40%, at least about 42.5%, at least about 45%, at least about 47.5%, at least about 50%, at least about 52.5%, at least about 55%, at least about 57.5%, at least about 60%, at least about 62.5%, at least about 65%, at least about 67.5%, at least about 70%, at least about 72.5%, at least about 75%, at least about 77.5%, at least about 80%, at least about 82.5%, at least about 85%, at least about 87.5%, at least about 90%, at least about 92.5%, or at least about 95%.

Embodiment 13. The pharmaceutical composition of any one of embodiments 1 to 11, wherein said lyophilization formulation is capable of providing a cell integrity maintenance ratio of between about 22.5% and about 90%, of between about 25% and about 90%, of between about 27.5% and about 90%, of between about 30% and about 90%, between about 32.5% and about 90%, between about 35% and about 90%, between about 37.5% and about 90%, between about 40% and about 90%, between about 42.5% and about 90%, between about 45% and about 90%, between about 47.5% and about 90%, between about 50% and about 90%, between about 52.5% and about 90%, between about 55% and about 90%, between about 57.5% and about 90%, between about 60% and about 90%, between about 62.5% and about 90%, between about 65% and about 90%, between about 67.5% and about 90%, between about 70% and about 90%, between about 72.5% and about 90%, between about 75% and about 90%, between about 77.5% and about 90%, between about 80% and about 90%, between about 82.5% and about 90%, between about 85% and about 90%, or between about 87.5% and about 90%.

Embodiment 14. The pharmaceutical composition of any one of embodiments 1 to 11, wherein said lyophilization formulation is capable of providing a cell integrity maintenance ratio of between about 22.5% and about 80%, of between about 25% and about 80%, of between about 27.5% and about 80%, of between about 30% and about 80%, between about 32.5% and about 80%, between about 35% and about 80%, between about 37.5% and about 80%, between about 40% and about 80%, between about 42.5% and about 80%, between about 45% and about 80%, between about 47.5% and about 80%, between about 50% and about 80%, between about 52.5% and about 80%, between about 55% and about 80%, between about 57.5% and about 80%, between about 60% and about 80%, between about 62.5% and about 80%, between about 65% and about 80%, between about 67.5% and about 80%, between about 70% and about 80%, between about 72.5% and about 80%, between about 75% and about 80%, or between about 77.5% and about 80%.

Embodiment 15. The pharmaceutical composition of any one of embodiments 1 to 11, wherein said lyophilization formulation is capable of providing a cell integrity maintenance ratio of between about 22.5% and about 70%, of between about 25% and about 70%, of between about 27.5% and about 70%, of between about 30% and about 70%, between about 32.5% and about 70%, between about 35% and about 70%, between about 37.5% and about 70%, between about 40% and about 70%, between about 42.5% and about 70%, between about 45% and about 70%, between about 47.5% and about 70%, between about 50% and about 70%, between about 52.5% and about 70%, between about 55% and about 70%, between about 57.5% and about 70%, between about 60% and about 70%, between about 62.5% and about 70%, between about 65% and about 70%, or between about 67.5% and about 70%.

Embodiment 16. The pharmaceutical composition of any one of embodiments 1 to 11, wherein said lyophilization formulation is capable of providing a cell integrity maintenance ratio of between about 22.5% and about 60%, of between about 25% and about 60%, of between about 27.5% and about 60%, of between about 30% and about 60%, between about 32.5% and about 60%, between about 35% and about 60%, between about 37.5% and about 60%, between about 40% and about 60%, between about 42.5% and about 60%, between about 45% and about 60%, between about 47.5% and about 60%, between about 50% and about 60%, between about 52.5% and about 60%, between about 55% and about 60%, or between about 57.5% and about 60%.

Embodiment 17. The pharmaceutical composition of any one of embodiments 1 to 11, wherein said lyophilization formulation is capable of providing a cell integrity maintenance ratio of between about 22.5% and about 50%, of between about 25% and about 50%, of between about 27.5% and about 50%, of between about 30% and about 50%, between about 32.5% and about 50%, between about 35% and about 50%, between about 37.5% and about 50%, between about 40% and about 50%, between about 42.5% and about 50%, between about 45% and about 50%, or between about 47.5% and about 50%.

Embodiment 18. The pharmaceutical composition of any one of embodiments 1 to 11, wherein said lyophilization formulation is capable of providing a cell integrity maintenance ratio between about 22.5% and about 25%, between about 27.5% and about 30%, between about 30% and 32.5%, between about 32.5% and about 80%, between about 35% and about 77.5%, between about 37.5% and about 75%, between about 40% and about 67.5%, between about 42.5% and about 65%, between about 45% and about 62.5%, between about 47.5% and about 60%, between about 50% and about 57.5%, or between about 52.5% and about 55%.

Embodiment 19. The pharmaceutical composition of any one of embodiments 1 to 11, wherein said lyophilization formulation is capable of providing a cell integrity maintenance ratio of between about 32.5% and about 90%, between about 35% and about 87.5%, between about 37.5% and about 85%, between about 40% and about 82.5%, between about 42.5% and about 77.5%, between about 45% and about 75%, between about 47.5% and about 72.5%, between about 50% and about 70%, between about 52.5% and about 67.5%, between about 55% and about 65%, or between about 57.5% and about 62.5%.

Embodiment 20. The pharmaceutical composition of any one of embodiments 1 to 11, wherein said lyophilization formulation is capable of a post-lyophilization cell membrane integrity percentage of at least about 22.5%, at least about 25%, at least about 27.5%, at least about 30%, at least about 32.5%, at least about 35%, at least about 37.5%, at least about 40%, at least about 42.5%, at least about 45%, at least about 47.5%, at least about 50%, at least about 52.5%, at least about 55%, at least about 57.5%, at least about 60%, at least about 62.5%, at least about 65%, at least about 67.5%, at least about 70%, at least about 72.5%, at least about 75%, at least about 77.5%, at least about 80%.

Embodiment 21. The pharmaceutical composition of any one of embodiments 1 to 11, wherein said lyophilization formulation is capable of a post-lyophilization cell membrane integrity percentage of between about 20% and about 80%, between about 22.5% and about 80%, between about 25% and about 80%, between about 27.5% and about 80%, between about 30% and about 80%, between about 32.5% and about 80%, between about 35% and about 80%, between about 37.5% and about 80%, between about 40% and about 80%, between about 42.5% and about 80%, between about 45% and about 80%, between about 47.5% and about 80%, between about 50% and about 80%, between about 52.5% and about 80%, between about 55% and about 80%, between about 57.5% and about 80%, between about 60% and about 80%, between about 62.5% and about 80%, between about 65% and about 80%, between about 67.5% and about 80%, between about 70% and about 80%, between about 72.5% and about 80%, between about 75% and about 80%, or between about 77.5% and about 80%.

Embodiment 22. The pharmaceutical composition of any one of embodiments 1 to 11, wherein said lyophilization formulation is capable of a post-lyophilization cell membrane integrity percentage of between about 20% and about 70%, between about 22.5% and about 70%, between about 25% and about 70%, between about 27.5% and about 70%, between about 30% and about 70%, between about 32.5% and about 70%, between about 35% and about 70%, between about 37.5% and about 70%, between about 40% and about 70%, between about 42.5% and about 70%, between about 45% and about 70%, between about 47.5% and about 70%, between about 50% and about 70%, between about 52.5% and about 70%, between about 55% and about 70%, between about 57.5% and about 70%, between about 60% and about 70%, between about 62.5% and about 70%, between about 65% and about 70%, or between about 67.5% and about 70%.

Embodiment 23. The pharmaceutical composition of any one of embodiments 1 to 11, wherein said lyophilization formulation is capable of a post-lyophilization cell membrane integrity percentage of between about 20% and about 60%, between about 22.5% and about 60%, between about 25% and about 60%, between about 27.5% and about 60%, between about 30% and about 60%, between about 32.5% and about 60%, between about 35% and about 60%, between about 37.5% and about 60%, between about 40% and about 60%, between about 42.5% and about 60%, between about 45% and about 60%, between about 47.5% and about 60%, between about 50% and about 60%, between about 52.5% and about 60%, between about 55% and about 60%, or between about 57.5% and about 60%.

Embodiment 24. The pharmaceutical composition of any one of embodiments 1 to 11, wherein said lyophilization formulation is capable of a post-lyophilization cell membrane integrity percentage of between about 20% and about 50%, between about 22.5% and about 50%, between about 25% and about 50%, between about 27.5% and about 50%, between about 30% and about 50%, between about 32.5% and about 50%, between about 35% and about 50%, between about 37.5% and about 50%, between about 40% and about 50%, between about 42.5% and about 50%, between about 45% and about 50%, or between about 47.5% and about 50%.

Embodiment 25. The pharmaceutical composition of any one of embodiments 1 to 11, wherein said lyophilization formulation is capable of a post-lyophilization cell membrane integrity percentage of between about 20% and about 40%, between about 22.5% and about 40%, between about 25% and about 40%, between about 27.5% and about 40%, between about 30% and about 40%, between about 32.5% and about 40%, between about 35% and about 40%, or between about 37.5% and about 40%.

Embodiment 26. The pharmaceutical composition of any one of embodiments 1 to 11, wherein said lyophilization formulation is capable of a post-lyophilization cell membrane integrity percentage of between about 32.5% and about 80%, between about 35% and about 77.5%, between about 37.5% and about 75%, between about 40% and about 67.5%, between about 42.5% and about 65%, between about 45% and about 62.5%, between about 47.5% and about 60%, between about 50% and about 57.5%, or between about 52.5% and about 55%.

Embodiment 27. The pharmaceutical composition of any one of embodiments 1 to 11, wherein said lyophilization formulation is capable of a post-lyophilization cell membrane integrity percentage of between about 32.5% and about 90%, between about 35% and about 87.5%, between about 37.5% and about 85%, between about 40% and about 82.5%, between about 42.5% and about 77.5%, between about 45% and about 75%, between about 47.5% and about 72.5%, between about 50% and about 70%, between about 52.5% and about 67.5%, between about 55% and about 65%, or between about 57.5% and about 62.5%.

Embodiment 28. The pharmaceutical composition of any one of embodiments 1 to 11, wherein said lyophilization formulation is capable of providing a post-lyophilization cell membrane integrity percentage of between about 25% and about 55%, between about 27.5% and about 52.5%, between about 30% and about 50%, between about 32.5% and about 47.5%, between about 35% and about 45%, or between about 37.5% and about 42.5%.

Embodiment 29. The pharmaceutical composition of any one of embodiments 1 to 28, wherein said lyophilization formulation further comprises a reducing agent.

Embodiment 30. The pharmaceutical composition of embodiment 29, wherein said reducing agent is cysteine selected from the group consisting of D-cysteine and L-cysteine, or sodium abscorbate.

Embodiment 31. The pharmaceutical composition of embodiment 30, wherein said cysteine is at a concentration of at least about 0.025%.

Embodiment 32. The pharmaceutical composition of embodiment 30, wherein said cysteine is at a concentration of about 0.025%.

Embodiment 33. The pharmaceutical composition of embodiment 30, wherein said cysteine is at a concentration of 0.025%.

Embodiment 34. The pharmaceutical composition of embodiment 30, wherein said cysteine is at a concentration of at least about 0.001%, at least about 0.005%, at least about 0.01%, at least about 0.015%, at least about 0.02%, at least about 0.025%, at least about 0.03%, at least about 0.035%, at least about 0.04%, at least about 0.045%, at least about 0.05%, at least about 0.055%, at least about 0.06%, at least about 0.065%, at least about 0.07%, at least about 0.075%, at least about 0.08%, at least about 0.085%, at least about 0.09%, at least about 0.095%, at least about 0.1%, at least about 0.12%, at least about 0.14%, at least about 0.16%, at least about 0.18%, at least about 0.2%, at least about 0.25%, at least about 0.3%, at least about 0.4%, at least about 0.5%, at least about 0.6%, at least about 0.7%, at least about 0.8%, at least about 0.9%, at least about 1%, at least about 2%, at least about 4%, at least about 6%, at least about 8%, at least about 10%, at least about 12%, at least about 14%, at least about 16%, at least about 18%, at least about 20%, at least about 22%, at least about 24%, or at least about 26%.

Embodiment 35. The pharmaceutical composition of embodiment 30, wherein said cysteine is at a concentration of between about 0.005% and about 0.1%, between about 0.01% and about 0.1%, between about 0.015% and about 0.1%, between about 0.02% and about 0.1%, between about 0.025% and about 0.1%, between about 0.03% and about 0.1%, between about 0.035% and about 0.1%, between about 0.04% and about 0.1%, between about 0.045% and about 0.1%, between about 0.05% and about 0.1%, between about 0.055% and about 0.1%, between about 0.06% and about 0.1%, between about 0.065% and about 0.1%, between about 0.07% and about 0.1%, between about 0.075% and about 0.1%, between about 0.08% and about 0.1%, between about 0.085% and about 0.1%, between about 0.09% and about 0.1%, between about 0.095% and about 0.1%.

Embodiment 36. The pharmaceutical composition of embodiment 30, wherein said cysteine is at a concentration of between about 0.005% and about 0.08%, between about 0.01% and about 0.08%, between about 0.015% and about 0.08%, between about 0.02% and about 0.08%, between about 0.025% and about 0.08%, between about 0.03% and about 0.08%, between about 0.035% and about 0.08%, between about 0.04% and about 0.08%, between about 0.045% and about 0.08%, between about 0.05% and about 0.08%, between about 0.055% and about 0.08%, between about 0.06% and about 0.08%, between about 0.065% and about 0.08%, between about 0.07% and about 0.08%, or between about 0.075% and about 0.08%.

Embodiment 37. The pharmaceutical composition of embodiment 30, wherein said cysteine is at a concentration of between about 0.005% and about 0.06%, between about 0.01% and about 0.06%, between about 0.015% and about 0.06%, between about 0.02% and about 0.06%, between about 0.025% and about 0.06%, between about 0.03% and about 0.06%, between about 0.035% and about 0.06%, between about 0.04% and about 0.06%, between about 0.045% and about 0.06%, between about 0.05% and about 0.06%, or between about 0.055% and about 0.06%.

Embodiment 38. The pharmaceutical composition of embodiment 30, wherein said cysteine is at a concentration of between about 0.005% and about 0.04%, between about 0.01% and about 0.04%, between about 0.015% and about 0.04%, between about 0.02% and about 0.04%, between about 0.025% and about 0.04%, between about 0.03% and about 0.04%, or between about 0.035% and about 0.04%.

Embodiment 39. The pharmaceutical composition of embodiment 30, wherein said cysteine is at a concentration of between about 0.005% and about 0.06%, between about 0.01% and about 0.05%, between about 0.015% and about 0.04%, or between about 0.02% and about 0.03%.

Embodiment 40. The pharmaceutical composition of any one of the preceding embodiments, wherein said fecal microbe preparation comprises a non-selected and substantially complete fecal microbiota preparation from a single donor.

Embodiment 41. The pharmaceutical composition of embodiment 40, wherein the weight ratio between fecal-derived non-living material and fecal-derived biological material in said fecal microbiota preparation is no greater than 20%.

Embodiment 42. The pharmaceutical composition of embodiment 40, wherein the preparation of said fecal microbe preparation involves a treatment selected from the group consisting of ethanol treatment, detergent treatment, heat treatment, irradiation, homogenization, sonication, and combination thereof.

Embodiment 43. The pharmaceutical composition of embodiment 40, wherein the preparation of said fecal microbe preparation involves a separation step selected from the group consisting of filtering, sieving, density gradients, filtration, chromatography, sedimentation, centrifugation, and a combination thereof.

Embodiment 44. The pharmaceutical composition of embodiment 40, wherein after at least 12 weeks of storage at ambient temperature or lower said fecal microbiota preparation is capable of maintaining at least 60% cell viability relative to the initial cell viability immediately prior to storage.

Embodiment 45. The pharmaceutical composition of embodiment 44, wherein after at least 12 weeks of storage at ambient temperature or lower said fecal microbiota preparation is capable of maintaining about 60% to about 80% cell viability relative to the initial cell viability at the start of said storage.

Embodiment 46. The pharmaceutical composition of embodiment 44, wherein the cell viability is measured by assessing cell membrane permeability via a combination of membrane permeant and impermeant DNA dyes stains or non-DNA binding dyes.

Embodiment 47. The pharmaceutical composition of embodiment 40, wherein said lyophilized formulation further comprises one or more cryoprotectants selected from the group consisting of dimethyl sulfoxide (DMSO), glycerol, polyethylene glycol (PEG), alanine, glycine, proline, mannitol, sucrose, glucose, lactose, ribose, hydroxypropyl-β-cyclodextrin (HPβCD), and any combination thereof.

Embodiment 48. The pharmaceutical composition of embodiment 40, wherein said pharmaceutical composition is for oral administration.

Embodiment 49. The pharmaceutical composition of embodiment 40, wherein said pharmaceutical composition is formulated as a geltab, pill, microcapsule, capsule, or tablet.

Embodiment 50. The pharmaceutical composition of embodiment 40, wherein every 200 mg of said pharmaceutical composition comprises a pharmacologically active dose of microbes or spores selected from the group consisting of $10^3$ to $10^{15}$, $10^4$ to $10^{15}$, $10^5$ to $10^{15}$, $10^6$ to $10^{15}$, $10^7$ to $10^{15}$, $10^8$ to $10^{15}$, $10^3$ to $10^{14}$, $10^4$ to $10^{14}$, $10^5$ to $10^{14}$, $10^6$ to $10^{14}$, $10^7$ to $10^{14}$, $10^8$ to $10^{14}$, $10^4$ to $10^{13}$, $10^5$ to $10^{12}$, $10^6$ to $10^{11}$, $10^7$ to $10^{10}$, $10^8$ to $10^9$, $10^3$ to $10^{13}$, $10^3$ to $10^{12}$, $10^3$ to $10^{11}$, $10^3$ to $10^{10}$, $10^3$ to $10^9$, $10^3$ to $10^8$, $10^3$ to $10^7$, $10^3$ to $10^6$, $10^3$ to $10^5$, and $10^3$ to $10^4$ cfu or total cell count.

Embodiment 51. The pharmaceutical composition of embodiment 40, wherein said fecal microbe preparation has at least about 10%, 20%, 30%, 40%, 50%, 60%, 70%, 80%, 85%, 90%, 95%, 99%, or 99.5% microbes in a spore form.

Embodiment 52. The pharmaceutical composition of embodiment 40, wherein said pharmaceutical composition is effective for treating one or more disorders selected from the group consisting of recurrent or primary C. difficile infection, autism spectrum disorder (ASD), ulcerative colitis, Crohn's disease, and irritable bowel syndrome.

Embodiment 53. A lyophilized fecal microbe composition comprising a lyophilization formulation comprising trehalose and cysteine, wherein said lyophilization formulation is capable of maintaining at least about 30% cell viability immediately post lyophilization relative to a pre-lyophilization cell viability.

Embodiment 54. The lyophilized fecal microbe composition of embodiment 53, wherein said lyophilization formulation comprises at least 15% trehalose and at least 0.025% L-cysteine.

Embodiment 55. A lyophilized fecal microbiota pharmaceutical composition comprising a lyophilization formulation comprising at least about 12.5% trehalose, wherein said lyophilization formulation is capable of providing a cell integrity maintenance ratio of at least 35%.

Embodiment 56. A method of preparing a lyophilized fecal microbe preparation, said method comprising: a. obtaining a liquid fecal microbe preparation in a lyophilization formulation comprising between 10% and 20% trehalose; and b. freeze-drying said liquid fecal microbe preparation, wherein said lyophilization formulation is capable of providing a cell integrity maintenance ratio of at least about 30%.

Embodiment 57. The method of embodiment 56, wherein said lyophilization formulation comprises between 12.5% and 17.5% trehalose.

Embodiment 58. The method of embodiment 56, wherein said lyophilization formulation comprises at least about 15% trehalose.

Embodiment 59. The method of embodiment 56, wherein said lyophilization formulation comprises about 15% trehalose.

Embodiment 60. The method of embodiment 56, wherein said lyophilization formulation further comprises L-cysteine.

Embodiment 61. The method of embodiment 60, wherein said lyophilization formulation comprises at least about 0.02% L-cysteine.

Embodiment 62. The method of embodiment 60, wherein said lyophilization formulation comprises about 0.025% L-cysteine.

Embodiment 63. A frozen fecal microbe composition comprising trehalose, wherein said frozen fecal microbe composition is capable of being thawed at least once without loss of microbial cell membrane integrity of more than 50%.

Embodiment 64. The frozen fecal microbe composition of embodiment 63, wherein said being thawed at least once is thawed at least 2, 3, 4, 5, or 6 times.

Embodiment 65. The frozen fecal microbe composition of embodiment 63, wherein said frozen fecal microbe composition is capable of being thawed at least once without loss of microbial cell membrane integrity of more than 40%, more than 35%, more than 30%, more than 25%, more than 20%, more than 15%, more than 10%, or more than 5%.

Embodiment 66. The frozen fecal microbe composition of embodiment 63, wherein said composition comprises at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20%, at least about 22.5%, at least about 25%, at least about 27.5%, at least about 30%, at least about 32.5%, at least about 35%, at least about 37.5%, at least about 40%, at least about 42.5%, at least about 45%, at least about 47.5%, at least about 50%, at least about 52.5%, at least about 55%, at least about 57.5%, or at least about 60% trehalose.

Embodiment 67. The frozen fecal microbe composition of embodiment 63, wherein said composition comprises between about 12.5% and about 60%, between about 13% and about 60%, between about 13.5% and about 60%, between about 14% and about 60%, between about 14.5% and about 60%, between about 15% and about 60%, between about 15.5% and about 60%, between about 16% and about 60%, between about 16.5% and about 60%, between about 17% and about 60%, between about 17.5% and about 60%, between about 18% and about 60%, between about 18.5% and about 60%, between about 19% and about 60%, between about 19.5% and about 60%, between about 20% and about 60%, between about 22.5% and about 60%, between about 25% and about 60%, between about 27.5% and about 60%, between about 30% and about 60%, between about 32.5% and about 60%, between about 35% and about 60%, or between about 37.5% and about 60% trehalose.

Embodiment 68. The frozen fecal microbe composition of embodiment 63, wherein said composition comprises between about 12.5% and about 40%, between about 13% and about 40%, between about 13.5% and about 40%, between about 14% and about 40%, between about 14.5% and about 40%, between about 15% and about 40%, between about 15.5% and about 40%, between about 16% and about 40%, between about 16.5% and about 40%, between about 17% and about 40%, between about 17.5% and about 40%, between about 18% and about 40%, between about 18.5% and about 40%, between about 19% and about 40%, between about 19.5% and about 40%, between about 20% and about 40%, between about 22.5% and about 40%, between about 25% and about 40%, between about 27.5% and about 40%, between about 30% and about 40%, between about 32.5% and about 40%, between about 35% and about 40%, or between about 37.5% and about 40% trehalose.

Embodiment 69. The frozen fecal microbe composition of embodiment 63, wherein said composition comprises between about 12.5% and about 30%, between about 13% and about 30%, between about 13.5% and about 30%, between about 14% and about 30%, between about 14.5% and about 30%, between about 15% and about 30%, between about 15.5% and about 30%, between about 16% and about 30%, between about 16.5% and about 30%, between about 17% and about 30%, between about 17.5% and about 30%, between about 18% and about 30%, between about 18.5% and about 30%, between about 19% and about 30%, between about 19.5% and about 30%, between about 20% and about 30%, between about 22.5% and about 30%, between about 25% and about 30%, or between about 27.5% and about 30% trehalose.

Embodiment 70. The frozen fecal microbe composition of embodiment 63, wherein said composition comprises between about 12.5% and about 25%, between about 13% and about 25%, between about 13.5% and about 25%, between about 14% and about 25%, between about 14.5% and about 25%, between about 15% and about 25%, between about 15.5% and about 25%, between about 16% and about 25%, between about 16.5% and about 25%, between about 17% and about 25%, between about 17.5% and about 25%, between about 18% and about 25%, between about 18.5% and about 25%, between about 19% and about 25%, between about 19.5% and about 25%, between about 20% and about 25%, or between about 22.5% and about 25% trehalose.

Embodiment 71. The frozen fecal microbe composition of embodiment 63, wherein said composition comprises between about 12.5% and about 20%, between about 13% and about 20%, between about 13.5% and about 20%, between about 14% and about 20%, between about 14.5% and about 20%, between about 15% and about 20%, between about 15.5% and about 20%, between about 16% and about 20%, between about 16.5% and about 20%, between about 17% and about 20%, between about 17.5% and about 20%, between about 18% and about 20%, between about 18.5% and about 20%, between about 19% and about 20%, or between about 19.5% and about 20% trehalose.

Embodiment 72. The frozen fecal microbe composition of embodiment 63, wherein said composition comprises between about 12.5% and about 17.5%, between about 13% and about 17.5%, between about 13.5% and about 17.5%, between about 14% and about 17.5%, between about 14.5% and about 17.5%, between about 15% and about 17.5%, between about 15.5% and about 17.5%, between about 16% and about 17.5%, between about 16.5% and about 17.5%, or between about 17% and about 17.5% trehalose.

Embodiment 73. The frozen fecal microbe composition of embodiment 63, wherein said composition comprises between about 12.5% and about 17.5%, between about 13% and about 17%, between about 13.5% and about 16.5%, between about 14% and about 16%, or between about 14.5% and about 15.5% trehalose.

Embodiment 74. The frozen fecal microbe composition of embodiment 63, wherein said composition comprises about 15% trehalose.

Embodiment 75. The frozen fecal microbe composition of embodiment 63, wherein said composition comprises 15% trehalose.

Embodiment 76. The frozen fecal microbe composition of any one of embodiments 63 to 75, wherein said composition further comprises cysteine selected from the group consisting of D-cysteine and L-cysteine.

Embodiment 77. The frozen fecal microbe composition of embodiment 76, wherein said cysteine is at a concentration of at least about 0.025%.

Embodiment 78. The frozen fecal microbe composition of embodiment 76, wherein said cysteine is at a concentration of about 0.025%.

Embodiment 79. The frozen fecal microbe composition of embodiment 76, wherein said cysteine is at a concentration of 0.025%.

Embodiment 80. The frozen fecal microbe composition of embodiment 76, wherein said cysteine is at a concentration of at least about 0.005%, at least about 0.01%, at least about 0.015%, at least about 0.02%, at least about 0.025%, at least about 0.03%, at least about 0.035%, at least about 0.04%, at least about 0.045%, at least about 0.05%, at least about 0.055%, at least about 0.06%, at least about 0.065%, at least about 0.07%, at least about 0.075%, at least about 0.08%, at least about 0.085%, at least about 0.09%, at least about 0.095%, at least about 0.1%, at least about 0.12%, at least about 0.14%, at least about 0.16%, at least about 0.18%, at least about 0.2%, at least about 0.25%, at least about 0.3%, at least about 0.4%, at least about 0.5%, at least about 0.6%, at least about 0.7%, at least about 0.8%, at least about 0.9%, at least about 1%, at least about 2%, at least about 4%, at least about 6%, at least about 8%, at least about 10%, at least about 12%, at least about 14%, at least about 16%, at least about 18%, at least about 20%, at least about 22%, at least about 24%, or at least about 26%.

Embodiment 81. The frozen fecal microbe composition of embodiment 76, wherein said cysteine is at a concentration of between about 0.005% and about 0.1%, between about 0.01% and about 0.1%, between about 0.015% and about 0.1%, between about 0.02% and about 0.1%, between about 0.025% and about 0.1%, between about 0.03% and about 0.1%, between about 0.035% and about 0.1%, between about 0.04% and about 0.1%, between about 0.045% and about 0.1%, between about 0.05% and about 0.1%, between about 0.055% and about 0.1%, between about 0.06% and about 0.1%, between about 0.065% and about 0.1%, between about 0.07% and about 0.1%, between about 0.075% and about 0.1%, between about 0.08% and about 0.1%, between about 0.085% and about 0.1%, between about 0.09% and about 0.1%, between about 0.095% and about 0.1%.

Embodiment 82. The frozen fecal microbe composition of embodiment 76, wherein said cysteine is at a concentration of between about 0.005% and about 0.08%, between about 0.01% and about 0.08%, between about 0.015% and about 0.08%, between about 0.02% and about 0.08%, between about 0.025% and about 0.08%, between about 0.03% and about 0.08%, between about 0.035% and about 0.08%, between about 0.04% and about 0.08%, between about 0.045% and about 0.08%, between about 0.05% and about 0.08%, between about 0.055% and about 0.08%, between about 0.06% and about 0.08%, between about 0.065% and about 0.08%, between about 0.07% and about 0.08%, or between about 0.075% and about 0.08%.

Embodiment 83. The frozen fecal microbe composition of embodiment 76, wherein said cysteine is at a concentration of between about 0.005% and about 0.06%, between about 0.01% and about 0.06%, between about 0.015% and about 0.06%, between about 0.02% and about 0.06%, between about 0.025% and about 0.06%, between about 0.03% and about 0.06%, between about 0.035% and about 0.06%, between about 0.04% and about 0.06%, between about 0.045% and about 0.06%, between about 0.05% and about 0.06%, or between about 0.055% and about 0.06%.

Embodiment 84. The frozen fecal microbe composition of embodiment 76, wherein said cysteine is at a concentration of between about 0.005% and about 0.04%, between about 0.01% and about 0.04%, between about 0.015% and about 0.04%, between about 0.02% and about 0.04%, between about 0.025% and about 0.04%, between about 0.03% and about 0.04%, or between about 0.035% and about 0.04%.

Embodiment 85. The frozen fecal microbe composition of embodiment 76, wherein said cysteine is at a concentration of between about 0.005% and about 0.06%, between about 0.01% and about 0.05%, between about 0.015% and about 0.04%, or between about 0.02% and about 0.03%.

Embodiment 86. The frozen fecal microbe composition of any one of embodiments 63 to 85, wherein said fecal microbe composition comprises a non-selected and substantially complete fecal microbiota preparation from a single donor.

Embodiment 87. The frozen fecal microbe composition of embodiment 86, wherein the weight ratio between fecal-derived non-living material and fecal-derived biological material in said fecal microbiota preparation is no greater than 20%.

Embodiment 88. The frozen fecal microbe composition of embodiment 86, wherein the preparation of said fecal microbe preparation involves a treatment selected from the group consisting of ethanol treatment, detergent treatment, heat treatment, irradiation, and sonication, or a combination thereof.

Embodiment 89. The frozen fecal microbe composition of embodiment 86, wherein the preparation of said fecal microbe preparation involves a separation step selected from the group consisting of filtering, sieving, density gradients, filtration, chromatography, and a combination thereof.

Embodiment 90. The frozen fecal microbe composition of embodiment 86, wherein after at least 12 weeks of storage at ambient temperature or lower said fecal microbiota preparation is capable of maintaining at least 60% cell viability relative to the initial cell viability immediately prior to storage.

Embodiment 91. The frozen fecal microbe composition of embodiment 90, wherein after at least 12 weeks of storage at ambient temperature or lower said fecal microbiota preparation is capable of maintaining about 60% to about 80% cell viability relative to the initial cell viability at the start of said storage.

Embodiment 92. The frozen fecal microbe composition of embodiment 90, wherein the cell viability is measured by assessing cell membrane permeability via a combination of membrane permeant and impermeant DNA dyes stains.

Embodiment 93. The frozen fecal microbe composition of embodiment 63, wherein said composition further comprises one or more cryoprotectants selected from the group consisting of dimethyl sulfoxide (DMSO), glycerol, polyethylene glycol (PEG), alanine, glycine, proline, mannitol, sucrose, glucose, lactose, ribose, hydroxypropyl-fl-cyclodextrin (HPβCD), and any combination thereof.

Embodiment 94. The frozen fecal microbe composition of embodiment 63, wherein said composition is for oral administration.

Embodiment 95. The frozen fecal microbe composition of embodiment 63, wherein said composition is formulated as a geltab, pill, microcapsule, capsule, or tablet.

Embodiment 96. The frozen fecal microbe composition of embodiment 63, wherein every 200 mg of said composition comprises a pharmacologically active dose of microbes or spores selected from the group consisting of $10^3$ to $10^{14}$, $10^4$ to $10^{14}$, $10^5$ to $10^{14}$, $10^6$ to $10^{14}$, $10^7$ to $10^{14}$, $10^8$ to $10^{14}$, $10^4$ to $10^{13}$, $10^5$ to $10^{12}$, $10^6$ to $10^{11}$, $10^7$ to $10^{10}$, $10^8$ to $10^9$, $10^3$ to $10^{13}$, $10^3$ to $10^{12}$, $10^3$ to $10^{11}$, $10^3$ to $10^{10}$, $10^3$ to $10^9$, $10^3$ to $10^8$, $10^3$ to $10^7$, $10^3$ to $10^6$, $10^3$ to $10^5$, and $10^3$ to $10^4$ cfu or total cell count.

Embodiment 97. The frozen fecal microbe composition of embodiment 63, wherein said fecal microbe composition has at least about 20%, 30%, 40%, 50%, 60%, 70%, 80%, 85%, 90%, 95%, 99%, or 99.5% microbes in a spore form.

Embodiment 98. The frozen fecal microbe composition of embodiment 63, wherein said composition is effective for treating one or more disorders selected from the group consisting of recurrent or primary *C. difficile* infection, autism spectrum disorder (ASD), ulcerative colitis, Crohn's disease, and irritable bowel syndrome.

Embodiment 99. A method for treating a disorder or condition in a subject in need thereof, comprising administering to said subject a therapeutically effective amount of a pharmaceutical composition of any one of embodiments 1 to 52 or a frozen fecal microbe composition of any one of embodiments 63 to 98, wherein said disorder or condition is selected from the group consisting of Acne, AIDS Enteropathy, AIDS-related Gastroenteritis, Alopecia Totalis, Alzheimers Disease, Amyloidosis, Amyotrophic Lateral Sclerosis, Ankylosing Spondylitis, Anorexia, Antibiotic Associated Colitis, Asbergers Syndrome, Attention Deficit Disorder (ADD), Attention Deficit Hyperactivity Disorder (ADHD), Autism Spectrum Disorder (ASD), Behcet's Syndrome, Chronic *Clostridium difficile* Infection (CDI), Chronic constipation, Chronic Depression, Chronic Fatigue Syndrome (CFS), Chronic Idiopathic Pseudo Obstructive Syndrome, Chronic Inflammation Demyelinating Polyneuropathy, Chronic Nausea, Chronic Urticaria, Coeliac Disease, Collagenous Colitis, Colonic Polyps, Constipation Predominant FBD, Crohn's Disease, Cryptogenic Cirrhosis, Cyclic Vomiting, Dermatitis Herpetiformis, Diabetes, Familial Mediterranean Fever, Fatty Liver, Functional Bowel Disease (FBD), Gastro-oesophageal Reflux, Gillian-Barre Syndrome, Glomerulonephritis, Haemolytic Uraemic Syndrome, Halitosis, IBS constipation-predominant, IBS diarrhea/constipation alternating, IBS diarrhea-predominant, IBS pain-predominant, Idiopathic Thrombocytopenic Purpura (ITP), Idiopathic/Simple Constipation, Indeterminate Colitis, Inflammatory Bowel Disease (IBD), Irritable bowel syndrome (IBS), Juvenile Diabetes Mellitus, Lyme Disease, Manic Depressive Illness, Metabolic Syndrome, Microscopic Colitis, Migraine, Mixed Cryoglobulinaemia, Mucous Colitis, Multiple Sclerosis, Myasthenia Gravis, NASH (Nonalcoholic Steatohepatitis), Non-Rheumatoid Arthritis, Non-Rheumatoid Factor Positive Arthritis, Non-ulcer Dyspepsia, Norwalk Viral Gastroenteritis, Obesity, Obsessive Compulsive Disorder, Pain Predominant FBD, Parkinson's Disease, Polyarteritis, Polyposis *Coli*, Primary Biliary Cirrhosis, Primary *Clostridium difficile* Infection (CDI), Primary Sclerosing Cholangitis (PSC), Pseudomembranous Colitis, Psychotic Disorders, Reiter's Syndrome, Relapsing Diverticulitis, Rett Syndrome, Rheumatoid Arthritis, Rosacea, Rotavirus Gastroenteritis, Sacroiliitis, Schizophrenia, Scleroderma, Sjogren's Syndrome, Small Bowel Bacterial Overgrowth, Sudden Infant Death Syndrome (SIDS), Systemic Lupus Erythematosus, Ulcerative Colitis, Upper Abdominal FBD, Vasculitic Disorders, Viral Gastroenteritis, pre-diabetic syndrome, type I diabetes, type II diabetes, depression, schizophrenia, and a mood disorder.

Embodiment 100. A method for treating a disorder or condition in a subject in need thereof, comprising administering to said subject a therapeutically effective amount of a pharmaceutical composition of any one of embodiments 1 to 52 or a frozen fecal microbe composition of any one of embodiments 63 to 98, wherein said disorder or condition is selected from the group consisting of recurrent *C. difficile* infection, autism spectrum disorder (ASD), constipation predominant functional bowel disease (FBD), pain predominant FBD, upper abdominal FBD, non-ulcer dyspepsia (NUD), gastro-oesophageal reflux, indeterminate colitis, microscopic colitis, pseudomembranous colitis, viral gastroenteritis, Norwalk viral gastroenteritis, rotavirus gastroenteritis, AIDS related gastroenteritis, non-rheumatoid factor positive arthritis, Lyme disease, systemic lupus, idiopathic thrombocytopenic purpura, Sjogren's syndrome, haemolytic uremic syndrome or scleroderma, Gillain-Barre syndrome, Chronic Inflammatory Demyelinating Polyneuropathy, chronic depression, schizophrenia, psychotic disorders, manic depressive illness, Asbergers syndrome, Rett syndrome, attention deficit hyperactivity disorder (ADHD), and attention deficit disorder (ADD), sudden infant death syndrome (SIDS), anorexia nervosa.

Embodiment 101. A method for treating a disorder or condition in a subject in need thereof, comprising administering to said subject a therapeutically effective amount of a pharmaceutical composition of any one of embodiments 1 to 52 or a frozen fecal microbe composition of any one of embodiments 63 to 98, wherein said disorder or condition is selected from the group consisting of recurrent or primary *C. difficile* infection, autism spectrum disorder (ASD), ulcerative colitis, Crohn's disease, and irritable bowel syndrome.

While the present disclosure has been described with reference to particular embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope of the present disclosure.

Therefore, it is intended that the present disclosure not be limited to the particular embodiments disclosed as the best mode contemplated for carrying out the present disclosure, but that the present disclosure will include all embodiments falling within the scope and spirit of the appended claims.

EXAMPLES

Example 1: Testing of Various Lyoprotectants for Effective Preservation of Fecal Cell Viability A study is designed to determine an effective lyoprotectant formulation for preserving the viability of microorganisms in lyophilized fecal microbiota preparations. Microbial cell membrane integrity is used as a surrogate marker for cell viability.

A liquid fecal microbiota extract is obtained via a process containing a homogenization step followed by a filtration step. In the homogenization step, a donated stool is mixed with a fixed ratio of homogenization buffer solution to stool to homogenize using a mechanical device to form stool slurry. After testing various ratios, an optimal ratio of 3 mL of homogenization buffer per gram of wet stool is established. The resulting stool slurry is filtered through a mesh filter (e.g., with a filter pore size of 330 μm) to generate a liquid fecal microbiota extract. This step removes a majority of the non-microbial fecal particulate matter present in the donor stool, including undigested food. Microbial cell viability is measured as in Example 2 based on cell membrane integrity. Membrane integrity of fresh donor material varies from 49% to 90%, even from the same donor. Equal or greater than 50% membrane integrity (% viability) is used to assess the quality of a liquid fecal microbiota extract.

The liquid fecal microbiota extract is then subject to further processing (e.g., lyophilization) to produce a lyophilized fecal microbiota preparation. Microbial cell viability is measured as in Example 2 both prior to and after the lyophilization step to determine a cell integrity maintenance ratio for each corresponding homogenization buffer. A cell integrity maintenance ratio is defined as the percent of microbial cells containing integral membrane post-lyophilization relative to pre-lyophilization.

Various homogenization buffer formulations are tested for their effect in maximizing microbial cell recovery from donor stool, as well as preserving membrane integrity (cell viability) during lyophilization. The present disclosure shows that 15% trehalose is found to be the most effective in maintaining cell membrane integrity and preserving cell viability during lyophilization. After a series of experiments, 15% trehalose are selected for their protective effect as measured by least impact on membrane integrity post freeze-thaw as well as post lyophilization. Representative data are presented below in Table 1 showing the effect of a homogenization buffer (0.25X Phosphate-buffered saline, pH 7.4 and 15% w/v of trehalose) over membrane integrity through a lyophilization process. For Donor #55, prior to lyophilization, 66.5% of microbes contain integral membrane. After lyophilization in the presence of 15% trehalose, 31.2% of microbes retain integral membrane, which amounts to a cell integrity maintenance ratio of about 46.9%. For Donor #62, prior to lyophilization, 70.9% of microbes contain integral membrane. After lyophilization in the presence of 15% trehalose, 43.7% of microbes retain integral membrane, which amounts to a cell integrity maintenance ratio of about 61.6%.

TABLE 1

Effect of Trehalose Concentration on Membrane Integrity

| Donor # | 55 | | | 62 | | |
|---|---|---|---|---|---|---|
| Membrane Integrity (% viability) pre-lyophilization | 66.5% | | | 70.9% | | |
| Trehalose concentration | 5% | 10% | 15% | 5% | 10% | 15% |
| Membrane Integrity (% viability) post-lyophilization | 4.4% | 11.6% | 31.2% | 15.2% | 25.3% | 43.7% |
| Cell integrity maintenance ratio | 6.6% | 17.4% | 46.9% | 21.4% | 35.7% | 61.6% |

Example 2: Measurement of Microbial Cell Concentration and Cell Membrane Integrity To monitor total cell number and determine proper dosage of a fecal microbiota preparation, cell concentration is measured using a fluorescence microscope-based method. Samples are serially diluted (from 1:10 to 1:10,000 folds) using sterile saline and then mixed with 1 μL of SYTO™ BC dye (Invitrogen, CA) to stain cells and 1 μL Prolong Anti-Fade Reagent (Invitrogen, CA) to minimize photo-bleaching of dye. The combined solution is mixed and incubated in the dark for 15 minutes at room temperature and analyzed using a Petroff-Hauser counting chamber.

Briefly, a 10 μl stained sample is applied to chamber, covered with a coverslip and visualized using an epifluorescence microscope (Nikon Corporation) equipped with a 40X objective, sola light engine and a filter specific for SYTO BC dye (Excitation 470 nm/Emission 525 nm). The SYTO BC dye penetrates all intact microbial cells, whether alive or dead and these stained cells appear green when visualized in the epifluorescence microscope using the specific green filter (Excitation 470 nm/Emission 525 nm). Cells are counted in 5 squares. The process is repeated with 3 separate aliquots and average cells counted in each square are then used to calculate total cell concentration.

The membrane integrity (cell viability) is also measured using a fluorescence microscope-based method. The method is essentially the same as described above for cell concentration except two separate dyes are used. One aliquot is stained with SYTO BC as described above, and a second aliquot is stained with another dye, 1.5 μL Propidium Iodide (Invitrogen, CA).

Whereas the SYTO BC dye penetrates all cells which stain green, the Propidium Iodide (PI) dye only penetrates cells with a loss of membrane integrity (i.e. injured or dead cells), and the PI stained cells appear red when visualized under the epifluorescence microscope using the specific red filter (Excitation 560 nm/Emission 630 nm).

Example 3: Cell Stability from Freeze and Thaw Cycles

The impact of repeated freeze-thaw cycles is evaluated over the cell stability of a fecal microbiota extract. A liquid fecal microbiota extract from Example 1 is subject to repeated freeze-thaw (FT) cycles (FT1, FT2 and FT3) where one cycle is defined as freezing samples at −80° C. for a minimum of 24 hours followed by thawing at ambient temperature for a minimum of 30 minutes or until completely thawed as monitored visually. Results of these studies are provided below in Table 2. When mixed and extracted using a homogenization buffer (0.25X Phosphate-buffered saline, pH 7.4, 0.025% w/v L-Cysteine and 15% w/v of Trehalose), fecal material can be frozen and thawed at least two times without significantly impacting cell count and membrane integrity.

TABLE 2

Freeze-thaw stability of a fecal microbiota extract.

| Donor | Cell Concentration (cells/mL) | | | | Membrane Integrity (% Viability) | | | |
|---|---|---|---|---|---|---|---|---|
| | Initial (t0) | FT1 | FT2 | FT3 | Initial (t0) | FT1 | FT2 | FT3 |
| 42 | $7.3 \times 10^{10}$ | $7.4 \times 10^{10}$ | $8.4 \times 10^{10}$ | $7.3 \times 10^{10}$ | 65% | 55% | 50% | 36% |
| 55 | $8.4 \times 10^{10}$ | $7.6 \times 10^{10}$ | $7.2 \times 10^{10}$ | $7.8 \times 10^{11}$ | 63% | 49% | 27% | 49% |
| 62 | $1.2 \times 10^{11}$ | $9.6 \times 10^{10}$ | $1.1 \times 10^{11}$ | $8.6 \times 10^{11}$ | 69% | 53% | 47% | 36% |
| 63 | $3.1 \times 10^{10}$ | $4.2 \times 10^{10}$ | $3.4 \times 10^{10}$ | $3.4 \times 10^{10}$ | 64% | 49% | 42% | 38% |

Example 4: Exemplary Clinical Treatment

A lyophilized fecal microbiota preparation described above comprising trehalose and Cysteine, is encapsulated in a delay-release capsule to open in the small intestine of patients. The capsules are stored at 2-8° C. Capsules are given to patients with microbiologically-proven second or fifth recurrent *Clostridium difficile* infection.

Example 5: Testing of Various Reducing Agents for Effective Preservation of Fecal Cell Viability A study is designed to determine an effective reducing agent formulation for preserving the viability of microorganisms in lyophilized fecal microbiota preparations. Microbial cell membrane integrity is used as a surrogate marker for cell viability.

Stool is collected from a donor and two samples are analyzed in parallel (0.05% Sodium Ascorbate, and 0.025% Cysteine) with stool divided from a single donor. The experiment is duplicated with stool from a second donor. A liquid fecal microbiota extract is obtained via a process containing a homogenization step followed by a filtration step as described in Example 1. In the homogenization step, a donated stool is mixed with a fixed ratio of homogenization buffer solution containing 0.05% w/v sodium ascorbate or 0.025% w/v cysteine.

The liquid fecal microbiota extract is then subject to further processing (e.g., lyophilization with 15% trehalose, blending, and encapsulation) to produce a lyophilized fecal microbiota preparation. Microbial cell viability is measured, as in Example 2, at the homogenization step, after the addition of trehalose (formulated drug substance step), after the lyophilization step, and after blending for each sample. Table 3 shows that both reducing agents, sodium ascorbate and cysteine, have higher membrane viability at each step.

TABLE 3

Effect of Reducing Agents on Membrane Integrity

| Membrane Integrity | Donor 1 | | | Donor 2 | | |
|---|---|---|---|---|---|---|
| | Control* | 0.05% Sodium Ascorbate | 0.025% Cysteine | Control* | 0.05% Sodium Ascorbate | 0.025% Cysteine |
| Homogenized stool | 70% | 49% | 42% | 61% | 65% | 54% |
| Formulated drug Substance | 25% | 53% | 62% | 52% | 67% | 49% |
| Change | 45% | (4%) | (20%) | 9% | (2%) | 6% |
| Lyophilized Material | 36% | 35% | 41% | 48% | 41% | 39% |
| Encapsulation Material | 9.9% | 29% | 15% | 29% | 39% | 38% |

*different donation

Percentages in parenthesis indicate a decrease.

Change indicates difference between homogenized stool and formulated drug substance.

A number of aspects have been described. Nevertheless, it will be understood that various modifications may be made without departing from the spirit and scope of the disclosure.

What is claimed is:

1. A pharmaceutical composition comprising a lyophilized fecal microbe preparation comprising microbial cells derived from a healthy human donor and a lyophilization formulation, wherein, prior to lyophilization, said lyophilization formulation comprises between about 12.5% and about 60% trehalose and between about 0.005% and about 0.08% cysteine.

2. The pharmaceutical composition of claim 1, wherein said cysteine is D-cysteine.

3. The pharmaceutical composition of claim 1, wherein said lyophilization formulation comprises about 0.025% cysteine.

4. The pharmaceutical composition of claim 1, wherein said fecal microbe preparation comprises a non-selected fecal microbiota preparation from a single donor.

5. The pharmaceutical composition of claim 4, wherein the preparation of said fecal microbe preparation involves a separation step selected from the group consisting of filtering, sieving, density gradients, filtration, chromatography, sedimentation, centrifugation, and a combination thereof.

6. The pharmaceutical composition of claim 4, wherein said lyophilized formulation further comprises one or more cryoprotectants selected from the group consisting of dimethyl sulfoxide (DMSO), glycerol, polyethylene glycol (PEG), alanine, glycine, proline, mannitol, sucrose, glucose, lactose, ribose, hydroxypropyl-β-cyclodextrin (HPβCD), and any combination thereof.

7. The pharmaceutical composition of claim 4, wherein said pharmaceutical composition is in an oral formulation.

8. The pharmaceutical composition of claim 4, wherein said pharmaceutical composition is formulated as a geltab, pill, microcapsule, capsule, or tablet.

9. The pharmaceutical composition of claim 4, wherein every 200 mg of said pharmaceutical composition comprises a pharmacologically active dose of microbes or spores from $10^3$ to $10^{15}$ cfu or total cell count.

10. The pharmaceutical composition of claim 4, wherein said fecal microbe preparation has at least about 50% microbes in a spore form.

11. The pharmaceutical composition of claim 1, wherein said lyophilization formulation comprises about 15% trehalose.

12. The pharmaceutical composition of claim 1, wherein said lyophilization formulation comprises about 20% trehalose.

13. The pharmaceutical composition of claim 1, wherein cysteine is L-cysteine.

14. The pharmaceutical composition of claim 1, wherein, prior to lyophilization, said lyophilization formulation is in the form of a liquid.

15. The pharmaceutical composition of claim 14, wherein said liquid comprises a buffering agent.

16. The pharmaceutical composition of claim 15, wherein said buffering agent comprises phosphate-buffered saline.

17. The pharmaceutical composition of claim 1, wherein said lyophilized fecal microbe preparation further comprises an inert powdered diluent.

* * * * *